United States Patent
Mantegani et al.

(10) Patent No.: US 8,309,578 B2
(45) Date of Patent: Nov. 13, 2012

(54) BICYCLIC PYRAZOLE AND ISOXAZOLE DERIVATIVES AS ANTITUMOR AND ANTINEURODEGENERATIVE AGENTS

(75) Inventors: Sergio Mantegani, Milan (IT); Maria Gabriella Brasca, Cusago (IT); Francesco Casuscelli, Dairago (IT); Ron Ferguson, Scotch Plains, NJ (US); Helena Posteri, Travedona Monate (IT); Carlo Visco, Milan (IT); Elena Casale, Somma Lombardo (IT); Fabio Zuccotto, Milan (IT)

(73) Assignee: Nerviano Medical Sciences S.r.l., Nerviano (MI) (IT)

( * ) Notice: Subject to any disclaimer, the term of this patent is extended or adjusted under 35 U.S.C. 154(b) by 0 days.

(21) Appl. No.: 13/130,614

(22) PCT Filed: Nov. 19, 2009

(86) PCT No.: PCT/EP2009/065480
§ 371 (c)(1),
(2), (4) Date: Aug. 12, 2011

(87) PCT Pub. No.: WO2010/060854
PCT Pub. Date: Jun. 3, 2010

(65) Prior Publication Data
US 2011/0294790 A1     Dec. 1, 2011

(30) Foreign Application Priority Data
Nov. 25, 2008 (EP) .................................. 08169854

(51) Int. Cl.
*A61K 31/4355* (2006.01)
*A61K 31/437* (2006.01)
*C07D 471/04* (2006.01)
*C07D 487/04* (2006.01)
*C07D 498/04* (2006.01)

(52) U.S. Cl. ........ 514/326; 514/379; 514/403; 546/192; 548/217; 548/360.1

(58) Field of Classification Search ................. 514/379, 514/403, 326; 548/217, 360.1; 546/192
See application file for complete search history.

(56) References Cited

FOREIGN PATENT DOCUMENTS

| WO | WO 03/101989 A1 | 12/2003 |
|---|---|---|
| WO | WO 2004/050087 A1 | 6/2004 |
| WO | WO-2005/040169 * | 5/2005 |
| WO | WO 2005/040169 A2 | 5/2005 |
| WO | WO 2008/104595 A1 | 9/2008 |

OTHER PUBLICATIONS

Brough, Paul A. et al., "3-(5-chloro-2,4-dihydroxyphenyl)-Pyrazole-4-carboximides as inhibitors of the Hsp90 molecular chaperone", Bioorganic & Medicinal Chemistry Letters (2005), vol. 15, No. 23, pp. 5197-5201.
International Search Report dated Mar. 10, 2010 issued in PCT/EP2009/065480.

* cited by examiner

*Primary Examiner* — Kamal Saeed
*Assistant Examiner* — Janet L Coppins
(74) *Attorney, Agent, or Firm* — Scully, Scott, Murphy & Presser, P.C.

(57) ABSTRACT

Bicyclic pyrazole and isoxazole derivatives of formula (I) and pharmaceutically acceptable salts thereof, as defined in the specification, process for their preparation and pharmaceutical compositions comprising them are disclosed; the compounds of the invention may be useful in therapy in the treatment of diseases mediated by HSP90 protein, like cancer and neurodegenerative disorders.

20 Claims, No Drawings

BICYCLIC PYRAZOLE AND ISOXAZOLE DERIVATIVES AS ANTITUMOR AND ANTINEURODEGENERATIVE AGENTS

The present invention relates to certain substituted bicyclic pyrazole and isoxazole compounds which inhibit the activity of Heat Shock Protein 90 (Hsp90). The compounds of this invention are therefore useful in treating proliferative diseases such as cancer and neurodegenerative diseases. The present invention also provides methods for preparing these compounds, pharmaceutical compositions comprising these compounds, and methods of treating diseases utilizing pharmaceutical compositions comprising these compounds.

The current targeted therapies for the treatment of cancer are based on the identification of specific proteins that drive tumour progression, and on the identification of a specific agent capable of antagonizing the effect of this protein. Most of the efforts of the pharma industry are directed towards a very limited number of well validated protein targets. A common drawback is the arising of drug resistant mutations frequently found in cancer patients that are treated with these specific inhibitors. Recently, the common opinion is that the simultaneous block of signalling pathways involved in cancer progression is expected to determine a better anti-tumour efficacy, and also a lower probability to develop resistance. Hsp90 belongs to a small family of proteins (GHKL, from DNA Gyrase, HSP90, histidine Kinase, mutL) sharing in common a very specific C shaped mode of binding to ATP (Bergerat fold). Hsp90 is one of the most abundant proteins in cells, essential for viability in eukaryotes. The human cell contains four isoforms of Hsp90: the cytosolic β-isoform, which is constitutively expressed, the inducible α-form, GRP94/gp96 in the endoplasmatic reticulum, and the mitochondrial TRAP1/Hsp75. The α- and the β-form show 85% sequence identity.

Hsp90 is a key component of a chaperone machinery, it catalyzes the folding and quality control of proteins, called Hsp90 clients, in both normal cells and also under stress conditions. The chaperone activity, strictly dependent on the ATPase activity, is tightly regulated by the binding of other regulatory co-chaperones.

There are strong evidences that in disease conditions, such as cancer or other proliferative diseases, Hsp90 becomes critical, due to the mutation or overexpression of specific oncogenes or also because tumors often have an overload of misfolded proteins that leads to an increased requirement of chaperone function.

Structurally Hsp90 is an homodimer made of three main structured domains: an N terminal domain very conserved, the ATPase domain, a middle domain and a C terminal domain. The N and C terminal domains can bind ATP. Most of the currently known inhibitors such as geldanamycin, radicicol, diarylpyrazoles and purine derivatives show an ATP competitive binding to the N terminal ATP binding site, while novobiocin is the prototype of the inhibitors binding to the C terminal pocket.

At the moment, there is an increasing number of reported Hsp90 clients (Jolly, et al., J. Natl. Cancer Inst. 92; 1564-1572 (2000), belonging to the family of kinases (Her2, B-RAF V600E, bcr-Abl, Flt3, NPM-ALK, Akt, Npm-Alk, ZAP-70), trascription factors (p53, HIF) telomerase, other chaperones, most of them strictly related with cancer progression. Hsp90 inhibition impairs the capacity to fold or stabilize its client proteins, leading to the proteosomal dependent degradation of these unfolded proteins. The degradation of these client proteins is frequently used as a marker of Hsp90 inhibition, typically used is the degradation of Her2 after compound treatment in Her2 overexpressing cells, such as BT474 breast cancer cells.

A big wave of research in the field of Hsp90 inhibitors was initially driven by the evidence that the natural compound geldanamycin could actually block the proliferation of multiple tumour cells, by competitively binding to the N terminal ATP binding site and inhibiting the Hsp90 ATPase activity and function. Surprisingly, this compound was not active in normal cells, may be because Hsp90 is present in an active complex (with high affinity to geldanamycin) only in tumour cells (Kamal et al.). Another potential reason for the selective sensitivity for tumours is the tumour retention that many Hsp90 inhibitors show.

Tanespimycin (17-AAG), a semisynthetic derivative of geldanamycin, together with other related derivatives (alvespimycin, 17-DMAG, IPI-504) is under intense clinical evaluation, but the efficacy appear to be limited by a number of factors: cumbersome formulation, dependence on metabolism to generate the active metabolite, lack of patient enrichment, hepatic toxicity possibly related to the quinone moiety. This paved the way to an intense effort for the identification of second generation of Hsp90 inhibitors with a better drug-like profile and better tolerability. This led to the identification of purine derivatives and diaryl-resorcinol derivatives.

The major cause of neurodegenerative diseases such as Alzheimer's, Parkinson's, Huntington's, and prion disease is the accumulation of misfolded proteins that result in plaque formation. These misfolded proteins rely upon molecular chaperones (Hsp70, Hsp40, etc.) for rematuration, disaggregation, and resolubilization of protein aggregates. The heat shock proteins have been shown to provide this function in various cell culture models. Hsps can be induced by HSF1, which is tightly regulated by Hsp90 in normal cells. It has been demonstrated that Hsp90 inhibitors such as geldanamycin and the 17-AAG derivative can disrupt this interaction and lead to Hsp induction, resultant in neuroprotective activities and the resolubilization and disaggregation of misfolded proteins. Hsp90 overexpression can significantly decrease the accumulation of misfolded proteins, which are responsible for Alzheimer's, in fact it has been demonstrated an inverse relationship between aggregated tau and Hsp70/90 levels. Abnormal tau aggregation can be diminished (through degradation) by the overexpression of Hsp70, Hsp27, and Hsp40 which is triggered by the inhibition of Hsp90. Application of Hsp90 inhibitors for the management of Parkinson's disease finds ground on the in vivo effect of GDA on 1-methyl-4-phenyl-1,2,3,6-tetrahydropyridine (MPTP)-induced neurotoxicity of a mouse model for PD.

GDA protected the neurons from toxicity caused by MPTP, which was closely linked to increased Hsp70 levels. In addition, it has been also shown that Hsp90 overexpression can significantly decrease the accumulation of misfolded proteins, which are responsible for motor impairments, multiple sclerosis, spinal and bulbar muscular atrophy and other diseases.

Diaryl-pyrazoles and diaryl-isoxazoles for the treatment of conditions mediated by Hsp90 protein such as cancer, are disclosed respectively in WO 2003/055860 in the name of Ribotargets Ltd and in WO 2004/072051 in the name of Vernalis Ltd.

Aryl-pyrazoles fused with a cycle containing one nitrogen for the treatment of conditions related to serotonin disorders such as sleep disorders, migraine and depression, are disclosed respectively in WO 2005/040169 in the name of Janssen Pharm. and in EP 594001 in the name of Hoechst Roussel Pharma.

Aryl-pyrazoles fused with a cycle containing one nitrogen for the treatment of diseases caused by and/or associated with dysregulated protein kinase activity such as cancer, are also disclosed in WO 2004/013144 in the name of Pharmacia Italia Spa.

The present inventors have now discovered that compounds of formula (I), described below, are Hsp90 inhibitors and are thus useful in therapy as antitumor and antineurogenerative agents and have a better drug-like profile and better tolerability than the currently available antitumor drugs.

Accordingly, a first object of the present invention is to provide a substituted bicyclic pyrazole or isoxazole compound of formula (I):

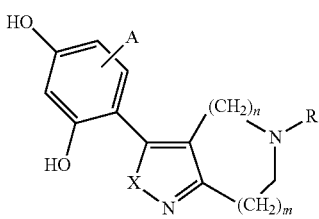

wherein:
A is halogen or an optionally substituted linear or branched $(C_1-C_6)$ alkyl, $(C_2-C_6)$ alkenyl or $(C_2-C_6)$ alkynyl;
X is oxygen or nitrogen;
R is hydrogen, $(CH_2)_p$—COR1, $(CH_2)_p$—COOR1, ZNHR1', $(CH_2)_p$—R1, $CH(R1')_2$ or $SO_2R2$,
wherein
R1 is hydrogen or R1';
R1' is a group optionally substituted selected from linear or branched $(C_1-C_6)$ alkyl, $(C_2-C_6)$ alkenyl, $(C_2-C_6)$ alkynyl, $(C_3-C_8)$ cycloalkyl, heterocyclyl, aryl and heteroaryl;
Z is a C=O or C=S group;
R2 is a group optionally substituted selected from linear or branched $(C_1-C_6)$ alkyl, $(C_3-C_8)$ cycloalkyl, heterocyclyl, aryl and heteroaryl;
m, n and p are independently an integer from 0 to 2, and pharmaceutically acceptable salts thereof.

The present invention also provides methods of synthesizing the substituted bicyclic pyrazole and the substituted bicyclic isoxazole compounds of formula (I), prepared through a process consisting of standard synthetic transformations.

The present invention also provides a method for treating diseases mediated by Hsp90 protein.

A preferred method of the present invention is to treat a disease mediated by Hsp90 protein selected from the group consisting of cancer and neurodegenerative disorders.

Another preferred method of the present invention is to treat specific types of cancer including but not limited to: carcinoma such as bladder, breast, colon, kidney, liver, lung, including small cell lung cancer, esophagus, gallbladder, ovary, pancreas, stomach, cervix, thyroid, prostate, and skin, including squamous cell carcinoma; hematopoietic tumors of lymphoid lineage including leukaemia, acute lymphocytic leukaemia, acute lymphoblastic leukaemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Another preferred method of the present invention is to treat neurodegenerative disorders including but not limited to: Alzheimer's, Parkinson's, Huntington's diseases, multiple sclerosis and spinal and bulbar muscular atrophy.

The present invention further provides a method of treatment comprising a compound of formula (I) in combination with radiation therapy or chemotherapy regimen for simultaneous, separate or sequential use in anticancer therapy. Moreover the invention provides an in-vitro method for inhibiting Hsp90 protein activity which comprises contacting the said protein with an effective amount of a compound of formula (I).

The present invention also provides a pharmaceutical composition comprising one or more compounds of formula (I) or a pharmaceutically acceptable salt thereof and a pharmaceutically acceptable excipient, carrier or diluent.

The present invention also provides a pharmaceutical composition comprising a compound of formula (I) in combination with known cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

Additionally, the invention provides a product or kit comprising a compound of formula (I) or a pharmaceutically acceptable salt thereof, as defined above, or pharmaceutical compositions thereof and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

Moreover the invention provides the use of a compound of formula (I) or a pharmaceutically acceptable salt thereof, as defined above, in the manufacture of a medicament with anticancer activity.

Additionally, the invention provides the use of a compound of formula (I) or a salt, as defined above, as a biochemical tool, e.g. as molecular probe.

Finally, the invention provides a compound of formula (I) or a pharmaceutically acceptable salt thereof, as defined above, for use in a method of treating cancer.

As used herein, a compound of formula (I) wherein A, m, n and R are as defined above and X is nitrogen may be represented by the general formula $(I)_A$:

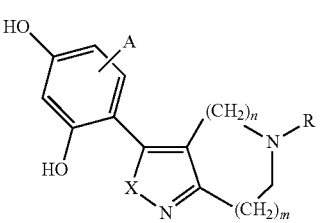

and a compound of formula (I) wherein A, m, n and R are as defined above and X is oxygen atom may be represented by the general formula $(I)_B$:

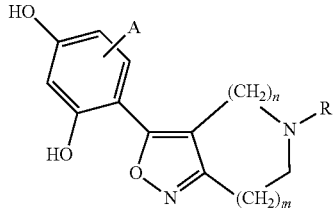

(I)<sub>B</sub>

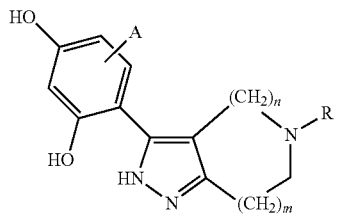

(Ib)<sub>A</sub>

Unless otherwise specified, when referring to the compounds of formula (I) per se as well as to any pharmaceutical composition thereof or to any therapeutic treatment comprising them, the present invention includes all of the isomers, tautomers, hydrates, solvates, complexes, metabolites, prodrugs, carriers, N-oxides and pharmaceutically acceptable salts of the compounds of this invention.

A metabolite of a compound of formula (I) is any compound into which this same compound of formula (I) is converted in vivo, for instance upon administration to a mammal in need thereof. Typically, without however representing a limiting example, upon administration of a compound of formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of formula (I).

Prodrugs are any covalently bonded compounds, which release in vivo the active parent drug according to formula (I).

If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

As such, unless otherwise provided, when in compounds of formula (I)<sub>A</sub>, only one of the following tautomeric forms of formula (Ia)<sub>A</sub> or (Ib)<sub>A</sub> is indicated, the remaining one has still to be intended as comprised within the scope of the invention:

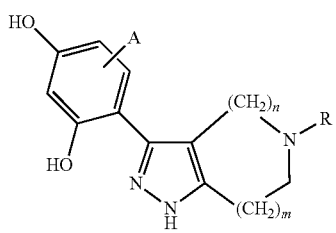

(Ia)<sub>A</sub>

In cases wherein compounds may exist in other tautomeric forms, such as keto-enol tautomers, each tautomeric form is contemplated as being included within this invention whether existing in equilibrium or predominantly in one form.

With the term halogen atom we intend a fluorine, chlorine, bromine or iodine atom.

With the term cyano we intend a —CN residue.

With the term nitro we intend a —NO$_2$ group.

With the term "straight or branched $C_1$-$C_6$ alkyl", we intend any of the groups such as, for instance, methyl, ethyl, n-propyl, isopropyl, n-butyl, isobutyl, tert-butyl, sec-butyl, n-pentyl, n-hexyl, and the like.

With the term "$C_2$-$C_6$ alkenyl" we intend an aliphatic $C_2$-$C_6$ hydrocarbon chain containing at least one carbon-carbon double bond and which can be straight or branched. Representative examples include, but are not limited to, ethenyl, 1-propenyl, 2-propenyl, 1- or 2-butenyl, and the like.

With the term "$C_2$-$C_6$ alkynyl" we intend an aliphatic $C_2$-$C_6$ hydrocarbon chain containing at least one carbon-carbon triple bond and which can be straight or branched. Representative examples include, but are not limited to, ethynyl, 1-propynyl, 2-propynyl, 1- or 2-butynyl, and the like.

With the term "$C_3$-$C_8$ cycloalkyl" we intend, unless otherwise provided, 3- to 8-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene and cyclohexadiene.

With the term "heterocyclyl" we intend a 3- to 8-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated π-electron bond system. Non limiting examples of such aryl groups are phenyl, α- or β-naphthyl or biphenyl groups.

The term "heteroaryl" refers to aromatic heterocyclic rings, typically 5- to 8-membered heterocycles with from 1 to 3 heteroatoms selected among N, O or S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl; benzopyranyl, 2,3-dihydrobenzoxazinyl, 2,3-dihydroquinoxalinyl and the like.

According to the present invention and unless otherwise provided, any of the above A, R, R1, R1' and R2 group may be optionally substituted, in any of their free positions, by one or more groups, for instance 1 to 6 groups, independently selected from: halogen, nitro, oxo groups (=O), cyano, cyanoalkylamino, $C_1$-$C_6$ alkyl, polyfluorinated alkyl, polyfluorinated alkoxy, $C_2$-$C_6$ alkenyl, $C_2$-$C_6$ alkynyl, hydroxyalkyl, aryl, arylalkyl, heteroaryl, heteroarylalkyl, heterocyclyl, heterocyclylalkyl, $C_3$-$C_8$ cycloalkyl, hydroxy, alkoxy, alkoxycarbonyl, alkoxycarbonylamino, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, aryloxycarbonyl, cycloalkyloxycarbonyl, heterocyclylalkyloxycarbonylamino, ureido, amino, alkylamino, dialkylamino, arylamino, diarylamino, heterocyclylamino, formylamino, alkylcarbonylamino, arylcarbonylamino, heterocyclylcarbonylamino, aminocarbonyl, acylamino, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, thioalkyl, alkylsulphanyl, alkylsulphonyl, alkylsulphenyl, arylsulphanyl, arylsulphonyl, arylsulphenyl, sulphonylamino, phosphonate and alkylphosphonate. In their turn, whenever appropriate, each of the above substituent may be further substituted by one or more of the aforementioned groups.

With the term polyfluorinated alkyl or polyfluorinated alkoxy we intend any of the above straight or branched $C_1$-$C_6$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term hydroxyalkyl we intend any of the above $C_1$-$C_6$ alkyl, bearing an hydroxyl group such as, for instance, hydroxymethyl, 2-hydroxyethyl, 3-hydroxypropyl and the like.

From all of the above, it is clear to the skilled person that any group which name is a composite name such as, for instance, arylamino has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $C_3$-$C_8$ cycloalkyl and heterocyclyl moieties are as above defined.

Pharmaceutically acceptable salts of the compounds of formula (I) include the acid addition salts with inorganic or organic acids, e.g., nitric, hydrochloric, hydrobromic, sulfuric, perchloric, phosphoric, acetic, trifluoroacetic, propionic, glycolic, lactic, oxalic, fumaric, malonic, malic, maleic, tartaric, citric, benzoic, cinnamic, mandelic, methanesulphonic, isethionic and salicylic acid.

Pharmaceutically acceptable salts of the compounds of formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines, preferably methylamine, ethylamine, diethylamine, triethylamine, piperidine and the like.

Preferred compounds of the present invention are 4,5,6,7-tetrahydro-1H-pyrazolo[3,4-c]pyridine derivatives of formula (I)A1 and 4,5,6,7-tetrahydroisoxazolo[3,4-c]pyridine derivatives of formula (I)B1:

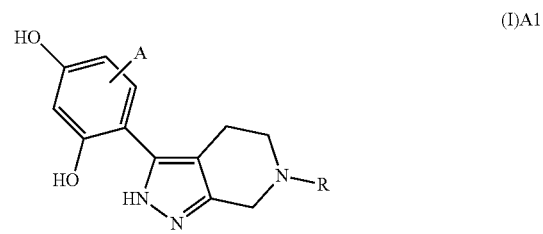

(I)A1

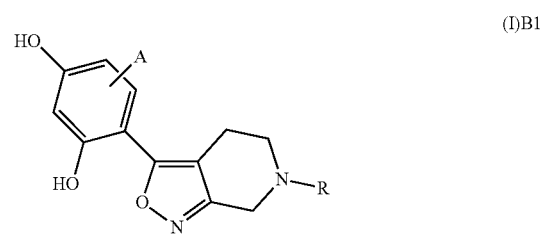

(I)B1 that is compounds of formula (I) wherein m is 0 and n is 2.

Other preferred compounds of the present invention are 4,5,6,7-tetrahydro-2H-pyrazolo[4,3-c]pyridine derivatives of formula (I)A2 and 4,5,6,7-tetrahydro-isoxazolo[4,3-c]pyridine of formula (I)B2:

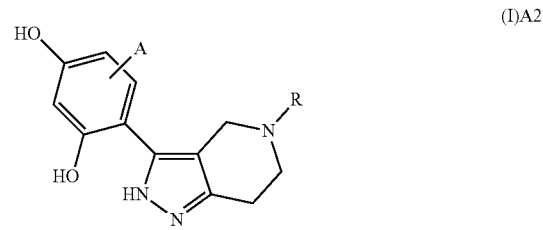

(I)A2

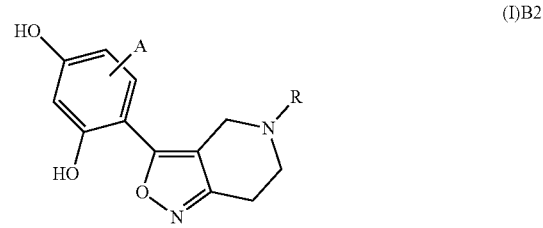

(I)B2 that is compounds of formula (I) wherein m is 1 and n is 1.

Further preferred compounds of the present invention are 4,5,6,7-tetrahydro-2H-pyrazolo[4,3-b]pyridine derivatives of formula (I)A3 and 4,5,6,7-tetrahydro-isoxazolo[4,3-b]pyridine derivatives of formula (I)B3:

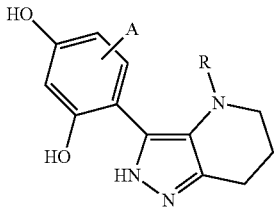

(I)A3

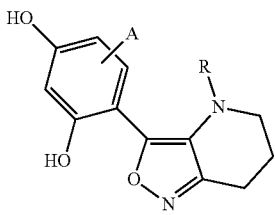

(I)B3 that is compounds of formula (I) wherein m is 2 and n is 0.

Other further preferred compounds of the present invention are 1,4,5,6-tetrahydropyrrolo[3,4-c]pyrazole of formula (I)A4 and 5,6-dihydro-4H-pyrrolo[3,4-c]isoxazole derivatives of formula (I)B4:

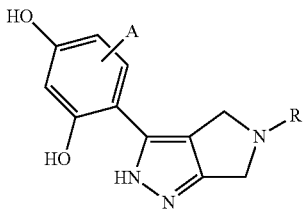

(I)A4

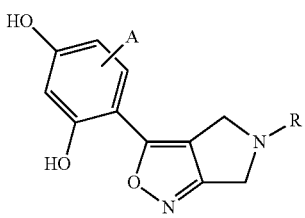

(I)B4 that is compounds of formula (I) wherein m is 0 and n is 1.

Other further preferred compounds of the present invention are 1,4,5,6-tetrahydropyrrolo[3,2-c]pyrazole of formula (I)A5 and 5,6-dihydro-4H-pyrrolo[3,2-c]isoxazole derivatives of formula (I)B5:

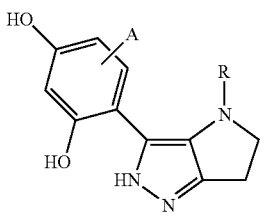

(I)A5

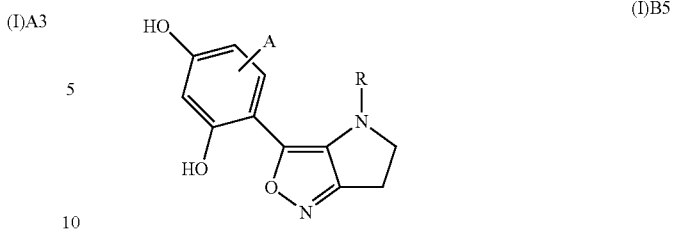

(I)B5 that is compounds of formula (I) wherein m is 1 and n is 0.

A more preferred class of compounds of formula (I) is represented by compounds wherein A is halogen.

The most preferred class of compounds of formula (I) is represented by compounds wherein R is $(CH_2)p\text{-}COR1$ or $(CH_2)p\text{-}R1'$, wherein R1, R1' and p are as defined above.

Preferred specific compounds (cpd.) of the invention are listed below:

1. [3-(5-chloro-2,4-dihydroxyphenyl)-1,4,6,7-tetrahydro-5H-pyrazolo[4,3-c]pyridin-5-yl][4-(dimethylamino)phenyl]methanone,
2. [3-(5-chloro-2,4-dihydroxyphenyl)-1,4,6,7-tetrahydro-5H-pyrazolo[4,3-c]pyridin-5-yl](phenyl)methanone,
3. [3-(5-chloro-2,4-dihydroxyphenyl)-1,4,6,7-tetrahydro-5H-pyrazolo[4,3-c]pyridin-5-yl](4-nitrophenyl)methanone,
4. 1-[3-(5-chloro-2,4-dihydroxyphenyl)-1,4,6,7-tetrahydro-5H-pyrazolo[4,3-c]pyridin-5-yl]-2-[4-(methylsulfonyl)phenyl]ethanone,
5. [3-(5-chloro-2,4-dihydroxyphenyl)-1,4,6,7-tetrahydro-5H-pyrazolo[4,3-c]pyridin-5-yl][4-(hydroxymethyl)phenyl]methanone,
6. [3-(5-chloro-2,4-dihydroxyphenyl)-1,4,6,7-tetrahydro-5H-pyrazolo[4,3-c]pyridin-5-yl](thiophen-3-yl)methanone,
7. 4-{[3-(5-chloro-2,4-dihydroxyphenyl)-1,4,6,7-tetrahydro-5H-pyrazolo[4,3-c]pyridin-5-yl]carbonyl}benzonitrile,
8. [3-(5-chloro-2,4-dihydroxyphenyl)-1,4,6,7-tetrahydro-5H-pyrazolo[4,3-c]pyridin-5-yl](3-methoxyphenyl)methanone,
9. [3-(5-chloro-2,4-dihydroxyphenyl)-1,4,6,7-tetrahydro-5H-pyrazolo[4,3-c]pyridin-5-yl](4-methoxyphenyl)methanone,
10. [3-(5-chloro-2,4-dihydroxyphenyl)-1,4,6,7-tetrahydro-5H-pyrazolo[4,3-c]pyridin-5-yl][4-(methylsulfanyl)phenyl]methanone,
11. [3-(5-chloro-2,4-dihydroxyphenyl)-1,4,6,7-tetrahydro-5H-pyrazolo[4,3-c]pyridin-5-yl][4-(1H-pyrrol-1-yl)phenyl]methanone,
12. [3-(5-chloro-2,4-dihydroxyphenyl)-1,4,6,7-tetrahydro-5H-pyrazolo[4,3-c]pyridin-5-yl][4-(1,3-oxazol-5-yl)phenyl]methanone,
13. 4-{[3-(5-chloro-2,4-dihydroxyphenyl)-1,4,6,7-tetrahydro-5H-pyrazolo[4,3-c]pyridin-5-yl]carbonyl}benzenesulfonamide,
14. [3-(5-chloro-2,4-dihydroxyphenyl)-1,4,6,7-tetrahydro-5H-pyrazolo[4,3-c]pyridin-5-yl](1,4-dioxaspiro[4.5]dec-8-yl)methanone,
15. [3-(5-chloro-2,4-dihydroxyphenyl)-1,4,6,7-tetrahydro-5H-pyrazolo[4,3-c]pyridin-5-yl](tetrahydro-2H-pyran-4-yl)methanone,
16. [3-(5-chloro-2,4-dihydroxyphenyl)-1,4,6,7-tetrahydro-5H-pyrazolo[4,3-c]pyridin-5-yl][4-(1H-imidazol-1-yl)phenyl]methanone, 17. [3-(5-chloro-2,4-dihydroxyphenyl)-1,4,6,7-tetrahydro-5H-pyrazolo[4,3-c]pyridin-5-yl](trans-4-methoxycyclohexyl)methanone,
18. 4-chloro-6-{5-[3-(1H-imidazol-1-yl)benzyl]-4,5,6,7-tetrahydro-1H-pyrazolo[4,3-c]pyridin-3-yl}benzene-1,3-diol,
19. [3-(5-chloro-2,4-dihydroxyphenyl)-1,4,6,7-tetrahydro-5H-pyrazolo[4,3-c]pyridin-5-yl](1,5-dioxaspiro[5.5]undec-9-yl)methanone,
20. [3-(5-chloro-2,4-dihydroxyphenyl)-6,7-dihydroisoxazolo[4,3-c]pyridin-5(4H)-yl][4-(dimethylamino)phenyl]methanone,
21. 1-[3-(5-chloro-2,4-dihydroxyphenyl)-6,7-dihydroisoxazolo[4,3-c]pyridin-5(4H)-yl]-2-[4-(methylsulfonyl)phenyl]ethanone,
22. [3-(5-chloro-2,4-dihydroxyphenyl)-6,7-dihydroisoxazolo[4,3-c]pyridin-5(4H)-yl][4-(hydroxymethyl)phenyl]methanone,
23. [3-(5-chloro-2,4-dihydroxyphenyl)-6,7-dihydroisoxazolo[4,3-c]pyridin-5(4H)-yl](6-hydroxypyridin-3-yl)methanone,
24. 4-{[3-(5-chloro-2,4-dihydroxyphenyl)-6,7-dihydroisoxazolo[4,3-c]pyridin-5(4H)-yl]carbonyl}benzonitrile,
25. 4-{[3-(5-chloro-2,4-dihydroxyphenyl)-6,7-dihydroisoxazolo[4,3-c]pyridin-5(4H)-yl]carbonyl}benzenesulfonamide,
26. [3-(5-chloro-2,4-dihydroxyphenyl)-6,7-dihydroisoxazolo[4,3-c]pyridin-5(4H)-yl][2-(pyridin-3-yl)-1,3-thiazol-4-yl]methanone,
27. [3-(5-chloro-2,4-dihydroxyphenyl)-6,7-dihydroisoxazolo[4,3-c]pyridin-5(4H)-yl](4-nitrophenyl)methanone,
28. [3-(5-chloro-2,4-dihydroxyphenyl)-6,7-dihydroisoxazolo[4,3-c]pyridin-5(4H)-yl][4-(morpholin-4-yl)phenyl]methanone,
29. 1-[3-(5-chloro-2,4-dihydroxyphenyl)-6,7-dihydroisoxazolo[4,3-c]pyridin-5(4H)-yl]-2-[4-(hydroxymethyl)phenyl]ethanone,
30. [4-(aminomethyl)cyclohexyl][3-(5-chloro-2,4-dihydroxyphenyl)-6,7-dihydroisoxazolo[4,3-c]pyridin-5(4H)-yl]methanone,
31. [3-(5-chloro-2,4-dihydroxyphenyl)-6,7-dihydroisoxazolo[4,3-c]pyridin-5(4H)-yl](trans-4-methoxycyclohexyl)methanone,
32. 1-[3-(5-chloro-2,4-dihydroxyphenyl)-6,7-dihydroisoxazolo[4,3-c]pyridin-5(4H)-yl]-3-(morpholin-4-yl)propan-1-one,
33. [3-(5-chloro-2,4-dihydroxyphenyl)-6,7-dihydroisoxazolo[4,3-c]pyridin-5(4H)-yl][3-(1H-imidazol-1-yl)phenyl]methanone,
34. [3-(5-chloro-2,4-dihydroxyphenyl)-6,7-dihydroisoxazolo[4,3-c]pyridin-5(4H)-yl][4-(1H-imidazol-1-yl)phenyl]methanone,
35. [3-(5-chloro-2,4-dihydroxyphenyl)-6,7-dihydroisoxazolo[4,3-c]pyridin-5(4H)-yl][4-(1H-imidazol-1-ylmethyl)phenyl]methanone,
36. 4-chloro-6-{5-[4-(dimethylamino)benzyl]-4,5,6,7-tetrahydro-1H-pyrazolo[4,3-c]pyridin-3-yl}benzene-1,3-diol,
37. 4-chloro-6-(5-{[6-(morpholin-4-yl)pyridin-3-yl]methyl}-4,5,6,7-tetrahydro-1H-pyrazolo[4,3-c]pyridin-3-yl)benzene-1,3-diol,
38. 3-[3-(5-chloro-2,4-dihydroxyphenyl)-1,4,6,7-tetrahydro-5H-pyrazolo[4,3-c]pyridin-5-yl]-1-(morpholin-4-yl)propan-1-one,
39. 4-chloro-6-[5-(4-ethoxybenzyl)-4,5,6,7-tetrahydro-1H-pyrazolo[4,3-c]pyridin-3-yl]benzene-1,3-diol,
40. 4-chloro-6-[5-(3,4-dimethoxybenzyl)-4,5,6,7-tetrahydro-1H-pyrazolo[4,3-c]pyridin-3-yl]benzene-1,3-diol,
41. 4-chloro-6-{5-[3-(1H-1,2,4-triazol-1-yl)benzyl]-4,5,6,7-tetrahydro-1H-pyrazolo[4,3-c]pyridin-3-yl}benzene-1,3-diol,
42. 4-chloro-6-{5-[4-(1H-1,2,4-triazol-1-yl)benzyl]-4,5,6,7-tetrahydro-1H-pyrazolo[4,3-c]pyridin-3-yl}benzene-1,3-diol,
43. 4-chloro-6-(5-{4-[(2-hydroxyethyl)(methyl)amino]benzyl}-4,5,6,7-tetrahydro-1H-pyrazolo[4,3-c]pyridin-3-yl)benzene-1,3-diol,
44. 4-chloro-6-[5-(3-ethoxy-4-methoxybenzyl)-4,5,6,7-tetrahydro-1H-pyrazolo[4,3-c]pyridin-3-yl]benzene-1,3-diol,
45. 1-(4-{[3-(5-chloro-2,4-dihydroxyphenyl)-1,4,6,7-tetrahydro-5H-pyrazolo[4,3-c]pyridin-5-yl]methyl}phenyl)pyrrolidin-2-one,
46. 4-chloro-6-{5-[4-(morpholin-4-yl)benzyl]-4,5,6,7-tetrahydro-1H-pyrazolo[4,3-c]pyridin-3-yl}benzene-1,3-diol,
47. 4-chloro-6-(5-{[2-(morpholin-4-yl)pyridin-4-yl]methyl}-4,5,6,7-tetrahydro-1H-pyrazolo[4,3-c]pyridin-3-yl)benzene-1,3-diol,
48. 4-chloro-6-[5-(3-hydroxy-4-methoxybenzyl)-4,5,6,7-tetrahydro-1H-pyrazolo[4,3-c]pyridin-3-yl]benzene-1,3-diol,
49. 4-chloro-6-{5-[4-(1H-1,2,3-triazol-1-yl)benzyl]-4,5,6,7-tetrahydro-1H-pyrazolo[4,3-c]pyridin-3-yl}benzene-1,3-diol,
50. 4-chloro-6-{5-[4-(1H-imidazol-1-yl)benzyl]-4,5,6,7-tetrahydro-1H-pyrazolo[4,3-c]pyridin-3-yl}benzene-1,3-diol,
51. 4-chloro-6-{5-[3-(1H-imidazol-1-yl)benzyl]-4,5,6,7-tetrahydro-1H-pyrazolo[4,3-c]pyridin-3-yl}benzene-1,3-diol,
52. 4-chloro-6-{5-[4-(dimethylamino)benzyl]-4,5,6,7-tetrahydroisoxazolo[4,3-c]pyridin-3-yl}benzene-1,3-diol,
53. 4-chloro-6-(5-{[6-(morpholin-4-yl)pyridin-3-yl]methyl}-4,5,6,7-tetrahydroisoxazolo[4,3-c]pyridin-3-yl)benzene-1,3-diol,
54. 4-chloro-6-{5-[3-(1H-imidazol-1-yl)benzyl]-4,5,6,7-tetrahydroisoxazolo[4,3-c]pyridin-3-yl}benzene-1,3-diol,
55. 4-[3-(5-chloro-2,4-dihydroxyphenyl)-6,7-dihydroisoxazolo[4,3-c]pyridin-5(4H)-yl]butan-2-one,
56. 4-chloro-6-[5-(pyridin-4-ylmethyl)-4,5,6,7-tetrahydroisoxazolo[4,3-c]pyridin-3-yl]benzene-1,3-diol,
57. 4-chloro-6-(5-{[5-(hydroxymethyl)furan-2-yl]methyl}-4,5,6,7-tetrahydroisoxazolo[4,3-c]pyridin-3-yl)benzene-1,3-diol,
58. 4-{[3-(5-chloro-2,4-dihydroxyphenyl)-6,7-dihydroisoxazolo[4,3-c]pyridin-5(4H)-yl]methyl}benzonitrile,
59. 4-chloro-6-[5-(4-ethoxybenzyl)-4,5,6,7-tetrahydroisoxazolo[4,3-c]pyridin-3-yl]benzene-1,3-diol,
60. 4-chloro-6-[5-(3-hydroxy-4-methoxybenzyl)-4,5,6,7-tetrahydroisoxazolo[4,3-c]pyridin-3-yl]benzene-1,3-diol,
61. 4-chloro-6-[5-(3,4-dimethoxybenzyl)-4,5,6,7-tetrahydroisoxazolo[4,3-c]pyridin-3-yl]benzene-1,3-diol,
62. 4-chloro-6-(5-{[2-(morpholin-4-yl)-1,3-thiazol-5-yl]methyl}-4,5,6,7-tetrahydroisoxazolo[4,3-c]pyridin-3-yl)benzene-1,3-diol,
63. 4-chloro-6-{5-[3-(morpholin-4-yl)propyl]-4,5,6,7-tetrahydroisoxazolo[4,3-c]pyridin-3-yl}benzene-1,3-diol,
64. 4-chloro-6-{5-[3-(1H-1,2,4-triazol-1-yl)benzyl]-4,5,6,7-tetrahydroisoxazolo[4,3-c]pyridin-3-yl}benzene-1,3-diol,
65. 1-(4-{[3-(5-chloro-2,4-dihydroxyphenyl)-6,7-dihydroisoxazolo[4,3-c]pyridin-5(4H)-yl]methyl}phenyl)pyrrolidin-2-one, 66. 4-chloro-6-{5-[4-(morpholin-4-yl)benzyl]-4,5,6,7-tetrahydroisoxazolo[4,3-c]pyridin-3-yl}benzene-1,3-diol,
67. 4-chloro-6-{5-[4-(1H-imidazol-1-yl)benzyl]-4,5,6,7-tetrahydroisoxazolo[4,3-c]pyridin-3-yl}benzene-1,3-diol,
68. 3-[3-(5-chloro-2,4-dihydroxyphenyl)-6,7-dihydroisoxazolo[4,3-c]pyridin-5(4H)-yl]-1-(morpholin-4-yl)propan-1-one and
69. 4-chloro-6-(5-{[2-(morpholin-4-yl)pyridin-4-yl]methyl}-4,5,6,7-tetrahydroisoxazolo[4,3-c]pyridin-3-yl)benzene-1,3-diol.

The present invention also provides a process for the preparation of a compound of formula (I) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-exemplified compounds according to the invention may be performed by modifications apparent to those skilled in the art, for instance by appropriately protecting interfering groups, by changing to other suitable reagents known in the art, or by making routine modifications of reaction conditions. Alternatively other reactions referred to herein or known in the art will be recognized as having adaptability for preparing other compounds of the invention.

The present invention also provides a process for the preparation of a compound of formula $(I)_A$ as defined above, characterized in that the process comprises:

a) condensing a compound of formula (2):

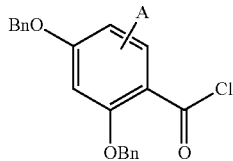

(2)

wherein Bn is benzyl and A is as defined above, with a compound of formula (3):

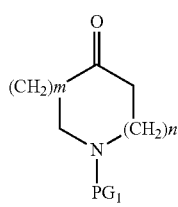

(3)

wherein $PG_1$ is an N protecting group such as benzyl or tert-butyloxycarbonyl and m and n are as defined above;

b) condensing the resultant compound of formula (4):

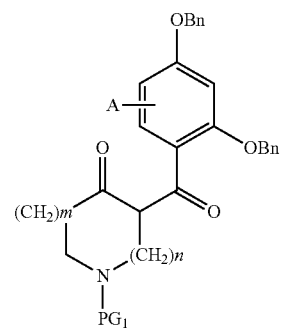

(4)

wherein Bn, A, $PG_1$, m and n are as defined above, with hydrazine hydrate or an hydrazine salt;

c1) either reducing the resultant compound of formula (5):

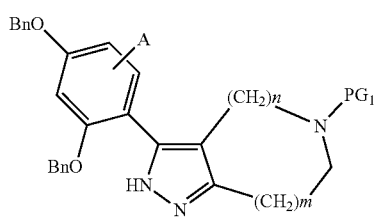

(5)

wherein Bn, A, m and n are as defined above and $PG_1$ is benzyl, with $H_2$ and a suitable catalyst, to give a compound of formula $(I)_A$:

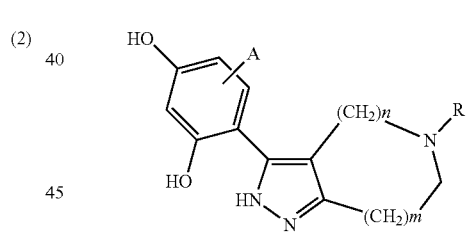

$(I)_A$ wherein A, m and n are defined above and R is hydrogen;
or
c2) removing the $PG_1$, wherein $PG_1$ is tert-butyloxycarbonyl, from the compound of formula (5) as defined above, with hydrochloric, trifluoroacetic, methanesulfonic or formic acid;

d) reducing the resultant compound of formula (6):

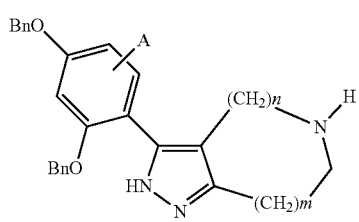

(6)

wherein Bn, A, m and n are as defined above, with H$_2$ and a suitable catalyst, to give a compound of formula (I)$_A$ as defined above, wherein R is hydrogen;

or c3) reducing the compound of formula (5) as defined above, wherein PG$_1$ is tert-butyloxycarbonyl, with H$_2$ and a suitable catalyst, to give a compound of formula (I)$_A$:

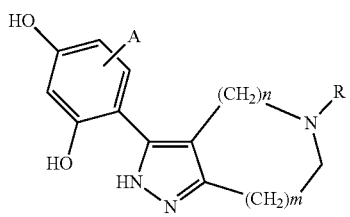

(I)$_A$ wherein A, m and n are as defined above and R is tert-butyloxycarbonyl;

e) optionally removing the tert-butyloxycarbonyl from the resultant compound of formula (I)$_A$ wherein R is tert-butyloxycarbonyl, with hydrochloric, trifluoroacetic, methanesulfonic or formic acid, to give a compound of formula (I) wherein R is hydrogen, if necessary or wanted after any of the above steps, separating the optionally obtained mixture of the regioisomers into the single isomers.

The present invention also provides a process for the preparation of a compound of formula (I)$_B$ as defined above, characterized in that the process comprises:

f1) either reducing a compound of formula (4) as defined above, with H$_2$ and a suitable catalyst, to give a compound of formula (7):

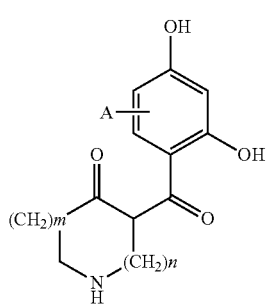

(7)

wherein A, m and n are as defined above;

or f2) removing the PG$_1$ from a compound of formula (4) wherein PG$_1$ is tert-butyloxycarbonyl with hydrochloric, trifluoroacetic, methanesulfonic or formic acid;

g) reducing the resultant compound of formula (8):

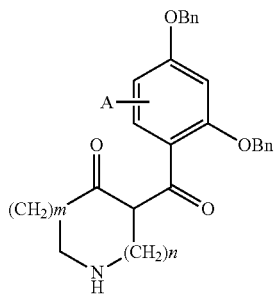

(8)

wherein A, Bn, m and n are as defined above, with H$_2$ and a suitable catalyst;

h) condensing the resultant compound of formula (7):

(7)

wherein A, m and n are as defined above, with NH$_2$OH.HCl or NH$_2$OH.H$_2$SO$_4$ in presence of an organic base, to give a compound of formula (I)$_B$:

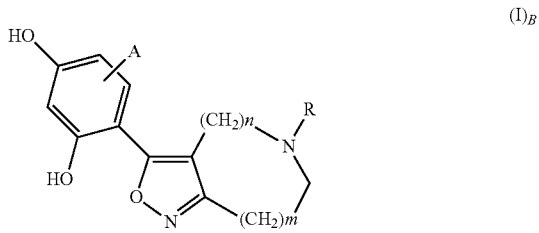

(I)$_B$ wherein A, m and n are as defined above and R is hydrogen;

or f3) reducing a compound of formula (4) wherein PG$_1$ is tert-butyloxycarbonyl with H$_2$ and a suitable catalyst;

i) condensing the resultant compound of formula (9):

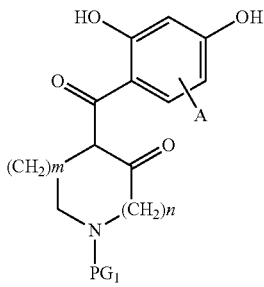 (9)

wherein PG₁ is tert-butoxycarbonyl and A, m and n are as defined above, with NH₂OH.HCl or NH₂OH.H₂SO₄ in presence of an organic base, to give a compound of formula (I)$_B$:

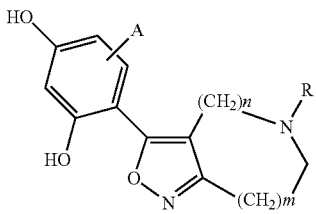 (I)$_B$ wherein R is tert-butyloxycarbonyl and a, m and n are as defined above;
j) optionally removing the tert-butyloxycarbonyl from the resultant compound of formula (I)$_B$ wherein R is tert-butyloxycarbonyl, with hydrochloric, trifluoroacetic, methanesulfonic or formic acid, to give a compound of formula (I)$_B$ wherein R is hydrogen, if necessary or wanted after any of the above steps separating the optionally obtained mixture of the regioisomers into the single isomers.

The present invention also provides a process for the preparation of a compound of formula (I) as defined above, characterized in that the process comprises:
k) condensing a compound of formula (I) prepared as defined above:

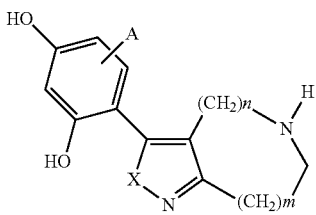 (I)

wherein A, X, m and n are as defined above, according to any one of the alternative steps:
k1) with a compound of formula (10):

R1COW (10)

wherein R1 is as defined above, and W is OH or an activated group such as chlorine, 1-imidazolyl, 1-succinimidyloxy, 1-hydroxybenzotriazolyl or O-isoureyl, to give a compound of formula (I):

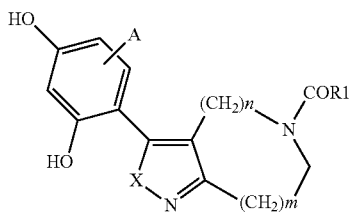 (I)

wherein A, X, m, n, and R1 are as defined above;
k2) with a compound of formula (11):

R1'OCOHal (11)

wherein Hal is halogen and R1' is as defined above, to give a compound of formula (I):

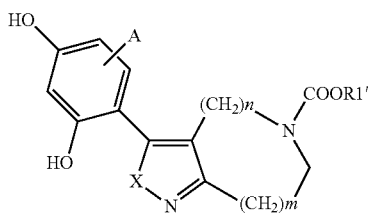 (I)

wherein A, X, m, n, and R1' are as defined above;
k3) with a compound of formula (12):

R1'N=Z (12)

wherein R1' and Z are as defined above, to give a compound of formula (I):

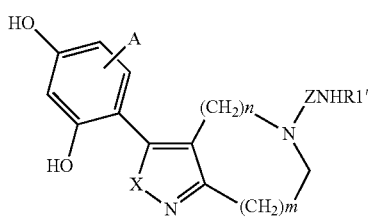 (I)

wherein A, X, m, n, and R1' are as defined above;
k4) with a compound of formula (13):

R1'(CH₂)$_{p-1}$CHO (13)

wherein R1' and p are as defined above, to give a compound of formula (I):

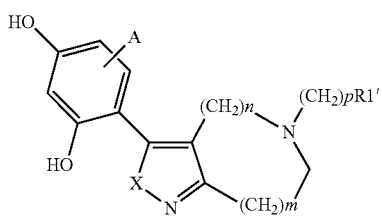 (I)

wherein A, X, m, n, p and R1' are as defined above;

k5) with a compound of formula (14):

R1'COR1' (14)

wherein R1' the same or different are as defined above or taken together may form an optionally substituted cycloalkyl or heterocyclyl containing one or more heteroatom selected from S, O or N to give a compound of formula (I):

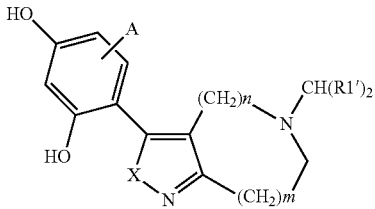
(I)

wherein A, X, m, n, and R1' are as defined above;
k6) with a compound of formula (15):

R2SO$_2$Hal (15)

wherein Hal is halogen and R2 is as defined above, to give a compound of formula (I):

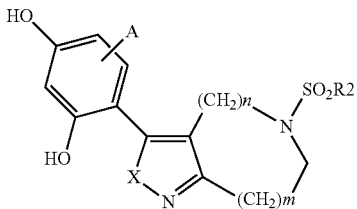
(I)

wherein A, X, m, n, and R2 are as defined above;
k7) with a compound of formula (16):

R1"Hal (16)

wherein Hal is halogen and R1" is optionally substituted ($C_1$-$C_6$) alkyl or aryl, such as phenyl with an electron withdrawing group such as nitro, cyano or methylsulfonyl in ortho or para position to the halogen, or heteroaryl such as pyridine, pyrimidine, pyrazine, pyridazine, quinoline or isoquinoline with the halogen in ortho or para position to one of the nitrogen, to give a compound of formula (I):

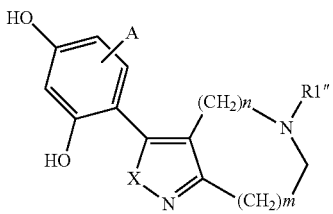
(I)

wherein A, X, m, n, and R1" are as defined above;
or
k8) with a compound of formula (17):

CH$_2$=CHCOR1' (17)

wherein R1' is defined as above, to give a compound of formula (I):

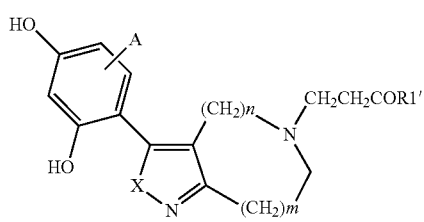
(I)

wherein A, X, m, n, and R1' are as defined above;
optionally separating the resultant compound of formula (I) into the single isomers, and/or converting it into another derivative of formula (I) and or into a pharmaceutically acceptable salt.

According to step a), the reaction of a compound of formula (2) with a compound of formula (3) to give a compound of formula (4) can be accomplished in a variety of ways and experimental conditions, according to conventional methods, which are widely known in the literature. Preferably the reaction is carried out in presence of an organic base such as lithium bis(trimethylsilyl)amide or sodium bis(trimethylsilyl)amide in a suitable solvent such as, for instance, tetrahydrofuran or diethylether, at a temperature ranging from −45° C. to room temperature and for a time varying from about one h to 6 h (Tele, 2002, 44, 1067; Synthesis, 1991, 17, 3).

According to step b), the reaction of a compound of formula (4) with hydrazine can be carried out in a variety of ways, according to conventional methods, which are widely known in the literature. Preferably it is carried out using hydrazine hydrate, hydrazine hydrochloride or hydrazine sulfate and in presence of a base such as TEA or DIPEA, or an organic or inorganic salt such as sodium acetate, potassium acetate or sodium carbonate, in a suitable solvent such as, for instance, methanol, ethanol, tetrahydrofurane, pyridine or acetic acid, at a temperature ranging from 80° C. to 130° C. and for a time varying from 2 h to overnight. (Tele, 1993, 34, 8305; J. Med. Chem., 2004, 47 (20), 4798; Organic Letters, 2006, 8(13), 2675).

When a mixture of regioisomeric compounds is obtained in step a or b, i.e. the resultant compounds of formula (4) or (5) are characterized by different values of m and n, it can be conveniently separated into the single isomers and purified by known methods such as silica gel chromatography, preparative HPLC or crystallization.

It is known to the skilled person that conversion of a chemical function into another may require that one or more reactive centers in the compound containing this function be protected in order to avoid undesired side reactions. Protection of such reactive centers, and subsequent deprotection at the end of the synthetic transformations, can be accomplished following standard procedures described, for instance, in: Green, Theodora W. and Wuts, Peter G. M.—Protective Groups in Organic Synthesis, Third Edition, John Wiley & Sons Inc., New York (N.Y.), 1999.

According to step c1,) the reaction of a compound of formula (5) wherein PG$_1$ is benzyl to give a compound of formula (I)$_A$ wherein R is hydrogen, can be accomplished in a variety of ways and experimental conditions, according to conventional methods, which are widely known in the literature, preferably the catalytic hydrogenation is carried out in a solvent such as methanol, ethanol, ethyl acetate or acetic acid, in a range of temperature ranging from 25° C. to 100° C., under a hydrogen pressure ranging from 1 to 30 atm and employing Pt/C or Pt/C as catalysts (J.A.C.S., 1978, 93, 746) and for a time ranging from 1 to 10 h. Alternatively, the hydrogenation can be carried out under transfer hydrogen condition by using cyclohexene or cyclohexadiene as hydrogen source, in a solvent such as ethanol or methanol, and Pt/C as catalyst, in a range of temperature from room temperature to 60° C. (J. Org. Chem., 1978, 43, 4194).

According to step c2), the reaction of a compound of formula (5) wherein $PG_1$ is tertbutyloxycarbonyl to give a compound of formula (6) can be accomplished in a variety of ways and experimental conditions, according to conventional methods, which are widely known in the literature, preferably it is conducted by reaction with organic or inorganic acids such as formic acid, trifluoroacetic acid, methanesulfonic acid or hydrochloric acid, in a solvent such as methanol, ethanol, ethyl acetate, tetrahydrofurane or dioxane, in a range of temperature from 0 to 50° C. (J.A.C.S., 1978, 93, 746).

The steps d) and c3) are accomplished in the conditions described for step c1).

The step e) is accomplished in the conditions described for step c2).

The step f1) is accomplished in the conditions described for step c1).

The step f2) is accomplished in the conditions described for step c2).

The steps g) is accomplished in the conditions described for step c1).

According to step h), the reaction of a compound of formula (7) with $NH_2OH.HCl$ or $NH_2OH.H_2SO_4$ can be accomplished in a variety of ways and experimental conditions, according to conventional methods, which are widely known in the literature. Preferably, the reaction is carried out in a solvent such as ethanol, methanol, tetrahydrofurane, acetic acid, pyridine and of a base such as TEA, DIPEA, or an organic or inorganic salt such as sodium acetate, potassium acetate, sodium carbonate when are necessary in a range of temperature from 50° C. to 150° C. (A. Quilico, G. Speroni, L. Behr, R. L. McKee, The Chemistry of Heterocyclic Compounds—Vol. 17—John Wiley & Sons Inc., New York (N.Y.), 1962).

The step f3) is accomplished in the conditions described for step c1).

The step i) is accomplished in the conditions described for step h).

The step j) is accomplished in the conditions described for step c2).

According to step k), the reaction of a compound of formula (I) wherein R is hydrogen to give a compound of formula (I) wherein R is defined as above can be accomplished in a variety of ways and experimental conditions, according to conventional methods, which are widely known in the literature.

According to step k1) a compound of formula R1COOH is converted into its corresponding acyl chloride in the presence of thionyl chloride or oxalyl chloride and a catalytic amount of DMF, in a suitable solvent such as toluene, dichloromethane, chloroform, diethyl ether, tetrahydrofuran or 1,4-dioxane, at a temperature ranging from about −10° C. to reflux and for a period of time varying from about 1 h to about 12 h. The acyl chloride is isolated by evaporation of the solvent and further reacted with a compound of formula (I) wherein R is hydrogen in the presence of a base such a pyridine, triethylamine or N-ethyldiisopropylamine in a suitable solvent, such as toluene, dichloromethane, chloroform, diethyl ether, tetrahydrofuran, 1,4-dioxane, at a temperature ranging from about −40° C. to reflux and for a period of time varying from about 1 h to about 96 h. Alternatively, a compound of formula R1COOH is reacted with a compound of formula (I) wherein R is hydrogen in the presence of an activating agent such as N,N'-carbonyldiimidazole, 2-(1H-7-azabenzotriazol-1-yl)-1,1,3,3-tetramethyl uronium hexafluorophosphate methanaminium, O-benzotriazole-N, N,N',N'-tetramethyl-turonium-hexafluoro-phosphate, dicyclohexyl carbodiimide, diisopropyl carbodiimide or 1-ethyl-3-(3'-dimethylamino)carbodiimide hydrochloric acid salt and optionally in the presence of hydroxybenzotriazole. Preferably, this reaction is carried out in a suitable solvent such as, for instance, tetrahydrofuran, dichloromethane, chloroform, toluene, 1,4-dioxane, and in the presence of a proton scavenger such as, for example, pyridine, triethylamine, N,N-diisopropylethylamine, at a temperature ranging from room temperature to reflux, for a time ranging from about 30 min. to about 24 h.

According to step k2), the reaction of a compound of formula R1'OCOCl with a compound of formula (I) wherein R is hydrogen, can be accomplished in a variety of ways and experimental conditions, according to conventional methods, which are widely known in the literature. Preferably the reaction is carried out in the presence of a base such a pyridine, triethylamine or N-ethyldiisopropylamine in a suitable solvent, such as toluene, dichloromethane, chloroform, diethyl ether, tetrahydrofuran, 1,4-dioxane, at a temperature ranging from about −40° C. to 70° C. and for a period of time varying from about 1 hour to about 24 h.

According to step k3), the reaction of a compound of formula R1'N=Z with a compound of formula (I) wherein R is hydrogen, can be accomplished in a variety of ways and experimental conditions, according to conventional methods, which are widely known in the literature. Preferably the reaction is carried out in the presence of a base such a triethylamine, DIPEA or pyridine and in a suitable solvent, such as toluene, dichloromethane, chloroform, tetrahydrofuran or 1,4-dioxane, at a temperature ranging from rt to 100° C. and for a period of time varying from 1 to 12 h.

According to step k4), the reaction of a compound of formula R1'($CH_2$)p-$_1$CHO with a compound of formula (I) wherein R is hydrogen, can be accomplished in a variety of ways and experimental conditions, according to conventional methods, which are widely known in the literature. Preferably the reaction is carried out in the presence of a reducing agent such as sodium borohydride, sodium cyanoborohydride, sodium triacetoxyborohydride, tetrabutylammonium borohydride in a solvent such as methanol, ethanol, acetonitrile, tetrahydrofurane, dioxane, dichloromethane, chloroform, and in presence of an acid such a hydrochloric, acetic, methanesulfonic, trifluoroacetic acid in order to reach a range of pH varying from 2 to 5 and at a temperature ranging from 0° C. to 75° C. and for a period of time varying from 1 to 12 h.

The step k5) is accomplished in the conditions described for step k4) at higher temperature and longer reaction time.

According to step k6), the reaction of a compound of formula R2SO₂Cl with a compound of formula (I) wherein R is hydrogen, can be accomplished in a variety of ways and experimental conditions, according to conventional methods, which are widely known in the literature. Preferably the reaction is carried out in the presence of a base such a triethylamine, DIPEA, pyridine, imidazole in a suitable solvent, such as dichloromethane, chloroform, tetrahydrofuran, 1,4-dioxane, pyridine, ethyl acetate at a temperature ranging from −15° C. to 75° C. and for a period of time varying from 1 to 24 h.

According to step k7), the reaction of a compound of formula R1″Hal with a compound of formula (I) wherein R is hydrogen, can be accomplished in a variety of ways and experimental conditions, according to conventional methods, which are widely known in the literature. Preferably the reaction is carried out in the presence of a base such sodium carbonate, cesium carbonate, potassium carbonate, in a suitable solvent, such as dimethylformamide, N-methylpirrolidinone, tetramethylurea, dimethylsulfoxide and in presence of a catalyst such as $Cu_2Cl_2$, $Cu_2I_2$, L-proline when is required, at a temperature ranging from 75° C. to 150° C. and for a period of time varying from 1 to 12 h.

According to step k8), the reaction of a compound of formula $CH_2=CHCOR1'$ with a compound of formula (I) wherein R is hydrogen, can be accomplished in a variety of ways and experimental conditions, according to conventional methods, which are widely known in the literature. Preferably the reaction is carried out in a suitable solvent, such as dimethylformamide, N-methylpirrolidinone, THF, dimethylsulfoxide, DCM, $CHCl_3$, at a temperature ranging from 0° C. to 100° C. and for a period of time varying from 1 to 24 hours.

In cases where a compound of formula (I) contains one or more asymmetric centers, said compound can be separated into the single isomers by procedures known to those skilled in the art. Such procedures comprise standard chromatographic techniques, including chromatography using a chiral stationary phase, or crystallization. General methods for separation of compounds containing one or more asymmetric centers are reported, for instance, in Jacques, Jean; Collet, André; Wilen, Samuel H.,—Enantiomers, Racemates, and Resolutions, John Wiley & Sons Inc., New York (N.Y.), 1981.

A compound of formula (I) wherein R is as defined above but not hydrogen, can also be further converted into a different compound of formula (I) wherein R has a different meaning among those defined above. Examples of possible reactions for such conversion are:
1) hydrolysis under acid or basic condition of alkoxycarbonyl derivatives for conversion into the corresponding carboxylic acid derivatives, according to standard procedures as reported in The Chemistry of Carboxylic Acids and Esters, Saul Patai, Interscience Publisher (John Wiley & Sons 1969);
2) amidation of carboxylic acid derivatives for conversion into the corresponding amides under the conditions described in the step k1;
3) amidation of alkoxycarbonyl derivatives for conversion into the corresponding amides by direct reaction with a suitable primary or secondary amines according to standard procedures as reported in The Chemistry of Amides, Saul Patai, Interscience Publisher (John Wiley & Sons 1970);
4) reduction of amides derivatives for conversion into the corresponding amines according to standard procedures as reported in The Chemistry of Amino Group, Saul Patai, Interscience Publisher (John Wiley & Sons 1968);
5) ketalization of carbonyl derivatives for conversion into the corresponding ketales according to standard procedures as reported in The Chemistry of Carbonyl Group, Saul Patai, Interscience Publisher (John Wiley & Sons 1966).

A compound of formula (I) can also be transformed into a pharmaceutically acceptable salt according to standard procedures that are known to those skilled in the art. Alternatively, a compound of formula (I) that is obtained as a salt can be transformed into the free base or the free acid according to standard procedures that are known to the skilled person.

The synthesis of a compound of formula (I), according to the synthetic process described above, can be conducted in a stepwise manner, whereby each intermediate is isolated and purified by standard purification techniques, like, for example, column chromatography, before carrying out the subsequent reaction. Alternatively, two or more steps of the synthetic sequence can be carried out in a so-called "one-pot" procedure, as known in the art, whereby only the compound resultant from the two or more steps is isolated and purified.

The synthesis of the compounds of formula (I) is summarized in the following Schemes I and II, wherein Bn, A, X, $PG_1$, m, n and R are as defined above.

Scheme I

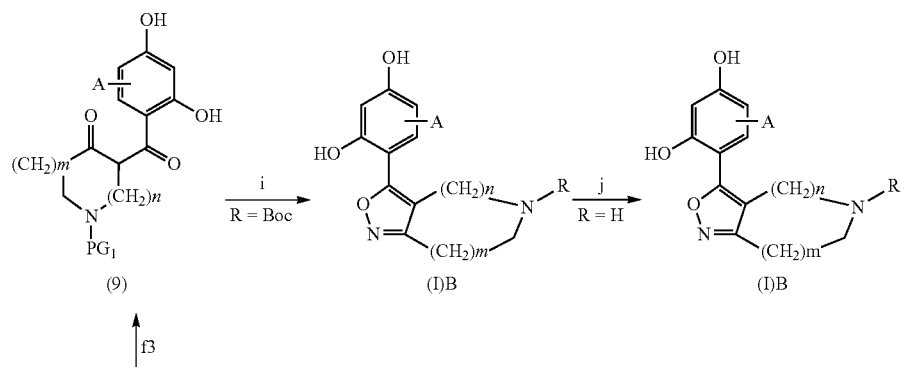

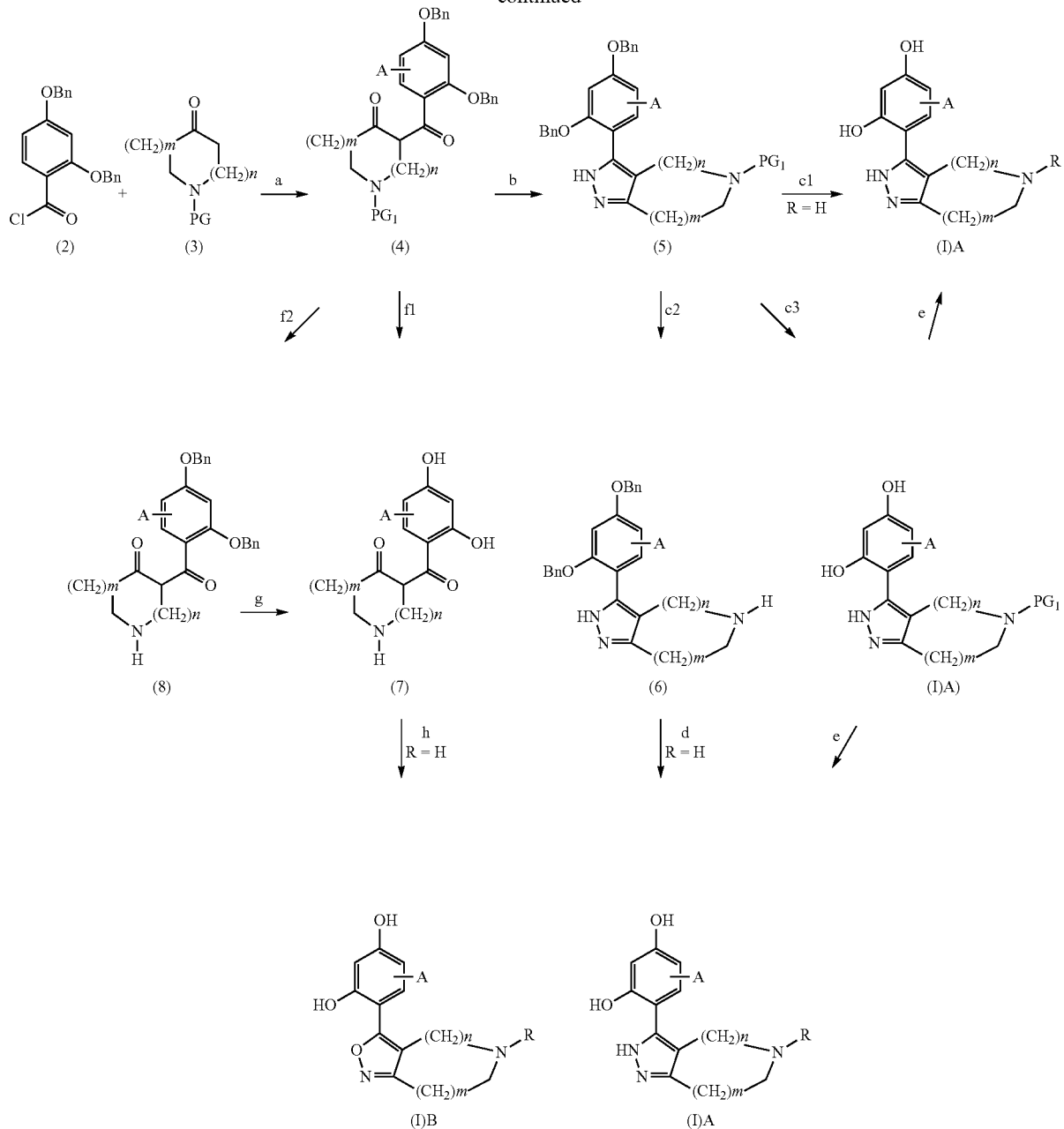
Scheme II
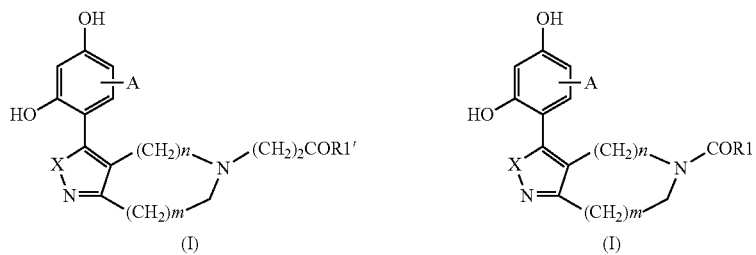

-continued

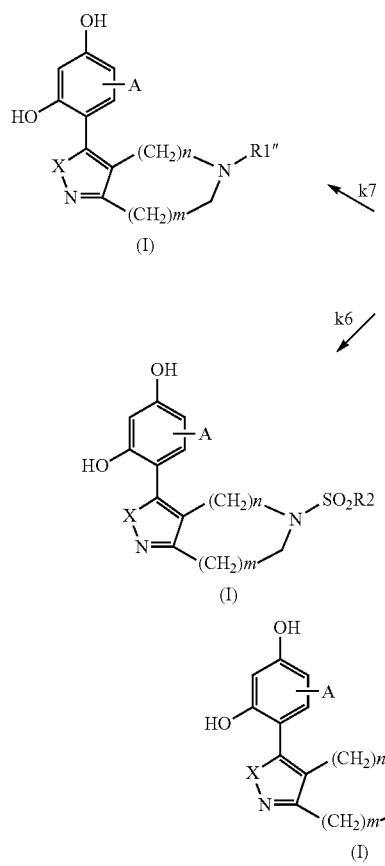

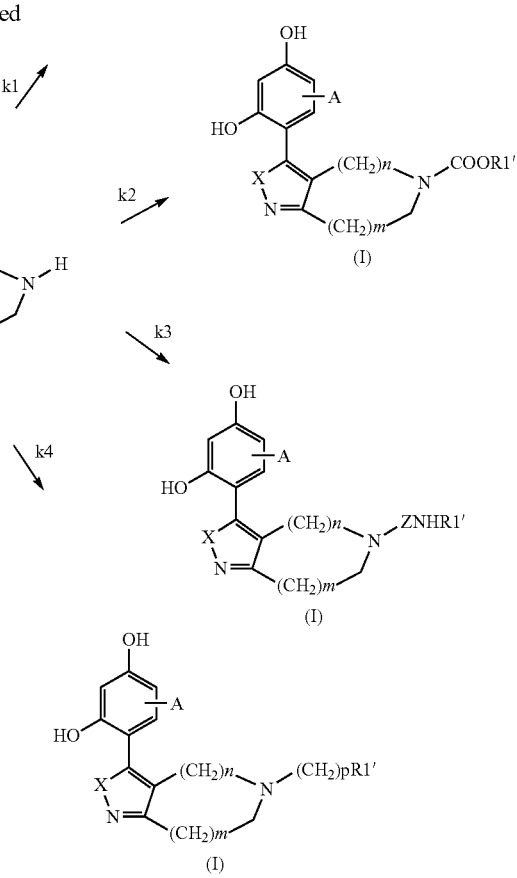

The starting material of the process of the invention, i.e. the compound of formula (2) is prepared as described in J. Org. Chem. (2006), 71(20), 7618-7631, Organic Letters (2005), 7(11), 2157-2160.

The starting materials of the process of the present invention, i.e. compounds of formula (3) are commercially available.

Compounds of formula (10) are either commercially available or can be prepared as described in step k1).

Compounds of formula (11), (12), (13), (14), (15), (16) and (17) are either commercially available or can be prepared by using well-known methods, such as those reported in Advance Organic Chemistry, Reactions, Mechanisms, and Structure, Jerry March, Fourth edition, Interscience Publisher (John Wiley & Sons 1992).

Pharmacology

The potency of the compounds of formula (I) were evaluated by measuring the Her2 degradation as a marker for Hsp90 inhibition.

Hsp90 is a key component of a chaperone machinery that catalyzes the folding and quality control of several proteins. Its inhibition impairs the capacity to fold or stabilize its client proteins, leading to the proteosomal dependent degradation of these unfolded proteins. At the moment there is an increasing number (>100) of reported Hsp90 clients, but one of the most frequently way to detect Hsp90 chaperone inhibition is the detection of Her2 protein levels after short time treatment (usually 8-24 h), in order to be sure about the specificity of this effect.

Assay

Cellular activity of Hsp90 inhibitors was assessed by measuring the induced loss of Her2 protein levels in BT474 breast cancer cells (ATCC #HTB-20). Cellular Her2 levels were measured by immunocytochemistry, and quantified using an ArrayScan vTi instrument (Cellomics Thermo Scientific).

Studies were performed as follows: 5000 cells/well are seeded in 96 well plates (Perkin Elmer) in DMEM/5% FCS and incubated for 48 h at 37° C., under 5% $CO_2$.

Medium is then replaced with fresh medium containing test compounds at the required concentration. Concentration curves are prepared in DMEM/10% FCS from compound stocks in DMSO, and final DMSO concentration is 0.1% (v/v). Duplicate wells for each concentration point are prepared, with a typical highest compound concentration of 30 μM. After addition of compound, plates are returned to the incubator for 8 h, then fixed by replacing medium with PBS containing 3.7% paraformaldehyde solution. Plates are incubated for 20 minutes at room temperature, then wells are washed in PBS and cells permiabilised by incubating with PBS containing 0, 3% Triton X-100 for 15 minutes at room temperature. Non-specific binding sites are blocked by incubating wells for 1 h in PBS containing 3% (w/v) BSA. Wells are then incubated for 1 h at room temperature in PBS containing anti Her2 mouse monoclonal (Anti-c-ErbB2/c-Neu, Mouse mAb 3B5, Calbiochem Cat No OP15) diluted 1:100 in 1% (w/v) BSA. After 3 washes in PBS, wells are incubated in PBS (w/v) 1% BSA containing a 2 μg/ml of Cy2-conjugated Goat anti mouse secondary antibody (Amersham Pharmacia Biothech cat. No PA 42002) (Absorption maximum 489 nm fluorescence maximum 506 nm) and 1 μg/ml of DAPI (Absorption maximum 359 nm fluorescence maximum 461 nm) (4',6-Diamidino-2-phenylindole, dilactate) (Sigma cat. No D 9564) a high sensitivity dye to detect nucleid acid for nuclear staining. After washing a further 3 times in PBS, cellular Her2 immunoreactivity is assessed using the ArrayScan vTi instrument, with a Zeiss 10×0.5 N.A. objective, and applying the Cytotoxity.V3 algorithm (Cellomics/Thermo Fisher) with a XF100 filter. At least 10 fields, corresponding to at least 900 cells, are read for each well. IC50 values represent the compound concentration at which cellular Her2 signal is diminished by 50% compared with untreated controls.

The following formula is used:

$$IC_{50}=Bottom+(Top-Bottom)/(1+10^{((Log\ EC_{50}-X))});$$

X is the logarithm of concentration. $IC_{50}$ is the response; $IC_{50}$ starts at Bottom and goes to Top with a sigmoid shape. The compounds of formula (I) tested as described above, result to induce the degradation of Her2 protein. Given the above assay, the compounds of formula (I) result to possess a remarkable Hsp90 inhibitory activity, as proven by the induction of the Her2 protein degradation, as shown in the following Table 1.

TABLE I

| Comp. No. | Her2 degradation BT474 cells $IC_{50}$ (microM) |
|---|---|
| 67 | 8.7 |
| 14 | 1.1 |
| 16 | 8.3 |
| 17 | 3.0 |
| 40 | 4.0 |
| 49 | 3.4 |

According to the biological data obtained, the compounds of formula (I) are good Hsp90 inhibitors and are therefore particularly advantageous in the therapy of cancer and neurodegenerative diseases.

The compounds of the present invention can be administered either as single agents or, alternatively, in combination with known anticancer treatments such as radiation therapy or chemotherapy regimen in combination with, for example, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, and conditions of the patient and administration route.

For example, a suitable dosage adopted for oral administration of a compound of formula (I) may range from about 10 to about 1 g per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions.

As an example the syrups may contain, as a carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

EXPERIMENTAL SECTION

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

Analytical Method 1:

Analyses were performed on a Waters Acquity UPLC™ System equipped with a 2996 PDA (UV-VIS), and Acquity ELSD™ detectors. The LC system was coupled to a Waters Acquity 3100 SQD™ single quadrupole mass spectrometer for atomic mass determinations. A Waters Acquity UPLC™

BEH C18, 1.7 μm, 2.1×50 mm column at 45° C. was used with a flow rate of 0.7 mL/min of the following binary solvent system and gradient.

Mobile Phase A: 0.1% Trifluoracetic Acid in $H_2O$/Acetonitrile (95:5)

Mobile Phase B: Acetonitrile/$H_2O$ (95:5)

| Time (min) | Phase A | Phase B |
| --- | --- | --- |
| 0.00 | 95% | 5% |
| 2.00 | 5% | 95% |

Analytical Method 2:

Analyses were performed on a Waters Alliance HT 2795 System equipped with a 996 PDA (UV-VIS), and S.E.D.E.R.E. SEDEX 55, ELSD, detectors. The LC system was coupled to a Waters/Micromass ZQ™ single quadrupole mass spectrometer for atomic mass determinations. A Waters Atlantis dC18, 3 μm, 4.6×50 mm column was used with a flow rate of 1.4 mL/min of the following binary solvent system and gradient.

Mobile Phase A: Ammonium Acetate 5 mM/Acetonitrile (95:5)—pH 5.2

Mobile Phase B: Acetonitrile/$H_2O$ (95:5)

| Time (min) | % Phase A | % Phase B |
| --- | --- | --- |
| 0.00 | 95% | 5% |
| 3.00 | 25% | 75% |
| 3.10 | 0% | 100% |

Analytical Method 3:

Analyses were performed on a Waters Alliance HT 2795 System equipped with a 996 PDA (UV-VIS) detector. The LC system was coupled to a Waters/Micromass ZQ™ single quadrupole mass spectrometer for atomic mass determinations. A Waters Ascentis Express C18, 2.7 μm, 4.6×50 mm column was used with a flow rate of 1.0 mL/min of the following binary solvent system and gradient.

Mobile Phase A: 0.1% Trifluoracetic Acid in $H_2O$/Acetonitrile (95:5)

Mobile Phase B: Acetonitrile/$H_2O$ (95:5)

| Time (min) | % Phase A | % Phase B |
| --- | --- | --- |
| 0.00 | 90% | 10% |
| 4.00 | 10% | 90% |
| 4.10 | 0% | 100% |

Mass Spectrometer Parameters: (Method 1)

Exact mass data ESI(+) were obtained on a Waters Q-T of Ultima directly connected with micro HPLC 1100 Agilent as previously described[19].

[19] M. Colombo, F. Riccardi-Sirtori, V. Rizzo, Rapid Commun. Mass Spectrom. 2004, 18, 511-517.

| Ionization Mode | ESI+ and ESI− |
| --- | --- |
| Capillary Voltage | 3 kV (ES+); 3 kV (ES−) |
| Cone Voltage | 30 V (ES+); 30 V (ES−) |
| Extractor Voltage | 1 V |
| RF Lens Voltage | 0.1 V |
| Source Temperature | 120° C. |
| Desolvation Temperature | 350° C. |
| Cone Gas Flow | 100 L/Hr |
| Desolvation Gas Flow | 600 L/Hr |
| LM Resolution | 15.0 |
| HM Resolution | 15.0 |
| Ion Energy | 0.3 |
| Gain | 1 |
| Scan Mode | Full Scan (Range = 100-800 m/z) ScanTime = 0.1 s Inter-Scan Delay = 0.02 s |

Mass Spectrometer Parameters: (Methods 2 & 3)

| Ionization Mode | ESI+ and ESI− |
| --- | --- |
| Capillary Voltage | 3.48 kV (ES+); 2.76 kV (ES−) |
| Cone Voltage | 15 V (ES+); 27 V (ES−) |
| Extractor Voltage | 1 V |
| RF Lens Voltage | 0.1 V |
| Source Temperature | 120° C. |
| Desolvation Temperature | 240° C. |
| Cone Gas Flow | 100 L/Hr |
| Desolvation Gas Flow | 600 L/Hr |
| LM Resolution | 15.0 |
| HM Resolution | 15.0 |
| Ion Energy | 0.5 |
| Multiplier | 600 |
| Scan Mode | Full Scan (Range = 100-800 m/z) ScanTime = 0.5 s Inter-Scan Delay = 0.3 s |

Semi-Preparative HPLC Method:

All purifications were performed on a Biotage Paraflex Flex System, equipped with four independent, binary flow-stream pumps, a UV detector with four-channel flow cell monitoring two wavelengths (220 and 254 nm), and four fraction collectors. Fractionation was performed at 254 nm. Waters XTerra Prep RP18, 5 μm, 100×19 mm columns were used at a flow rate of 20 mL/min. Gradients were applied according to the retention time of the desired product obtained from the analytical HPLC analysis.

Standard Binary Solvent System:

Mobile Phase A: 0.1% Trifluoracetic Acid in $H_2O$/Acetonitrile (95:5)

Mobile Phase B: Acetonitrile

Gradient A:

| Time (min) | % Phase A | % Phase B |
| --- | --- | --- |
| 0.0 | 100% | 0% |
| 6.0 | 80% | 20% |
| 8.0 | 80% | 50% |
| 8.5 | 50% | 100% |

Gradient B:

| Time (min) | % Phase A | % Phase B |
| --- | --- | --- |
| 0.0 | 100% | 0% |
| 6.0 | 70% | 30% |
| 8.0 | 0% | 100% |

Gradient C:

| Time (min) | % Phase A | % Phase B |
|---|---|---|
| 0.0 | 100% | 0% |
| 6.0 | 50% | 50% |
| 8.0 | 0% | 100% |

Gradient D:

| Time (min) | % Phase A | % Phase B |
|---|---|---|
| 0.0 | 90% | 10% |
| 6.0 | 30% | 70% |
| 8.0 | 0% | 100% |

The following abbreviations were employed:

| | |
|---|---|
| DMSO | dimethylsulfoxide |
| ID | identity |
| KDa | kiloDalton |
| mg | milligram |
| μg | microgram |
| mL | milliliter |
| μL | microliter |
| M | molar |
| mM | millimolar |
| μM | micromolar |
| nM | nanomolar |
| TBTU | O-(benzotriazol-1-yl)-N,N,N',N'-tetramethylisouronium tetrafluoroborate |
| DIPEA | N,N'-Diisopropylethylamine N,N'-dimethylacetamide (DMA) |
| Fmoc | 9H-fluoren-9-ylmethyl carbamate (Fmoc) |
| TBDMS | tert-butyldimethylsilyl |

Example 1

Preparation of 4-Chloro-6-(4,5,6,7-tetrahydro-1H-pyrazol[4,3-c]pyridin-3-yl)-benzene-1,3-diol dihydrochloride [(I), A=Cl, X=N, R=H, m=n=1]

Step a

1-Benzyl-3-(2,4-bis-benzyloxy-5-chloro-benzoyl)-piperidin-4-one [(4), A=Cl, PG$_1$=Benzyl, m=0 n=2]

In a dry, N$_2$ filled, stirred flask, 1M lithium(bis trimethyl-silylamide/THF solution (145 mL, 145 mmol) and THF (200 mL) are added and the solution is cooled to −30° C. To this solution a solution of 1-benzyl-piperidin-4-one (26.3 g, 140 mmol, 2 eq.) in THF (100 mL) is added. The resultant solution was stirred at −30° C. for 45 minutes. To this solution is added a solution of 2,4-bis-benzyloxy-5-chloro-benzoylchloride (27.3 g, 70 mmol) in THF (350 mL). The solution was stirred at −30° C. for 1 h then allowed to warm to room temperature. After 3 h, glacial acetic acid (9 mL, 150 mmol, 1.1 eq) were added and the solvent partially removed. After dilution with ethylacetate (500 mL), the organic solution was partitioned 1 M NaHCO$_3$ solution, then with brine, dried and evaporated. The crude reaction mixture was columned on a small pad of silica gel and eluted with ethylacetate/cyclohexane 1/1, then the pooled fractions evaporated. The residue was crystallised from Et$_2$O, to provide the title compound (29 g, 76% yield).

$^1$H NMR (400 MHz, DMSO-d$_6$) δ ppm 4.46 (dd, J 9.51, 4.76 Hz, 1H) 5.17 (s, 2H) 5.34 (s, 2H) 7.07 (s, 1H) 7.69 (s, 1H).

Step b

5-Benzyl-3-(2,4-bis-benzyloxy-5-chloro-phenyl)-4,5,6,7-tetrahydro-1H-pyrazolo[4,3-c]pyridine (a) [(5), A=Cl, X=N, R=Benzyl, m=n=1], Benzyl-{2-5-(2,4-bis-benzyloxy-[5-chloro-phenyl)-2H-2-pyrazol-3-yl]-ethyl}-amine (b) [A=Cl, X=N, R=Benzyl, m=2 n=0]

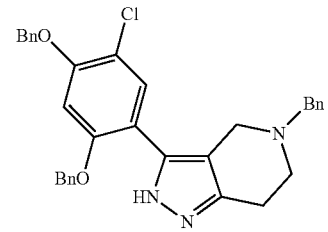

a

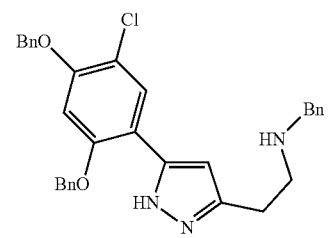

b

To a stirred solution of 1-benzyl-3-(2,4-bis-benzyloxy-5-chloro-benzoyl)-piperidin-4-one (26.1 g, 48 mmol) in EtOH (150 mL) and THF (100 mL) was slowly added drop wise a solution of hydrazine hydrate (10 mL, 200 mmol, 4 eq) in EtOH (25 mL). After stirring overnight, the solution was diluted with ethylacetate and thoroughly washed with water, then with brine, dried over Na$_2$SO$_4$ and evaporated. The residue was chromatographed on silica gel eluting with ethylacetate to give 5-benzyl-3-(2,4-bis-benzyloxy-5-chloro-phenyl)-4,5,6,7-tetrahydro-1H-pyrazolo[4,3-c]pyridine (a) (22.5 g, 86% yield).

$^1$H NMR (400 MHz, DMSO-d$_6$) δ ppm 2.50 (bs, 2H) 2.54 (bs, 2H) 3.29 (bs, 2H) 3.48 (s, 2H) 5.23 (s, 4H) 7.04-7.49 (m, 17H) 12.39 (bs).

Continuing the elution with ethylacetate/methanol 3/1, benzyl-{2-5-(2,4-bis-benzyloxy-[5-chloro-phenyl)-2H-2-pyrazol-3-yl]-ethyl}-amine (b) (3.2 g, yield 12.6%) was delivered.

$^1$H NMR (400 MHz, DMSO-d$_6$) δ ppm 2.69 (t, 2H) 2.78 (t, 2H) 5.24 (s, 2H) 5.27 (s, 2H) 6.35 (s, 1H) 7.09-7.49 (m, 17H) 12.54 (bs).

Step c1

4-Chloro-6-(4,5,6,7-tetrahydro-1H-pyrazolo[4,3-c]
pyridin-3-yl)-benzene-1,3-diol dihydrochloride [(I),
A=Cl, X=N, R=H, m=1 n=1]

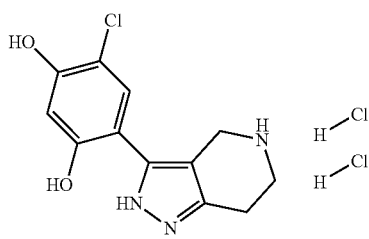

5-Benzyl-3-(2,4-bis-benzyloxy-5-chloro-phenyl)-4,5,6,7-tetrahydro-1H-pyrazolo[4,3-c]pyridine (40 g, 70 mmol) was dissolved in a mixture of ethanol (500 mL) and glacial acetic acid (150 mL) at room temperature before the addition of 10% Pd/C (4 g). The reaction mixture was stirred under hydrogen atmosphere (20 psi) for 12 h. The suspension was filtered through celite and the filtrate was concentrate to small volume. After addition of 12 M HCl solution (200 mL), the solution was evaporated to dryness and the residue was taken up in ethanol to provide the title compound (20.7 g, 82% yield).

$^1$H NMR (400 MHz, DMSO-$d_6$) δ ppm 2.25 (t, 2H) 3.41 (t, 2H) 4.16 (dd, 2H) 6.66 (s, 1H) 7.21 (s, 1H) 9.08 (bs, 2H) 10.38 (bs, 2H).

Example 2

Preparation of 3-(5-Chloro-2,4-dihydroxy-phenyl)-1,
5,6,7-tetrahydro-pyrazolo[4,3-b]pyridine-4-carboxylic acid tert-butyl ester (g) [(I), A=Cl, X=N,
R=Tertbutyloxycarbonyl, m=2 n=0]

3-(5-Chloro-2,4-dihydroxy-phenyl)-1,4,5,7-tetrahydro-pyrazolo[3,4-c]pyridine-6-carboxylic acid tert-butyl ester (h) [(I), A=Cl, X=N,
R=Tertbutyloxycarbonyl, m=0 n=2]

Step a 3-(2,4-Bis-benzyloxy-5-chloro-benzoyl)-3-oxo-piperidine-1-carboxylic acid tert-butyl ester (c) [(4),
A=Cl, PG$_1$=Tertbutyloxycarbonyl, m=2 n=0]

4-(2,4-Bis-benzyloxy-5-chloro-benzoyl)-3-oxo-piperidine-1-carboxylic acid tert-butyl ester (d) [(4),
A=Cl, PG$_1$=Tertbutyloxycarbonyl, m=1 n=0]

In a dry, N$_2$ filled, stirred flask, 1M lithium (bis trimethylsilylamide/THF solution (200 mL, 200 mmol) and THF (250 mL) are added and the solution is cooled to −35° C., then a solution of 3-oxo-piperidin-1-carboxylic acid tert-butyl ester (39.8 g, 200 mmol) in THF (150 mL) is added and the stirring was continued for 45 minutes at −35° C. To this solution is added drop wise a solution of 2,4-bis-benzyloxy-5-chloro-benzoylchloride (34.8 g, 100 mmol) in THF (400 mL). The solution was stirred at −30° C. for 1 h and allowed to warm to room temperature. After 3 h, glacial acetic acid (12 mL) was added and the solvent partially removed. After dilution with ethylacetate (750 mL), the organic solution was partitioned with brine, dried and evaporated. The crude reaction mixture was columned on a column of silica gel eluting with ethylacetate/cyclohexane 3/2 and the fractions containing the inseparable mixture of 3-(2,4-bis-benzyloxy-5-chloro-benzoyl)-3-oxo-piperidine-1-carboxylic acid tert-butyl ester (c) and 4-(2,4-bis-benzyloxy-5-chloro-benzoyl)-3-oxo-piperidine-1-carboxylic acid tert-butyl ester (d) were pooled and evaporated, to provide the two regioisomers (12.5 g, 25.2% yield).

Step b 3-(2,4-Bis-benzyloxy-5-chloro-phenyl)-1,5,6,7-tetrahydro-pyrazolo[4,3-b]pyridine-4-carboxylic acid
tert-butyl ester (e) [(5), A=Cl, X=N,
PG$_1$=Tertbutyloxycarbonyl, m=2 n=0]

3-(2,4-Bis-benzyloxy-5-chloro-phenyl)-1,4,5,7-tetrahydro-pyrazolo[3,4-c]pyridine-6-carboxylic acid
tert-butyl ester (f) [(5), A=Cl, X=N,
PG$_1$=Tertbutyloxycarbonyl, m=0 n=2]

To a stirred solution of 3-(2,4-bis-benzyloxy-5-chlorobenzoyl)-3-oxo-piperidine-1-carboxylic acid tert-butyl ester and 4-(2,4-bis-benzyloxy-5-chloro-benzoyl)-3-oxo-piperidine-1-carboxylic acid tert-butyl ester (12 g, 22 mmol) in EtOH (50 mL) and THF (50 mL) was slowly added drop wise a solution of hydrazine hydrate (5 mL, 100 mmol) in EtOH (10 mL). After stirring overnight, the solution was diluted with ethylacetate and thoroughly washed with water then with brine, dried over Na$_2$SO$_4$ and evaporated. The residue was chromatographed on silica gel eluting with ethylacetate/cyclohexane 3/1 to afford the mixture of the two regioisomers 3-(2,4-bis-benzyloxy-5-chloro-phenyl)-1,5,6,7-tetrahydro-pyrazolo[4,3-b]pyridine-4-carboxylic acid tert-butyl ester (e) and 3-(2,4-bis-benzyloxy-5-chloro-phenyl)-1,4,5,7-tetrahydro-pyrazolo[3,4-c]pyridine-6-carboxylic acid tert-butyl ester (f) (7.3 g, 63% yield).

Step c3

3-(5-Chloro-2,4-dihydroxy-phenyl)-1,5,6,7-tetrahydro-pyrazolo[4,3-b]pyridine-4-carboxylic acid tertbutyl ester (g) [(I), A=Cl, X=N,
R=Tertbutyloxycarbonyl, m=2 n=0]

3-(5-Chloro-2,4-dihydroxy-phenyl)-1,4,5,7-tetrahydro-pyrazolo[3,4-c]pyridine-6-carboxylic acid tertbutyl ester (h) [(I), A=Cl, X=N,
R=Tertbutyloxycarbonyl, m=0 n=2]

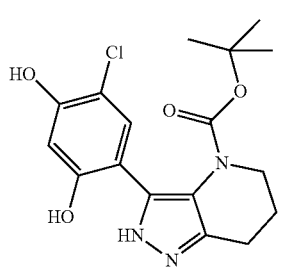

g

-continued

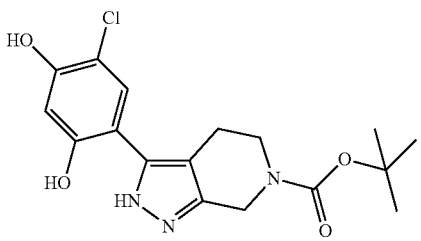

A mixture of 3-(2,4-bis-benzyloxy-5-chloro-phenyl)-1,5,6,7-tetrahydro-pyrazolo[4,3-b]pyridine-4-carboxylic acid tert-butyl ester (e) and 3-(2,4-bis-benzyloxy-5-chloro-phenyl)-1,4,5,7-tetrahydro-pyrazolo[3,4-c]pyridine-6-carboxylic acid tert-butyl ester (f) (7 g, 13 mmol) was dissolved in a mixture of ethanol (50 mL) and glacial acetic acid (10 mL) at room temperature before the addition of 10% Pd/C (1 g). The reaction mixture was stirred under hydrogen atmosphere (20 psi) for 10 h. The suspension was filtered through celite and the filtrate was concentrate to small volume and ethylacetate (200 mL) was added. The solution was washed with 1 M NaHCO$_3$ solution, then with brine and dried. The solvent was removed and the crude reaction mixture was carefully chromatographed on silica gel eluting with ethylacetate/methanol 6/1 to provide 3-(5-chloro-2,4-dihydroxy-phenyl)-1,5,6,7-tetrahydro-pyrazolo[4,3-b]pyridine-4-carboxylic acid tert-butyl ester (g) (2.3 g, 48% yield).

$^1$H NMR (400 MHz, DMSO-d$_6$) δ ppm 1.11 (bs, 9H) 1.85 (m, 2H) 2.76 (m, 2H) 3.66 (t, 2H) 6.05 (s, 1H) 7.25 (s, 2H) 10.44 (bs, 2H), 12.5 (bs, 1H).

Continuing the elution with ethylacetate/methanol 5/1, 3-(5-chloro-2,4-dihydroxy-phenyl)-1,4,5,7-tetrahydro-pyrazolo[3,4-c]pyridine-6-carboxylic acid tert-butyl ester (h) was delivered (1.3 g, 27% yield).

$^1$H NMR (400 MHz, DMSO-d$_6$) δ ppm 1.39 (bs, 9H) 2.73 (m, 2H) 3.59 (m, 2H) 4.47 (m, 2H) 6.68 (s, 1H) 7.25 (bs, 2H) 10.38 (bs, 2H), 10.61 (bs, 2H), 12.64 (bs, 1H).

Step e

4-Chloro-6-(4,5,6,7-tetrahydro-1H-pyrazolo[4,3-b]pyridin-3-yl)-benzene-1,3-diol hydrochloride [(I), A=Cl, X=N, R=H, m=2 n=0]

To a stirred solution of 3-(5-chloro-2,4-dihydroxy-phenyl)-1,5,6,7-tetrahydro-pyrazolo[4,3-b]pyridine-4-carboxylic acid tert-butyl ester (2 g, 3.6 mmol) in THF (15 mL) was added 4 M HCl dioxane solution (50 mL). After standing 2 h the solvent was collected and washed with dioxane then with diethylether, to provide after drying the title compound (1.43 g, 78% yield).

$^1$H NMR (400 MHz, DMSO-d$_6$) δ ppm 2.08 (m, 2H) 2.75 (m, 2H) 3.29 (m, 2H) 6.67 (s, 1H) 7.44 (s, 1H) 10.40 (s, 1H) 10.44 (s, 1H) 10.11 (m, 2H) 10.61 (bs, 2H).

Example 3

Preparation of 4-Chloro-6-(4,5,6,7-tetrahydro-1H-pyrazolo[3,4-c]pyridin-3-yl)-benzene-1,3-diol hydrochloride [(I), A=Cl, X=N, R=H, m=0 n=2]

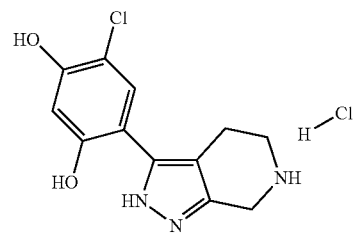

Operating as in Example 2 Step c3, but employing 3-(5-chloro-2,4-dihydroxy-phenyl)-1,4,5,7-tetrahydro-pyrazolo[3,4-c]pyridine-6-carboxylic acid tert-butyl ester instead of 3-(5-chloro-2,4-dihydroxy-phenyl)-1,5,6,7-tetrahydro-pyrazolo[4,3-b]pyridine-4-carboxylic acid tert-butyl ester, followed by step e, the title compound was obtained in yield 63%.

$^1$H NMR (400 MHz, DMSO-d$_6$) δ ppm 2.83 (m, 2H) 3.84 (m, 2H) 4.24 (m, 2H) 6.68 (s, 1H) 7.20 (s, 1H) 9.23 (bs, 2H) 10.39 (m, 3H).

Example 4

Preparation of 4-Chloro-6 (1,4,5,6-tetrahydro-pyrrolo[3,4-c]pyrazol-3-yl)-benzene-1,3-diol hydrochloride [(I), A=Cl, X=N, R=H, m=0 n=1]

Step a, b

1-Benzyl-3-(2,4-bis-benzyloxy-5-chloro-phenyl)-(1,4,5,6-tetrahydro-pyrrolo[3,4-c]pyrazole (I) [(5), A=Cl, X=N, PG$_1$=Benzyl, m=0 n=1]

Operating as in Example 1 Step a, but employing 1-benzyl-pirrolidin-3-one instead of 1-benzyl-piperidin-4-one, the intermediate 1-benzyl-4-(2,4-bis-benzyloxy-5-chloro-benzoyl)-pyrrolidin-3-one was straightforward converted into 1-benzy-3-(2,4-bis-benzyloxy-5-chloro-phenyl)-(1,4,5,6-tetrahydro-pyrrolo[3,4-c]pyrazole (12% yield).

$^1$H NMR (400 MHz, DMSO-d$_6$) δ ppm 3.30 (dd, 2H) 3.51 (s, 2H) 3.72 (dd, 2H) 5.25 (s, 4H) 7.35 (m, 15H) 7.60 (s, 2H) 12.54 (bs, 1H).

Step c1

4-Chloro-6-(1,4,5,6-tetrahydro-pyrrolo[3,4-c]pyrazol-3-yl)-benzene-1,3-diol hydrochloride (m) [(I), A=Cl, X=N, R=H, m=0 n=1]

Operating as in Example 1 Step c1, the title compound was obtained in 75% yield.

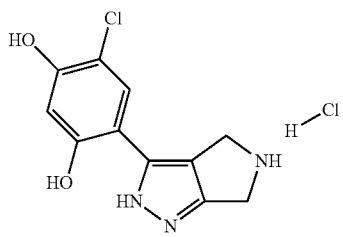

¹H NMR (400 MHz, DMSO-d₆) δ ppm 4.29 (dd, 4H) 6.68 (s, 1H) 7.52 (s, 1H) 9.80 (bs, 2H) 7.21 (s, 1H) 9.80 (bs, 2H) 10.40 (bs, 2H).

Example 5

Preparation of 4-Chloro-6-(4,5,6,7-tetrahydro-isoxazolo[4,3-c]pyridin-3-yl)-benzene-1,3-diol hydrochloride [(I), A=Cl, X=O, R=H, m=1 n=1]

Step a 3-(2,4-Bis-benzyloxy-5-chloro-benzoyl)-4-oxo-piperidine-1-carboxylic acid acid tert-butyl ester (n) [(4), A=Cl, X=N, PG₁=Tertbutyloxycarbonyl, m=1 n=1]

Operating as in Example 1 Step a, but employing 4-oxo-piperidine-1-carboxylic tert-butyl ester instead of 1-benzyl-piperidin-4-one, the title compound was obtained in 45% yield.

¹H NMR (400 MHz, DMSO-d₆) δ ppm 1.33 (bs, 9H) 3.32-3.92 (m, 4H) 4.38 (bs, 1H) 5.32 (s, 4H) 6.38-6.49 (m, 10H) 7.38 (s, 1H) 7.77 (s, 1H).

Step f3

3-(5-Chloro-2,4-dihydroxy-benzoyl)-4-oxo-piperidine-1-carboxylic acid tert-butyl ester (o) [(9), A=Cl, PG₁=Tertbutyloxycarbonyl, m=1 n=0]

Operating as in Example 1 Step c1, but employing 3-(2,4-bis-benzyloxy-5-chloro-benzolyl)-4-oxo-piperidine-1-carboxylic acid acid tert-butyl ester and using THF, the title compound was obtained in 95% yield.

¹H NMR (400 MHz, DMSO-d₆) δ ppm 1.36 (bs, 9H) 4.39 (bs, 1H) 5.47 (s, 4H) 6.49 7.35 (s, 1H) 10.43 (bs, 2H).

Step i 3-(5-Chloro-2,4-dihydroxy-phenyl)-4,5,6,7-tetrahydro-isoxazolo[4,3-c]pyridine-5-carboxylic acid tert-butyl ester (p) [(I), A=Cl, X=O, R=Tertbutyloxycarbonyl, m=1 n=1]

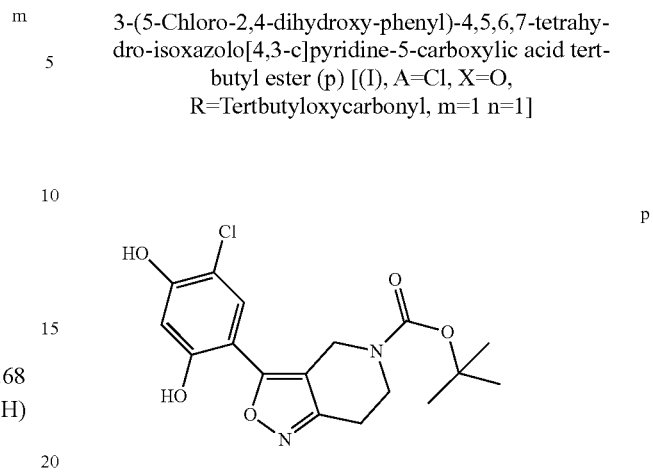

A stirred solution of 3-(5-chloro-2,4-dihydroxy-benzoyl)-4-oxo-piperidine-1-carboxylic acid tert-butyl ester (g 40, 25 mmol) and hydroxylamine hydrochloride (9.3 g, 134 mmol, 5.4 eq) in a mixture of ethanol (300 mL) and pyridine (300 mL) was refluxed for 2 h. The solvent was removed and the residue was taken up in ethylacetate (600 mL). After washing with 1 M HCl (200 mL) and brine, the organic phase was dried over sodium sulphate and the solvent removed. The residue was crystallised twice from ethylacetate to provide the title compound (36 g, 80% yield).

¹H NMR (400 MHz, DMSO-d₆) δ ppm 1.41 (bs, 9H) 4.39 (t, 2H) 2.77 (t, 2H) 3.63 (t, 2H) 4.49 (s, 2H) 6.67 (s, 1H) 7.39 (s, 1H) 10.50-10.65 (s, 2H).

Step j

4-Chloro-6-(4,5,6,7-tetrahydro-isoxazolo[4,3-c]pyridin-3-yl)-benzene-1,3-diol hydrochloride (q) [(I), A=Cl, X=O, R=H, m=1 n=1]

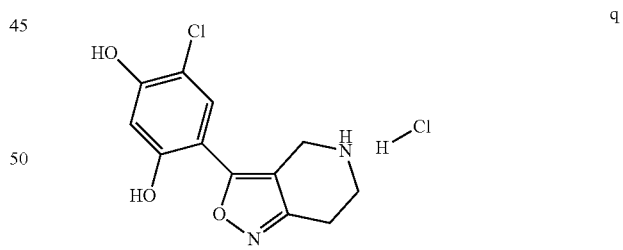

To a stirred solution of 3-(5-chloro-2,4-dihydroxy-phenyl)-4,5,6,7-tetrahydro-isoxazolo[4,3-c]pyridine-5-carboxylic acid tert-butyl ester (36 g, 98 mmol) in ethanol (350 mL) was added 12 M HCl solution (100 mL, 1200 mmol, 12 eq)). After standing at room temperature for 2 h, the suspension was evaporated at small volume and the collected precipitate was thoroughly washed with twice with ethanol then with diethyl ether, to provide after drying the title compound (24.5 g, 82% yield).

¹H NMR (400 MHz, DMSO-d₆) δ ppm 3.04 (t 9H) 3.46 (t, 2H) 4.24 (s, 2H) 6.72 (s, 1H) 7.46 (s, 1H) 9.13 (bs, 2H) 10.72-10.81 (bs, 2H).

Example 6

Preparation of [3-(5-Chloro-2,4-dihydroxy-phenyl)-1,4,6,7-tetrahydro-pyrazolo[4,3-c]pyridine-5-yl]-acetic acid hydrochloride [(I), A=Cl, X=N, R=CH$_2$COOH, m=1 n=1]

Step k7

[3-(5-Chloro-2,4-dihydroxy-phenyl)-1,4,6,7-tetrahydro-pyrazolo[4,3-c]pyridine-5-yl]-acetic acid tert-butyl ester [(I), A=Cl, X=N, R=CH$_2$COOC$_4$H$_9$, m=1 n=1]

To a stirred solution of 4-chloro-6-(4,5,6,6-tetrahydro-1H-pyrazolo[4,3-c]pyridine-3-yl)-1-benzene-1,3-diol (2.5 g, 9.4 mmol) in DMF (30 mL) and DIPEA (2.45 mL) was slowly added at room temperature a solution of bromo-acetic acid tert-butyl ester (ml 1, 1.1 eq)) in THF (20 mL). After stirring for two h, ethylacetate was added and the solution was thoroughly washed with brine. After drying, the residue was crystallised from Et$_2$O to provide the title compound (2.8 g, 78% yield).

$^1$H NMR (400 MHz, DMSO-d$_6$) δ ppm 1.45 (s 9H) 3.78 (m 2H) 2.86 (m, 2H) 3.41 (s, 2H) 3.78 (m, 2H) 6.58 (s 1H) 7.10 (s 1H) 11.21 (s 1H) 11.35 (s 1H) 12.87 (bs 1H).

Conversion 1

[3-(5-Chloro-2,4-dihydroxy-phenyl)-1,4,6,7-tetrahydro-pyrazolo[4,3-c]pyridine-5l1]-acetic acid hydrochloride [(I,) A=Cl, X=N, R=CH$_2$COOH, m=1 n=1]

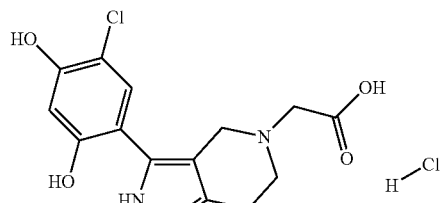

To a stirred solution of [3-(5-chloro-2,4-dihydroxy-phenyl)-1,4,6,7-tetrahydro-pyrazolo[4,3-c]pyridine-5-yl]-acetic acid tert-butyl ester (2.7 g, 7 mmol) in dioxane (5 mL) was added of 4 M HCl solution in dioxane (35 mL). After 4 h, the precipitate was filtered off and washed with dioxane then with Et$_2$O, to afford the title compound (2.3 g, 85% yield).

Example 7

Step k7

Preparation of ethyl 3-[3-(5-chloro-2,4-dihydroxy-phenyl)-2,4,6,7-tetrahydro-pyrazolo[4,3-c]pyridin-5-yl]-propanoate [(I), A=Cl, X=N, R=CH$_2$CH$_2$COOC$_2$H$_5$, m=1 n=1]

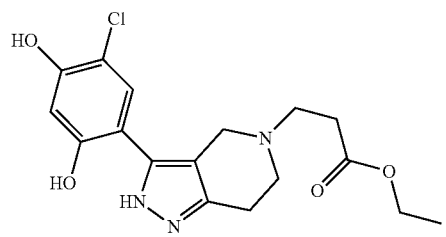

Operating as in Example 6, but employing 3-bromo-propanoic acid ethyl ester instead of bromo-acetic acid tert-butyl ester, the title compound was obtained in 67% yield.

HRMS (ESI): m/z calcd for C$_{17}$H$_{21}$ClN$_3$O$_4$$^+$ 366.1215 [M+H]$^+$. found 366.1217.

Example 8

Preparation of 4-Chloro-6-[5-(3-morpholin-4-yl-3-oxopropyl)-4,5,6,7-tetrahydro-pyrazolo[4,3-c]pyridin-3-yl]benzene-1,3-diol [(I), A=Cl, X=N, R=CH$_2$CH$_2$NC$_4$H$_8$O, m=1 n=1]

Conversion 1

3-[3-(5-Chloro-2,4-dihydroxyphenyl)-1,4,6,7-tetrahydro-pyrazolo[4,3-c]pyridin-5-yl]-propanoic acid [(I), A=Cl, X=N, R=CH$_2$CH$_2$COOH, m=1 n=1]

To a stirred solution of ethyl 3-[3-(5-chloro-2,4-dihydroxyphenyl)-2,4,6,7-tetrahydro-pyrazolo[4,3-c]pyridin-5-yl] propanoate (0.365 g, 1 mmol) in ethanol 96% (5 mL) was added 1.5 M KOH in EtOH (3.3 mL, 5 mmol). After 12 h, the reaction mixture was concentrated, diluted with water and acidified with citric acid. The precipitate was filtered off and washed with Et$_2$O, to afford the title compound (0.286 g, yield 85%).

HRMS (ESI): m/z calcd for C$_{15}$H$_{17}$ClN$_3$O$_4$$^+$ 338.0902 [M+H]$^+$. found 338.0913.

Conversion 2

4-Chloro-6-[5-(3-morpholin-4-yl-3-oxopropyl)-4,5,6,7-tetrahydro-pyrazolo[4,3-c]pyridin-3-yl]-benzene-1,3-diol [(I), A=Cl, X=N, R=CH$_2$CH$_2$CONC$_4$H$_8$O, m=1 n=1]

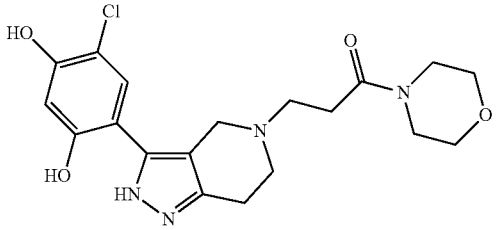

To a stirred solution of 3-[3-(5-chloro-2,4-dihydroxyphenyl)-1,4,6,7-tetrahydro-pyrazolo[4,3-c]pyridin-5-yl]propanoic acid (0.07 g, 0.2 mmol) in DMF (1 mL) was added EDC (0.046 g, 0.24 mmol), HOBT (0.032 g, 0.24 mmol), morpholine (0.035 mL, 0.4 mmol) and DIPEA (0.070 mL, 0.4 mmol). After 4 h, the reaction mixture was concentrated, diluted with DCM and washed with saturated solution of sodium hydrogen carbonate, dried over Na$_2$SO$_4$ and evaporated to dryness. Purification by flash chromatography by elution with DCM/EtOH 95/5 provided the title compound (0.065 g, yield 80%).

HRMS (ESI): m/z calcd for C$_{19}$H$_{24}$ClN$_4$O$_4$$^+$ 407.1481 [M+H]$^+$. found 407.1486.

Example 9

Conversion 2

Preparation of 4-Chloro-6-[5-(2-morpholin-4-yl-2-oxoethyl)-4,5,6,7-tetrahydro-pyrazolo[4,3-c]pyridin-3-yl]-benzene-1,3-diol [(I), A=Cl, X=N, R=CH$_2$CONC$_4$H$_8$O, m=1 n=1]

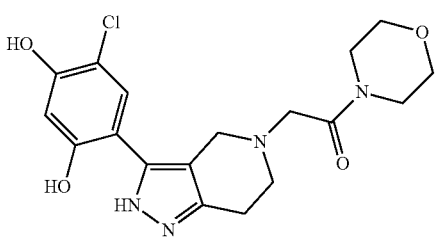

Operating as in Example 8, but employing [3-(5-chloro-2,4-dihydroxy-phenyl)-1,4,6,7-tetrahydro-pyrazolo[4,3-c]pyridine-5-yl]-acetic acid hydrochloride instead of 3-[3-(5-chloro-2,4-dihydroxyphenyl)-1,4,6,7-tetrahydro-pyrazolo[4,3-c]pyridin-5-yl]propanoic acid, the title compound was obtained in 74% yield.

HRMS (ESI): m/z calcd for C$_{18}$H$_{22}$ClN$_4$O$_4$$^+$ 393.1324 [M+H]$^+$. found 393.1336.

The following compounds were similarly prepared:

| Name | ION | HRMS (ESI): Exact Mass Calc | HRMS (ESI): Exact Mass Found |
|---|---|---|---|
| tert-butyl [3-(5-chloro-2,4-dihydroxyphenyl)-1,4,6,7-tetrahydro-5H-pyrazolo[4,3-c]pyridin-5-yl]acetate | M + H | 380.1372 | 380.1377 |
| [3-(5-chloro-2,4-dihydroxyphenyl)-1,4,6,7-tetrahydro-5H-pyrazolo[4,3-c]pyridin-5-yl]acetic acid dihydrochloride | M + H | 324.0746 | 324.0749 |
| 4-chloro-6-[5-(2-morpholin-4-yl-2-oxoethyl)-4,5,6,7-tetrahydro-1H-pyrazolo[4,3-c]pyridin-3-yl]benzene-1,3-diol | M + H | 393.1324 | 393.1336 |
| ethyl 3-[3-(5-chloro-2,4-dihydroxyphenyl)-2,4,6,7-tetrahydro-5H-pyrazolo[4,3-c]pyridin-5-yl]propanoate | M + H | 366.1215 | 366.1217 |
| 3-[3-(5-chloro-2,4-dihydroxyphenyl)-1,4,6,7-tetrahydro-5H-pyrazolo[4,3-c]pyridin-5-yl]propanoic acid | M + H | 338.0902 | 338.0913 |
| 4-chloro-6-[5-(3-morpholin-4-yl-3-oxopropyl)-4,5,6,7-tetrahydro-1H-pyrazolo[4,3-c]pyridin-3-yl]benzene-1,3-diol | M + H | 407.1481 | 407.1486 |

Example 10

Step k3

Preparation of 3-(5-Chloro-2,4-dihydroxy-phenyl)-1,4,6,7-tetrahydro-pyrazolo[4,3-c]pyridine-5-carboxylic acid cyclohexylamide [(I), A=Cl, X=N, R=CONHC$_6$H$_{11}$, m=1 n=1]

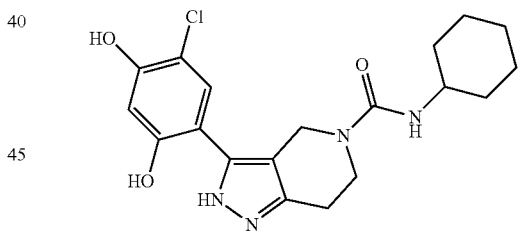

To a stirred solution of 4-chloro-6-(4,5,6,7-tetrahydro-1H-pyrazolo[4,3-c]-benzene-1,3-diol dihydrochloride (0.35 g, 1.3 mmol) in DMF (5 mL) was added triethylamine (0.6 mL) followed by the addition of a solution of to cyclohexylisocyanate (0.2 g, 1.6 mmol, 1.2 eq) in DMF (2 mL).

After stirring overnight, the solvent was removed and the crude was taken up in 1 M NaOH solution (25 mL, 25 mmol). After 1 hour, the solution was acidified with 1 M citric acid solution (35 mL) and after dilution with water thoroughly extracted with ethylacetate. After drying, the solvent was removed and the residue was filtered on a small plug of silica gel eluting with ethylacetate. After pooling and removal of the solvent, the residue was crystallised from a small amount of acetone, to provide the title compound (0.28 g, 70% yield).

$^1$H NMR (400 MHz, DMSO-d$_6$) δ ppm 1.17-1.25 (m 5H) 1.56-1.76 (m, 5H) 2.69 (m, 2H) 3.42 (m, 1H) 3.62 (m, 2H) 4.53 (bs 2H) 6.39 (d 1H) 6.56 (s 1H) 7.22 (s 1H) (s, 1H) 9.13 (bs, 2H) 10.22 (bs, 2H) 11.28 (bs 1H) 12.90 (bs 1H)

The following compounds were similarly prepared:

| Name | ION | HRMS (ESI): Exact Mass Calc | HRMS (ESI): Exact Mass Found |
|---|---|---|---|
| 3-(5-chloro-2,4-dihydroxyphenyl)-N-[4-(dimethylamino)phenyl]-1,4,6,7-tetrahydro-5H-pyrazolo[4,3-c]pyridine-5-carboxamide | M + H | 428.1484 | 428.1487 |
| 3-(5-chloro-2,4-dihydroxyphenyl)-N-(3-phenoxyphenyl)-1,4,6,7-tetrahydro-5H-pyrazolo[4,3-c]pyridine-5-carboxamide | M + H | 477.1324 | 477.1323 |
| N-[4-(benzyloxy)phenyl]-3-(5-chloro-2,4-dihydroxyphenyl)-1,4,6,7-tetrahydro-5H-pyrazolo[4,3-c]pyridine-5-carboxamide | M + H | 491.1481 | 491.1481 |
| 3-(5-chloro-2,4-dihydroxyphenyl)-N-(2-phenylethyl)-1,4,6,7-tetrahydro-5H-pyrazolo[4,3-c]pyridine-5-carboxamide | M + H | 413.1375 | 413.1379 |
| 3-(5-chloro-2,4-dihydroxyphenyl)-N-phenyl-1,4,6,7-tetrahydro-5H-pyrazolo[4,3-c]pyridine-5-carboxamide | M + H | 385.1062 | 385.1066 |
| 3-(5-chloro-2,4-dihydroxyphenyl)-N-(4-methoxyphenyl)-1,4,6,7-tetrahydro-5H-pyrazolo[4,3-c]pyridine-5-carboxamide | M + H | 415.1168 | 415.1172 |
| 3-(5-chloro-2,4-dihydroxyphenyl)-N-propyl-1,4,6,7-tetrahydro-5H-pyrazolo[4,3-c]pyridine-5-carboxamide | M + H | 351.1219 | 351.1225 |
| 3-(5-chloro-2,4-dihydroxyphenyl)-N-(1-methylethyl)-1,4,6,7-tetrahydro-5H-pyrazolo[4,3-c]pyridine-5-carboxamide | M + H | 351.1219 | 351.1223 |
| 3-(5-chloro-2,4-dihydroxyphenyl)-N-cyclohexyl-1,4,6,7-tetrahydro-5H-pyrazolo[4,3-c]pyridine-5-carboxamide | M + H | 391.1532 | 391.1533 |
| 3-(5-chloro-2,4-dihydroxyphenyl)-N-[3-(methylsulfanyl)phenyl]-1,4,6,7-tetrahydro-5H-pyrazolo[4,3-c]pyridine-5-carboxamide | M + H | 431.0939 | 431.0951 |

Example 11

Preparation of 2-Amino-1-[3-(5-chloro-2,4-dihydroxyphenyl)-1,4,6,7-tetrahydro-5H-pyrazolo[4,3-c]pyridin-5-yl]ethanone [(I), A=Cl, X=N, R=COCH$_2$NH$_2$, m=1 n=1]

Step k1

{2-[3-(5-Chloro-2,4-dihydroxy-phenyl)-2,4,6,7-tetrahydro-pyrazolo[4,3-c]pyridine-5-yl]-2-oxo-ethyl}-carbamic acid tert-butyl ester [(I), A=Cl, X=N, R=COCH$_2$NHCOOC$_4$H$_9$, m=1 n=1]

To a suspension of Boc-Glycine (0.017 g, 0.1 mmol) in N,N'-dimethylacetamide (DMA) (0.5 mL) TBTU (0.035 g, 0.11 mmol) and DIPEA (0.017 mL, 0.18 mmol) were added all in a 1 dram vial (4 mL working volume). The mixture was stirred at room temperature for 30 minutes. Then 4-chloro-6-(4,5,6,7-tetrahydro-1H-pyrazolo[4,3-c]pyridin-3-yl)benzene-1,3-diol (0.024 g, 0.09 mmol), dissolved in DMA (0.5 mL) was added and the reaction was stirred for an additional 16 h at room temperature. HPLC analysis after 16 h indicated the conversion of the starting material to product.

At this time, a 2N NaOH solution (0.2 mL) was added to the above and stirred for 2 h at room temperature. This treatment liberated the N-[amino(dimethylamino)methylene]-N-methylmethanaminium species attached to the pyrazole ring that was generated by the use of TBTU as an acylating reagent. After 2 h of NaOH treatment, a 2N HCl solution (0.2 mL) was added to neutralize the solution. The solvent was removed in vacuo.

Step c2

2-Amino-1-[3-(5-chloro-2,4-dihydroxyphenyl)-1,4,6,7-tetrahydro-5H-pyrazolo[4,3-c]pyridin-5-yl]ethanone [(I), A=Cl, X=N, R=COCH$_2$NH$_2$, m=1 n=1]

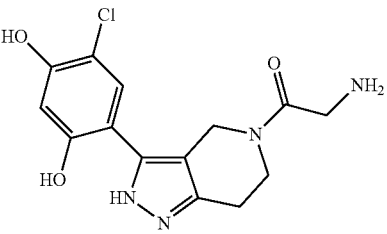

To the tert-butyl {2-[3-(5-chloro-2,4-dihydroxyphenyl)-1,4,6,7-tetrahydro-5H-pyrazolo[4,3-c]pyridin-5-yl]-2-oxoethyl}carbamate compound, a mixture of TFA/DCM (1:1) (0.5 mL) was charged to the vial and stirred for 1 h at room temperature. The solvent was then removed in vacuo and the product was purified via semi-preparative HPLC according to the protocol indicated below.

In the case where the protection for the amine was an Fmoc group, a of 10% piperidine solution (0.5 mL) in DMF was added to the vial, which was then stirred for 1 hour. The solvent was then removed in vacuo and the product was purified via semi-preparative HPLC according to the protocol indicated below.

In the case where a tert-butyldimethylsilyl (TBDMS) protecting group existed, a 2N NaOH solution (0.2 mL) was added to the reaction cocktail in step 1, and stirred for 2 hours at ambient. After the 2 h of NaOH treatment, a 2N HCl solution (0.2 mL) was added to neutralize the base. The solvent was then removed in vacuo and the product was purified via semi-preparative HPLC according to the protocol indicated below.

By working analogously and in parallel, the following compounds were prepared:

| Name | M + H | RT | METHOD |
|---|---|---|---|
| 1-[3-(5-chloro-2,4-dihydroxyphenyl)-1,4,6,7-tetrahydro-5H-pyrazolo[4,3-c]pyridin-5-yl]ethanone | 308.07 | 0.746 | 1 |
| 2-amino-1-[3-(5-chloro-2,4-dihydroxyphenyl)-1,4,6,7-tetrahydro-5H-pyrazolo[4,3-c]pyridin-5-yl]ethanone | 323.08 | 1.08 | 3 |
| 1-[3-(5-chloro-2,4-dihydroxyphenyl)-1,4,6,7-tetrahydro-5H-pyrazolo[4,3-c]pyridin-5-yl]-2-(methylamino)ethanone | 337.1 | 0.64 | 3 |
| 1-[3-(5-chloro-2,4-dihydroxyphenyl)-1,4,6,7-tetrahydro-5H-pyrazolo[4,3-c]pyridin-5-yl]-2-(dimethylamino)ethanone | 351.11 | 0.57 | 1 |
| [3-(5-chloro-2,4-dihydroxyphenyl)-1,4,6,7-tetrahydro-5H-pyrazolo[4,3-c]pyridin-5-yl](1H-pyrrol-3-yl)methanone | 359.08 | 0.81 | 1 |
| [3-(5-chloro-2,4-dihydroxyphenyl)-1,4,6,7-tetrahydro-5H-pyrazolo[4,3-c]pyridin-5-yl](1H-pyrazol-4-yl)methanone | 360.08 | 0.7 | 1 |
| [3-(5-chloro-2,4-dihydroxyphenyl)-1,4,6,7-tetrahydro-5H-pyrazolo[4,3-c]pyridin-5-yl](1H-imidazol-4-yl)methanone | 360.08 | 1.186 | 1 |
| [3-(5-chloro-2,4-dihydroxyphenyl)-1,4,6,7-tetrahydro-5H-pyrazolo[4,3-c]pyridin-5-yl][(2S)-2,5-dihydro-1H-pyrrol-2-yl]methanone | 361.1 | 1.404 | 1 |
| [3-(5-chloro-2,4-dihydroxyphenyl)-1,4,6,7-tetrahydro-5H-pyrazolo[4,3-c]pyridin-5-yl][(2S)-pyrrolidin-2-yl]methanone | 363.11 | 1.109 | 1 |
| [3-(5-chloro-2,4-dihydroxyphenyl)-1,4,6,7-tetrahydro-5H-pyrazolo[4,3-c]pyridin-5-yl][(2R)-pyrrolidin-2-yl]methanone | 363.11 | 1.11 | 1 |
| [3-(5-chloro-2,4-dihydroxyphenyl)-1,4,6,7-tetrahydro-5H-pyrazolo[4,3-c]pyridin-5-yl](tetrahydrofuran-3-yl)methanone | 364.1 | 0.787 | 1 |
| N-{2-[3-(5-chloro-2,4-dihydroxyphenyl)-1,4,6,7-tetrahydro-5H-pyrazolo[4,3-c]pyridin-5-yl]-2-oxoethyl}acetamide | 365.09 | 0.626 | 1 |
| 1-{2-[3-(5-chloro-2,4-dihydroxyphenyl)-1,4,6,7-tetrahydro-5H-pyrazolo[4,3-c]pyridin-5-yl]-2-oxoethyl}urea | 366.09 | 0.574 | 1 |
| [3-(5-chloro-2,4-dihydroxyphenyl)-1,4,6,7-tetrahydro-5H-pyrazolo[4,3-c]pyridin-5-yl](pyridin-4-yl)methanone | 371.08 | 0.738 | 1 |
| [3-(5-chloro-2,4-dihydroxyphenyl)-1,4,6,7-tetrahydro-5H-pyrazolo[4,3-c]pyridin-5-yl](pyridin-3-yl)methanone | 371.08 | 0.682 | 1 |
| [3-(5-chloro-2,4-dihydroxyphenyl)-1,4,6,7-tetrahydro-5H-pyrazolo[4,3-c]pyridin-5-yl](3-thienyl)methanone | 376.04 | 1.012 | 1 |
| 1-[3-(5-chloro-2,4-dihydroxyphenyl)-1,4,6,7-tetrahydro-5H-pyrazolo[4,3-c]pyridin-5-yl]-2-(1H-tetrazol-1-yl)ethanone | 376.08 | 0.701 | 1 |
| 3-({2-[3-(5-chloro-2,4-dihydroxyphenyl)-1,4,6,7-tetrahydro-5H-pyrazolo[4,3-c]pyridin-5-yl]-2-oxoethyl}amino)propanenitrile | 376.11 | 0.679 | 1 |
| [3-(5-chloro-2,4-dihydroxyphenyl)-1,4,6,7-tetrahydro-5H-pyrazolo[4,3-c]pyridin-5-yl](1,3-thiazol-4-yl)methanone | 377.04 | 0.854 | 1 |
| [3-(5-chloro-2,4-dihydroxyphenyl)-1,4,6,7-tetrahydro-5H-pyrazolo[4,3-c]pyridin-5-yl](piperidin-4-yl)methanone | 377.13 | 1.258 | 1 |
| [3-(5-chloro-2,4-dihydroxyphenyl)-1,4,6,7-tetrahydro-5H-pyrazolo[4,3-c]pyridin-5-yl](piperidin-3-yl)methanone | 377.13 | 1.255 | 1 |
| [3-(5-chloro-2,4-dihydroxyphenyl)-1,4,6,7-tetrahydro-5H-pyrazolo[4,3-c]pyridin-5-yl](tetrahydro-2H-pyran-4-yl)methanone | 378.11 | 0.809 | 1 |
| [3-(5-chloro-2,4-dihydroxyphenyl)-1,4,6,7-tetrahydro-5H-pyrazolo[4,3-c]pyridin-5-yl][(2S,4R)-4-hydroxypyrrolidin-2-yl]methanone | 379.11 | 1.635 | 1 |
| [3-(5-chloro-2,4-dihydroxyphenyl)-1,4,6,7-tetrahydro-5H-pyrazolo[4,3-c]pyridin-5-yl][(2S,3S)-3-hydroxypyrrolidin-2-yl]methanone | 379.11 | 0.936 | 1 |
| 1-{3-[3-(5-chloro-2,4-dihydroxyphenyl)-1,4,6,7-tetrahydro-5H-pyrazolo[4,3-c]pyridin-5-yl]-3-oxopropyl}urea | 380.1 | 0.611 | 1 |
| 1-[3-(5-chloro-2,4-dihydroxyphenyl)-1,4,6,7-tetrahydro-5H-pyrazolo[4,3-c]pyridin-5-yl]-2-phenylethanone | 384.1 | 1.128 | 1 |
| (4-aminophenyl)[3-(5-chloro-2,4-dihydroxyphenyl)-1,4,6,7-tetrahydro-5H-pyrazolo[4,3-c]pyridin-5-yl]methanone | 385.1 | 1.163 | 1 |
| (4-aminophenyl)[3-(5-chloro-2,4-dihydroxyphenyl)-1,4,6,7-tetrahydro-5H-pyrazolo[4,3-c]pyridin-5-yl]methanone | 385.1 | 1.195 | 1 |
| [3-(5-chloro-2,4-dihydroxyphenyl)-1,4,6,7-tetrahydro-5H-pyrazolo[4,3-c]pyridin-5-yl](3-hydroxyphenyl)methanone | 386.08 | 0.899 | 1 |
| [3-(5-chloro-2,4-dihydroxyphenyl)-1,4,6,7-tetrahydro-5H-pyrazolo[4,3-c]pyridin-5-yl](4-hydroxyphenyl)methanone | 386.08 | 1.355 | 1 |

-continued

| Name | M + H | RT | METHOD |
|---|---|---|---|
| (4-amino-1-methyl-1H-pyrrol-2-yl)[3-(5-chloro-2,4-dihydroxyphenyl)-1,4,6,7-tetrahydro-5H-pyrazolo[4,3-c]pyridin-5-yl]methanone | 388.11 | 1.211 | 1 |
| [3-(5-chloro-2,4-dihydroxyphenyl)-1,4,6,7-tetrahydro-5H-pyrazolo[4,3-c]pyridin-5-yl](5-methyl-2-thienyl)methanone | 390.06 | 1.176 | 1 |
| [3-(5-chloro-2,4-dihydroxyphenyl)-1,4,6,7-tetrahydro-5H-pyrazolo[4,3-c]pyridin-5-yl](1-methylpiperidin-4-yl)methanone | 391.15 | 0.647 | 1 |
| [3-(5-chloro-2,4-dihydroxyphenyl)-1,4,6,7-tetrahydro-5H-pyrazolo[4,3-c]pyridin-5-yl](4-hydroxycyclohexyl)methanone | 392.13 | 1.7 | 2 |
| 1-[3-(5-chloro-2,4-dihydroxyphenyl)-1,4,6,7-tetrahydro-5H-pyrazolo[4,3-c]pyridin-5-yl]-3-(diethylamino)propan-1-one | 393.16 | 0.683 | 1 |
| 4-{[3-(5-chloro-2,4-dihydroxyphenyl)-1,4,6,7-tetrahydro-5H-pyrazolo[4,3-c]pyridin-5-yl]carbonyl}benzonitrile | 395.08 | 1.023 | 1 |
| 3-{[3-(5-chloro-2,4-dihydroxyphenyl)-1,4,6,7-tetrahydro-5H-pyrazolo[4,3-c]pyridin-5-yl]carbonyl}benzonitrile | 395.08 | 1.021 | 1 |
| 1-[3-(5-chloro-2,4-dihydroxyphenyl)-1,4,6,7-tetrahydro-5H-pyrazolo[4,3-c]pyridin-5-yl]-2-(4-methylphenyl)ethanone | 398.12 | 0.893 | 1 |
| 2-(4-aminophenyl)-1-[3-(5-chloro-2,4-dihydroxyphenyl)-1,4,6,7-tetrahydro-5H-pyrazolo[4,3-c]pyridin-5-yl]ethanone | 399.11 | 1.187 | 1 |
| [3-(5-chloro-2,4-dihydroxyphenyl)-1,4,6,7-tetrahydro-5H-pyrazolo[4,3-c]pyridin-5-yl][4-(methylamino)phenyl]methanone | 399.11 | 0.884 | 1 |
| [4-(aminomethyl)phenyl][3-(5-chloro-2,4-dihydroxyphenyl)-1,4,6,7-tetrahydro-5H-pyrazolo[4,3-c]pyridin-5-yl]methanone | 399.11 | 1.211 | 1 |
| 2-anilino-1-[3-(5-chloro-2,4-dihydroxyphenyl)-1,4,6,7-tetrahydro-5H-pyrazolo[4,3-c]pyridin-5-yl]ethanone | 399.11 | 1.09 | 1 |
| [3-(5-chloro-2,4-dihydroxyphenyl)-1,4,6,7-tetrahydro-5H-pyrazolo[4,3-c]pyridin-5-yl][4-(hydroxymethyl)phenyl]methanone | 400.1 | 0.866 | 1 |
| [3-(5-chloro-2,4-dihydroxyphenyl)-1,4,6,7-tetrahydro-5H-pyrazolo[4,3-c]pyridin-5-yl](3-methoxyphenyl)methanone | 400.1 | 1.093 | 1 |
| [3-(5-chloro-2,4-dihydroxyphenyl)-1,4,6,7-tetrahydro-5H-pyrazolo[4,3-c]pyridin-5-yl](4-methoxyphenyl)methanone | 400.1 | 1.078 | 1 |
| [3-(5-chloro-2,4-dihydroxyphenyl)-1,4,6,7-tetrahydro-5H-pyrazolo[4,3-c]pyridin-5-yl](3,4-dihydroxyphenyl)methanone | 402.08 | 0.778 | 1 |
| 1-[3-(5-chloro-2,4-dihydroxyphenyl)-1,4,6,7-tetrahydro-5H-pyrazolo[4,3-c]pyridin-5-yl]-2-(4-fluorophenyl)ethanone | 402.09 | 1.186 | 1 |
| 1-[3-(5-chloro-2,4-dihydroxyphenyl)-1,4,6,7-tetrahydro-5H-pyrazolo[4,3-c]pyridin-5-yl]-2-(3-fluorophenyl)ethanone | 402.09 | 1.16 | 1 |
| [3-(5-chloro-2,4-dihydroxyphenyl)-1,4,6,7-tetrahydro-5H-pyrazolo[4,3-c]pyridin-5-yl](4-fluoro-3-hydroxyphenyl)methanone | 404.07 | 0.937 | 1 |
| 1-[3-(5-chloro-2,4-dihydroxyphenyl)-1,4,6,7-tetrahydro-5H-pyrazolo[4,3-c]pyridin-5-yl]-3-(piperidin-1-yl)propan-1-one | 405.16 | 0.74 | 1 |
| [3-(5-chloro-2,4-dihydroxyphenyl)-1,4,6,7-tetrahydro-5H-pyrazolo[4,3-c]pyridin-5-yl][(1S,3S)-3-methoxycyclohexyl]methanone | 406.15 | 1.012 | 1 |
| [3-(5-chloro-2,4-dihydroxyphenyl)-1,4,6,7-tetrahydro-5H-pyrazolo[4,3-c]pyridin-5-yl][(1S,3R)-3-methoxycyclohexyl]methanone | 406.15 | 1.085 | 1 |
| [3-(5-chloro-2,4-dihydroxyphenyl)-1,4,6,7-tetrahydro-5H-pyrazolo[4,3-c]pyridin-5-yl](trans-4-methoxycyclohexyl)methanone | 406.15 | 0.986 | 1 |
| [3-(5-chloro-2,4-dihydroxyphenyl)-1,4,6,7-tetrahydro-5H-pyrazolo[4,3-c]pyridin-5-yl](cis-4-methoxycyclohexyl)methanone | 406.15 | 1.036 | 1 |
| 4-{2-[3-(5-chloro-2,4-dihydroxyphenyl)-1,4,6,7-tetrahydro-5H-pyrazolo[4,3-c]pyridin-5-yl]-2-oxoethyl}benzonitrile | 409.1 | 1.104 | 1 |
| [3-(5-chloro-2,4-dihydroxyphenyl)-1,4,6,7-tetrahydro-5H-pyrazolo[4,3-c]pyridin-5-yl](1H-indol-5-yl)methanone | 409.1 | 0.995 | 1 |
| [3-(5-chloro-2,4-dihydroxyphenyl)-1,4,6,7-tetrahydro-5H-pyrazolo[4,3-c]pyridin-5-yl](1H-indol-6-yl)methanone | 409.1 | 1.064 | 1 |
| [3-(5-chloro-2,4-dihydroxyphenyl)-1,4,6,7-tetrahydro-5H-pyrazolo[4,3-c]pyridin-5-yl](1H-indol-3-yl)methanone | 409.1 | 1.514 | 1 |
| 1H-benzimidazol-5-yl[3-(5-chloro-2,4-dihydroxyphenyl)-1,4,6,7-tetrahydro-5H-pyrazolo[4,3-c]pyridin-5-yl]methanone | 410.09 | 0.668 | 1 |

-continued

| Name | M + H | RT | METHOD |
|---|---|---|---|
| [3-(5-chloro-2,4-dihydroxyphenyl)-1,4,6,7-tetrahydro-5H-pyrazolo[4,3-c]pyridin-5-yl](1H-indazol-3-yl)methanone | 410.09 | 1.048 | 1 |
| [3-(5-chloro-2,4-dihydroxyphenyl)-1,4,6,7-tetrahydro-5H-pyrazolo[4,3-c]pyridin-5-yl](1H-indazol-5-yl)methanone | 410.09 | 0.8466 | 1 |
| 1-[3-(5-chloro-2,4-dihydroxyphenyl)-1,4,6,7-tetrahydro-5H-pyrazolo[4,3-c]pyridin-5-yl]-2-(4-methoxyphenyl)ethanone | 414.11 | 1.147 | 1 |
| 1-[3-(5-chloro-2,4-dihydroxyphenyl)-1,4,6,7-tetrahydro-5H-pyrazolo[4,3-c]pyridin-5-yl]-2-[4-(hydroxymethyl)phenyl]ethanone | 414.11 | 1.206 | 1 |
| 1-[3-(5-chloro-2,4-dihydroxyphenyl)-1,4,6,7-tetrahydro-5H-pyrazolo[4,3-c]pyridin-5-yl]-2-(3-methoxyphenyl)ethanone | 414.11 | 1.102 | 1 |
| [3-(5-chloro-2,4-dihydroxyphenyl)-1,4,6,7-tetrahydro-5H-pyrazolo[4,3-c]pyridin-5-yl](4-nitrophenyl)methanone | 415.07 | 1.168 | 1 |
| (4-amino-3-methoxyphenyl)[3-(5-chloro-2,4-dihydroxyphenyl)-1,4,6,7-tetrahydro-5H-pyrazolo[4,3-c]pyridin-5-yl]methanone | 415.11 | 0.774 | 1 |
| [3-(5-chloro-2,4-dihydroxyphenyl)-1,4,6,7-tetrahydro-5H-pyrazolo[4,3-c]pyridin-5-yl][4-(methylthio)phenyl]methanone | 416.08 | 1.195 | 1 |
| [3-(5-chloro-2,4-dihydroxyphenyl)-1,4,6,7-tetrahydro-5H-pyrazolo[4,3-c]pyridin-5-yl](4-hydroxy-3-methoxyphenyl)methanone | 416.09 | 1.346 | 1 |
| N-{2-[3-(5-chloro-2,4-dihydroxyphenyl)-1,4,6,7-tetrahydro-5H-pyrazolo[4,3-c]pyridin-5-yl]-2-oxoethyl}-2-furamide | 417.09 | 0.85 | 1 |
| 1-[3-(5-chloro-2,4-dihydroxyphenyl)-1,4,6,7-tetrahydro-5H-pyrazolo[4,3-c]pyridin-5-yl]-2-(4-chlorophenyl)ethanone | 418.06 | 1.259 | 1 |
| 1-[3-(5-chloro-2,4-dihydroxyphenyl)-1,4,6,7-tetrahydro-5H-pyrazolo[4,3-c]pyridin-5-yl]-2-(3-chlorophenyl)ethanone | 418.06 | 1.25 | 1 |
| 1-(4-{[3-(5-chloro-2,4-dihydroxyphenyl)-1,4,6,7-tetrahydro-5H-pyrazolo[4,3-c]pyridin-5-yl]carbonyl}piperidin-1-yl)ethanone | 419.14 | 0.784 | 1 |
| tert-butyl {2-[3-(5-chloro-2,4-dihydroxyphenyl)-1,4,6,7-tetrahydro-5H-pyrazolo[4,3-c]pyridin-5-yl]-2-oxoethyl}carbamate | 423.14 | 1.01 | 1 |
| [3-(5-chloro-2,4-dihydroxyphenyl)-1,4,6,7-tetrahydro-5H-pyrazolo[4,3-c]pyridin-5-yl](5-hydroxy-1H-indol-2-yl)methanone | 425.09 | 0.906 | 1 |
| 1,3-benzothiazol-6-yl[3-(5-chloro-2,4-dihydroxyphenyl)-1,4,6,7-tetrahydro-5H-pyrazolo[4,3-c]pyridin-5-yl]methanone | 427.06 | 0.948 | 1 |
| [3-(5-chloro-2,4-dihydroxyphenyl)-1,4,6,7-tetrahydro-5H-pyrazolo[4,3-c]pyridin-5-yl](5-fluoro-1H-indol-2-yl)methanone | 427.09 | 1.239 | 1 |
| N-{2-[3-(5-chloro-2,4-dihydroxyphenyl)-1,4,6,7-tetrahydro-5H-pyrazolo[4,3-c]pyridin-5-yl]-2-oxoethyl}benzamide | 427.11 | 0.947 | 1 |
| 1-(4-{[3-(5-chloro-2,4-dihydroxyphenyl)-1,4,6,7-tetrahydro-5H-pyrazolo[4,3-c]pyridin-5-yl]carbonyl}phenyl)guanidine | 427.12 | 0.995 | 1 |
| 2-(1,3-benzodioxol-5-yl)-1-[3-(5-chloro-2,4-dihydroxyphenyl)-1,4,6,7-tetrahydro-5H-pyrazolo[4,3-c]pyridin-5-yl]ethanone | 428.09 | 1.101 | 1 |
| N-{2-[3-(5-chloro-2,4-dihydroxyphenyl)-1,4,6,7-tetrahydro-5H-pyrazolo[4,3-c]pyridin-5-yl]-2-oxoethyl}nicotinamide | 428.1 | 0.621 | 1 |
| 1-[3-(5-chloro-2,4-dihydroxyphenyl)-1,4,6,7-tetrahydro-5H-pyrazolo[4,3-c]pyridin-5-yl]-2-(4-nitrophenyl)ethanone | 429.09 | 1.183 | 1 |
| (2R)-2-amino-1-[3-(5-chloro-2,4-dihydroxyphenyl)-1,4,6,7-tetrahydro-5H-pyrazolo[4,3-c]pyridin-5-yl]-3-(4-hydroxyphenyl)propan-1-one | 429.13 | 1.807 | 1 |
| (2S)-2-amino-1-[3-(5-chloro-2,4-dihydroxyphenyl)-1,4,6,7-tetrahydro-5H-pyrazolo[4,3-c]pyridin-5-yl]-3-(4-hydroxyphenyl)propan-1-one | 429.13 | 1.535 | 1 |
| 1-[3-(5-chloro-2,4-dihydroxyphenyl)-1,4,6,7-tetrahydro-5H-pyrazolo[4,3-c]pyridin-5-yl]-2-[4-(methylthio)phenyl]ethanone | 430.09 | 1.246 | 1 |
| 1-[3-(5-chloro-2,4-dihydroxyphenyl)-1,4,6,7-tetrahydro-5H-pyrazolo[4,3-c]pyridin-5-yl]-2-[3-(methylthio)phenyl]ethanone | 430.09 | 1.219 | 1 |
| 1-[3-(5-chloro-2,4-dihydroxyphenyl)-1,4,6,7-tetrahydro-5H-pyrazolo[4,3-c]pyridin-5-yl]-2-(2-naphthyl)ethanone | 434.12 | 1.295 | 1 |

-continued

| Name | M + H | RT | METHOD |
|---|---|---|---|
| [3-(5-chloro-2,4-dihydroxyphenyl)-1,4,6,7-tetrahydro-5H-pyrazolo[4,3-c]pyridin-5-yl][4-(1H-pyrrol-1-yl)phenyl]methanone | 435.11 | 1.273 | 1 |
| [3-(5-chloro-2,4-dihydroxyphenyl)-1,4,6,7-tetrahydro-5H-pyrazolo[4,3-c]pyridin-5-yl][3-(1H-pyrrol-1-yl)phenyl]methanone | 435.11 | 1.275 | 1 |
| [3-(5-chloro-2,4-dihydroxyphenyl)-1,4,6,7-tetrahydro-5H-pyrazolo[4,3-c]pyridin-5-yl][4-(1H-imidazol-1-yl)phenyl]methanone | 436.11 | 0.759 | 1 |
| [3-(5-chloro-2,4-dihydroxyphenyl)-1,4,6,7-tetrahydro-5H-pyrazolo[4,3-c]pyridin-5-yl][3-(1H-imidazol-1-yl)phenyl]methanone | 436.11 | 0.863 | 1 |
| [3-(5-chloro-2,4-dihydroxyphenyl)-1,4,6,7-tetrahydro-5H-pyrazolo[4,3-c]pyridin-5-yl][4-(1,3-oxazol-5-yl)phenyl]methanone | 437.09 | 0.998 | 1 |
| [3-(5-chloro-2,4-dihydroxyphenyl)-6,7-dihydroisoxazolo[4,3-c]pyridin-5(4H)-yl][3-(1H-imidazol-1-yl)phenyl]methanone | 437.09 | 0.914 | 1 |
| tert-butyl {2-[3-(5-chloro-2,4-dihydroxyphenyl)-1,4,6,7-tetrahydro-5H-pyrazolo[4,3-c]pyridin-5-yl]-2-oxoethyl}methylcarbamate | 437.15 | 1.05 | 1 |
| [3-(5-chloro-2,4-dihydroxyphenyl)-1,4,6,7-tetrahydro-5H-pyrazolo[4,3-c]pyridin-5-yl][3-(trifluoromethyl)phenyl]methanone | 438.08 | 1.282 | 1 |
| [3-(5-chloro-2,4-dihydroxyphenyl)-1,4,6,7-tetrahydro-5H-pyrazolo[4,3-c]pyridin-5-yl][4-(trifluoromethyl)phenyl]methanone | 438.08 | 1.296 | 1 |
| 3-{2-[3-(5-chloro-2,4-dihydroxyphenyl)-1,4,6,7-tetrahydro-5H-pyrazolo[4,3-c]pyridin-5-yl]-2-oxoethyl}-2-thioxo-1,3-thiazolidin-4-one | 439.02 | 1.03 | 1 |
| [3-(5-chloro-2,4-dihydroxyphenyl)-1,4,6,7-tetrahydro-5H-pyrazolo[4,3-c]pyridin-5-yl](5-methoxy-1H-indol-2-yl)methanone | 439.11 | 1.172 | 1 |
| N-{3-[3-(5-chloro-2,4-dihydroxyphenyl)-1,4,6,7-tetrahydro-5H-pyrazolo[4,3-c]pyridin-5-yl]-3-oxopropyl}benzamide | 441.13 | 0.921 | 1 |
| N-{2-[3-(5-chloro-2,4-dihydroxyphenyl)-1,4,6,7-tetrahydro-5H-pyrazolo[4,3-c]pyridin-5-yl]-2-oxoethyl}-2-phenylacetamide | 441.13 | 0.983 | 1 |
| N-{2-[3-(5-chloro-2,4-dihydroxyphenyl)-1,4,6,7-tetrahydro-5H-pyrazolo[4,3-c]pyridin-5-yl]-2-oxoethyl}-2-methylbenzamide | 441.13 | 1.01 | 1 |
| N-{2-[3-(5-chloro-2,4-dihydroxyphenyl)-1,4,6,7-tetrahydro-5H-pyrazolo[4,3-c]pyridin-5-yl]-2-oxoethyl}-3-methylbenzamide | 441.13 | 1.06 | 1 |
| N-{2-[3-(5-chloro-2,4-dihydroxyphenyl)-1,4,6,7-tetrahydro-5H-pyrazolo[4,3-c]pyridin-5-yl]-2-oxoethyl}-4-methylbenzamide | 441.13 | 1.056 | 1 |
| (4-aminophenyl){3-(5-chloro-2,4-dihydroxyphenyl)-1-[(dimethylamino)methyl]-1,4,6,7-tetrahydro-5H-pyrazolo[4,3-c]pyridin-5-yl}methanone | 442.16 | 1.175 | 1 |
| [3-(5-chloro-2,4-dihydroxyphenyl)-1,4,6,7-tetrahydro-5H-pyrazolo[4,3-c]pyridin-5-yl](5-chloro-1H-indol-2-yl)methanone | 443.06 | 1.354 | 1 |
| 1-[3-(5-chloro-2,4-dihydroxyphenyl)-1,4,6,7-tetrahydro-5H-pyrazolo[4,3-c]pyridin-5-yl]-2-[5-(pyrrolidin-1-yl)-2H-tetrazol-2-yl]ethanone | 445.14 | 1.008 | 1 |
| 4-{[3-(5-chloro-2,4-dihydroxyphenyl)-1,4,6,7-tetrahydro-5H-pyrazolo[4,3-c]pyridin-5-yl]carbonyl}benzenesulfonamide | 449.06 | 0.86 | 1 |
| 1-[3-(5-chloro-2,4-dihydroxyphenyl)-1,4,6,7-tetrahydro-5H-pyrazolo[4,3-c]pyridin-5-yl]-2-(3,4-dichlorophenyl)ethanone | 452.03 | 1.373 | 1 |
| 1-[3-(5-chloro-2,4-dihydroxyphenyl)-1,4,6,7-tetrahydro-5H-pyrazolo[4,3-c]pyridin-5-yl]-2-[4-(trifluoromethyl)phenyl]ethanone | 452.09 | 1.31 | 1 |
| 1-[3-(5-chloro-2,4-dihydroxyphenyl)-1,4,6,7-tetrahydro-5H-pyrazolo[4,3-c]pyridin-5-yl]-2-[3-(trifluoromethyl)phenyl]ethanone | 452.09 | 1.323 | 1 |
| 2-{2-[3-(5-chloro-2,4-dihydroxyphenyl)-1,4,6,7-tetrahydro-5H-pyrazolo[4,3-c]pyridin-5-yl]-2-oxoethyl}-1H-isoindole-1,3(2H)-dione | 453.09 | 1.05 | 1 |
| [3-(5-chloro-2,4-dihydroxyphenyl)-1,4,6,7-tetrahydro-5H-pyrazolo[4,3-c]pyridin-5-yl][4-(trifluoromethoxy)phenyl]methanone | 454.07 | 1.334 | 1 |
| [3-(5-chloro-2,4-dihydroxyphenyl)-1,4,6,7-tetrahydro-5H-pyrazolo[4,3-c]pyridin-5-yl][3-(trifluoromethoxy)phenyl]methanone | 454.07 | 1.323 | 1 |

-continued

| Name | M + H | RT | METHOD |
|---|---|---|---|
| [3-(5-chloro-2,4-dihydroxyphenyl)-1,4,6,7-tetrahydro-5H-pyrazolo[4,3-c]pyridin-5-yl][2-(pyridin-3-yl)-1,3-thiazol-4-yl]methanone | 454.07 | 0.826 | 1 |
| 2-(4-aminophenyl)-1-{3-(5-chloro-2,4-dihydroxyphenyl)-1-[(dimethylamino)methyl]-1,4,6,7-tetrahydro-5H-pyrazolo[4,3-c]pyridin-5-yl}ethanone | 456.17 | 1.19 | 1 |
| benzyl {2-[3-(5-chloro-2,4-dihydroxyphenyl)-1,4,6,7-tetrahydro-5H-pyrazolo[4,3-c]pyridin-5-yl]-2-oxoethyl}carbamate | 457.12 | 1.103 | 1 |
| 2-(biphenyl-4-yl)-1-[3-(5-chloro-2,4-dihydroxyphenyl)-1,4,6,7-tetrahydro-5H-pyrazolo[4,3-c]pyridin-5-yl]ethanone | 460.13 | 1.409 | 1 |
| 2-(4-bromophenyl)-1-[3-(5-chloro-2,4-dihydroxyphenyl)-1,4,6,7-tetrahydro-5H-pyrazolo[4,3-c]pyridin-5-yl]ethanone | 462.01 | 1.29 | 1 |
| 2-(3-bromophenyl)-1-[3-(5-chloro-2,4-dihydroxyphenyl)-1,4,6,7-tetrahydro-5H-pyrazolo[4,3-c]pyridin-5-yl]ethanone | 462.01 | 1.276 | 1 |
| ethanone, 1-[3-(5-chloro-2,4-dihydroxyphenyl)-1,4,6,7-tetrahydro-5H-pyrazolo[4,3-c]pyridin-5-yl]-2-[4-(methylsulfonyl)phenyl]- | 462.08 | 0.961 | 1 |
| [3-(5-chloro-2,4-dihydroxyphenyl)-1,4,6,7-tetrahydro-5H-pyrazolo[4,3-c]pyridin-5-yl](4-phenoxyphenyl)methanone | 462.11 | 1.38 | 1 |
| [3-(5-chloro-2,4-dihydroxyphenyl)-1,4,6,7-tetrahydro-5H-pyrazolo[4,3-c]pyridin-5-yl](3-phenoxyphenyl)methanone | 462.11 | 1.385 | 1 |
| 1-[3-(5-chloro-2,4-dihydroxyphenyl)-1,4,6,7-tetrahydro-5H-pyrazolo[4,3-c]pyridin-5-yl]-2-[4-(trifluoromethoxy)phenyl]ethanone | 468.09 | 1.364 | 1 |
| [3-(5-chloro-2,4-dihydroxyphenyl)-1,4,6,7-tetrahydro-5H-pyrazolo[4,3-c]pyridin-5-yl][6-(2,2,2-trifluoroethoxy)pyridin-3-yl]methanone | 469.08 | 1.278 | 1 |
| [4-amino-3-(trifluoromethoxy)phenyl][3-(5-chloro-2,4-dihydroxyphenyl)-1,4,6,7-tetrahydro-5H-pyrazolo[4,3-c]pyridin-5-yl]methanone | 469.08 | 1.122 | 1 |
| N-{2-[3-(5-chloro-2,4-dihydroxyphenyl)-1,4,6,7-tetrahydro-5H-pyrazolo[4,3-c]pyridin-5-yl]-2-oxoethyl}-4-nitrobenzamide | 472.09 | 0.998 | 1 |
| (3-benzoylphenyl)[3-(5-chloro-2,4-dihydroxyphenyl)-1,4,6,7-tetrahydro-5H-pyrazolo[4,3-c]pyridin-5-yl]methanone | 474.11 | 1.277 | 1 |
| [4-(benzyloxy)phenyl][3-(5-chloro-2,4-dihydroxyphenyl)-1,4,6,7-tetrahydro-5H-pyrazolo[4,3-c]pyridin-5-yl]methanone | 476.13 | 1.392 | 1 |
| N-{2-[3-(5-chloro-2,4-dihydroxyphenyl)-1,4,6,7-tetrahydro-5H-pyrazolo[4,3-c]pyridin-5-yl]-2-oxoethyl}-4-methylbenzenesulfonamide | 477.09 | 1.06 | 1 |
| 2-chloro-5-{[3-(5-chloro-2,4-dihydroxyphenyl)-1,4,6,7-tetrahydro-5H-pyrazolo[4,3-c]pyridin-5-yl]carbonyl}benzenesulfonamide | 483.02 | 0.935 | 1 |
| 1-[3-(5-chloro-2,4-dihydroxyphenyl)-1,4,6,7-tetrahydro-5H-pyrazolo[4,3-c]pyridin-5-yl]-2-[4-(phenoxymethyl)phenyl]ethanone | 490.15 | 1.44 | 1 |
| 2-[3-(benzyloxy)phenyl]-1-[3-(5-chloro-2,4-dihydroxyphenyl)-1,4,6,7-tetrahydro-5H-pyrazolo[4,3-c]pyridin-5-yl]ethanone | 490.15 | 1.396 | 1 |
| 5-bromo-N-{2-[3-(5-chloro-2,4-dihydroxyphenyl)-1,4,6,7-tetrahydro-5H-pyrazolo[4,3-c]pyridin-5-yl]-2-oxoethyl}-2-furamide | 495 | 1.124 | 1 |
| 1-[3-(5-chloro-2,4-dihydroxyphenyl)-1,4,6,7-tetrahydro-5H-pyrazolo[4,3-c]pyridin-5-yl]-2-{4-[(4-methylpiperazin-1-yl)methyl]phenyl}ethanone | 496.2 | 0.681 | 1 |
| [3-(5-chloro-2,4-dihydroxyphenyl)-1,4,6,7-tetrahydro-5H-pyrazolo[4,3-c]pyridin-5-yl][4-(1,1-dioxidothiomorpholin-4-yl)phenyl]methanone | 503.11 | 0.996 | 1 |
| 4-bromo-N-{2-[3-(5-chloro-2,4-dihydroxyphenyl)-1,4,6,7-tetrahydro-5H-pyrazolo[4,3-c]pyridin-5-yl]-2-oxoethyl}benzamide | 505.02 | 1.18 | 1 |
| 4-{[3-(5-chloro-2,4-dihydroxyphenyl)-1,4,6,7-tetrahydro-5H-pyrazolo[4,3-c]pyridin-5-yl]carbonyl}-N,N-diethylbenzenesulfonamide | 505.12 | 1.123 | 1 |
| 1-[3-(5-chloro-2,4-dihydroxyphenyl)-1,4,6,7-tetrahydro-5H-pyrazolo[4,3-c]pyridin-5-yl]-2-{4-[(2-fluorophenoxy)methyl]phenyl}ethanone | 508.14 | 1.44 | 1 |
| 1-[3-(5-chloro-2,4-dihydroxyphenyl)-1,4,6,7-tetrahydro-5H-pyrazolo[4,3-c]pyridin-5-yl]-2-(2-iodophenyl)ethanone | 510 | 1.28 | 1 |
| [3-(5-chloro-2,4-dihydroxyphenyl)-1,4,6,7-tetrahydro-5H-pyrazolo[4,3-c]pyridin-5-yl]{4-[(1,1-dioxidothiomorpholin-4-yl)methyl]phenyl}methanone | 517.12 | 0.778 | 1 |

-continued

| Name | M + H | RT | METHOD |
|---|---|---|---|
| 1-(4-{[3-(5-chloro-2,4-dihydroxyphenyl)-1,4,6,7-tetrahydro-5H-pyrazolo[4,3-c]pyridin-5-yl]carbonyl}phenyl)-3-(2-methylphenyl)urea | 518.15 | 1.211 | 1 |
| 1-(3-{[3-(5-chloro-2,4-dihydroxyphenyl)-1,4,6,7-tetrahydro-5H-pyrazolo[4,3-c]pyridin-5-yl]carbonyl}phenyl)-3-(2-fluorophenyl)urea | 522.13 | 1.22 | 1 |
| 1-(3-{[3-(5-chloro-2,4-dihydroxyphenyl)-1,4,6,7-tetrahydro-5H-pyrazolo[4,3-c]pyridin-5-yl]carbonyl}phenyl)-3-(2-chloro-6-methylphenyl)urea | 552.11 | 1.379 | 1 |
| N-(4-{2-[3-(5-chloro-2,4-dihydroxyphenyl)-1,4,6,7-tetrahydro-5H-pyrazolo[4,3-c]pyridin-5-yl]-2-oxoethyl}phenyl)-3-(trifluoromethyl)benzenesulfonamide | 607.1 | 1.293 | 1 |

| Name | ION | HRMS (ESI): Exact Mass Calc | HRMS (ESI): Exact Mass Found |
|---|---|---|---|
| 4-chloro-6-(5-{[4-(dimethylamino)phenyl]acetyl}-4,5,6,7-tetrahydro-1H-pyrazolo[4,3-c]pyridin-3-yl)benzene-1,3-diol | M + H | 427.1532 | 427.1539 |
| N-(4-{[3-(5-chloro-2,4-dihydroxyphenyl)-1,4,6,7-tetrahydro-5H-pyrazolo[4,3-c]pyridin-5-yl]carbonyl}phenyl)acetamide | M + H | 427.1168 | 427.1183 |
| 4-chloro-6-(5-{[4-(dimethylamino)phenyl]carbonyl}-4,5,6,7-tetrahydro-1H-pyrazolo[4,3-c]pyridin-3-yl)benzene-1,3-diol | M + H | 413.1375 | 413.1393 |
| 4-chloro-6-(5-{[3-(dimethylamino)phenyl]carbonyl}-4,5,6,7-tetrahydro-1H-pyrazolo[4,3-c]pyridin-3-yl)benzene-1,3-diol | M + H | 413.1375 | 413.1383 |
| 4-(5-beta-alanyl-4,5,6,7-tetrahydro-1H-pyrazolo[4,3-c]pyridin-3-yl)-6-chlorobenzene-1,3-diol hydrochloride | M + H | 337.1062 | 337.1067 |
| 4-[5-(4-aminobutanoyl)-4,5,6,7-tetrahydro-1H-pyrazolo[4,3-c]pyridin-3-yl]-6-chlorobenzene-1,3-diol hydrochloride | M + H | 351.1219 | 351.1233 |
| 4-chloro-6-{5-[(4-morpholin-4-ylphenyl)carbonyl]-4,5,6,7-tetrahydro-1H-pyrazolo[4,3-c]pyridin-3-yl}benzene-1,3-diol | M + H | 455.1481 | 455.1503 |
| 4-chloro-6-(5-{[4-(4-methylpiperazin-1-yl)phenyl]carbonyl}-4,5,6,7-tetrahydro-1H-pyrazolo[4,3-c]pyridin-3-yl)benzene-1,3-diol | M + H | 468.1797 | 468.1806 |
| 4-chloro-6-{5-[(phenylcarbonyl)-4,5,6,7-tetrahydro-1H-pyrazolo[4,3-c]pyridin-3-yl]benzene-1,3-diol | M + H | 370.0953 | 370.0956 |
| 4-chloro-6-(5-{[3-(4-methylpiperazin-1-yl)phenyl]carbonyl}-4,5,6,7-tetrahydro-1H-pyrazolo[4,3-c]pyridin-3-yl)benzene-1,3-diol | M + H | 468.1797 | 468.1804 |
| 4-chloro-6-[5-(cyclohexylcarbonyl)-4,5,6,7-tetrahydro-1H-pyrazolo[4,3-c]pyridin-3-yl]benzene-1,3-diol | M + H | 376.1423 | 376.1437 |
| 4-(5-{[trans-4-(aminomethyl)cyclohexyl]carbonyl}-4,5,6,7-tetrahydro-1H-pyrazolo[4,3-c]pyridin-3-yl)-6-chlorobenzene-1,3-diol hydrochloride | M + H | 405.1688 | 405.1702 |
| 4-chloro-6-{5-[(trans-4-hydroxycyclohexyl)carbonyl]-4,5,6,7-tetrahydro-1H-pyrazolo[4,3-c]pyridin-3-yl}benzene-1,3-diol | M + H | 392.1372 | 392.1365 |
| 4-chloro-6-[5-(3-morpholin-4-ylpropanoyl)-4,5,6,7-tetrahydro-1H-pyrazolo[4,3-c]pyridin-3-yl]benzene-1,3-diol | M + H | 407.1481 | 407.1484 |
| 4-{[3-(5-chloro-2,4-dihydroxyphenyl)-1,4,6,7-tetrahydro-5H-pyrazolo[4,3-c]pyridin-5-yl]carbonyl}cyclohexanone | M + H | 390.1215 | 390.1212 |
| 4-chloro-6-{5-[(cis-4-methoxycyclohexyl)carbonyl]-4,5,6,7-tetrahydro-1H-pyrazolo[4,3-c]pyridin-3-yl}benzene-1,3-diol | M + H | 406.1528 | 406.1531 |
| 4-chloro-6-{5-[(trans-4-methoxycyclohexyl)carbonyl]-4,5,6,7-tetrahydro-1H-pyrazolo[4,3-c]pyridin-3-yl}benzene-1,3-diol | M + H | 406.1528 | 406.1538 |
| 4-chloro-6-(5-{[4-(morpholin-4-ylmethyl)phenyl]acetyl}-4,5,6,7-tetrahydro-1H-pyrazolo[4,3-c]pyridin-3-yl)benzene-1,3-diol | M + H | 483.1794 | 483.1796 |

Example 12

Preparation of [3-(5-chloro-2,4-dihydroxyphenyl)-6,7-dihydroisoxazolo[4,3-c]pyridin-5(4H)-yl](1H-imidazol-4-yl)methanone [(1), A=Cl, X=O, R=COC$_3$H$_3$N$_2$, m=1 n=1]

Step k1

4-[3-(5-Chloro-2,4-dihydroxy-phenyl)-6,7-dihydro-4H-isoxazolo[4,3-c]pyridine-5-carbonyl]-imidazole-1-carboxylic acid tert-butyl ester [(1), A=Cl, X=O, R=COC$_8$H$_{11}$N$_2$, m=1 n=1]

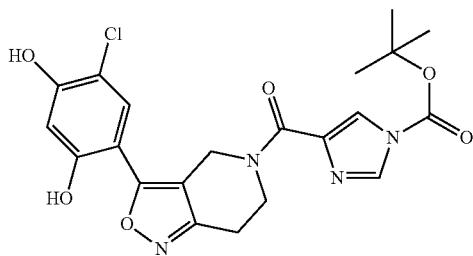

To a suspension of 1-(tert-butoxycarbonyl)-1H-imidazole-4-carboxylic acid (0.024 g, 0.11 mmol) in N,N'-dimethylacetamide (DMA) (0.5 mL), TBTU (0.035 g, 0.11 mmol) and DIPEA (0.017 mL, 1.8 mmol) were added all in a 1 dram vial (4 mL working volume). The mixture was stirred at room temperature for 30 minutes. Then 4-chloro-6-(4,5,6,7-tetrahydroisoxazolo[4,3-c]pyridin-3-yl)benzene-1,3-diol (0.024 g, 0.9 mmol), dissolved in DMA (0.5 mL) was added and the reaction was stirred for an additional 16 h at room temperature. HPLC analysis after 16 h indicated the conversion of the starting material to product. The solvent was removed in vacuo.

Step c2

[3-(5-chloro-2,4-dihydroxyphenyl)-6,7-dihydroisoxazolo[4,3-c]pyridin-5(4H)-yl](1H-imidazol-4-yl)methanone [(1), A=Cl, X=O, R=COC$_3$H$_3$N$_2$, m=1 n=1]

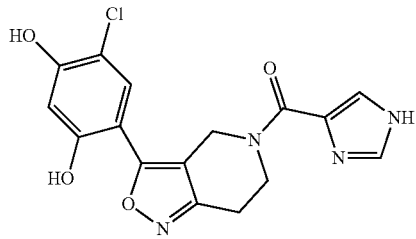

To the 4-[3-(5-Chloro-2,4-dihydroxy-phenyl)-6,7-dihydro-4H-isoxazolo[4,3-c]pyridine-5-carbonyl]-imidazole-1-carboxylic acid tert-butyl ester prepared in Step 1, a solution of TFA/DCM (1:1) (0.5 mL) was charged to the vial and stirred for 1 h at room temperature. The solvent was then removed in vacuo and the product was purified via semi-preparative HPLC according to the protocol indicated below.

In the case where the protection for the amine was an Fmoc group, a solution of 10% piperidine in DMF (0.5 mL) of was added to the vial, which was then stirred for 1 h. The solvent was then removed in vacuo and the product was purified via semi-preparative HPLC according to the protocol indicated below.

In the case where a tert-butyldimethylsilyl (TBDMS) protecting group existed, a 2N NaOH solution (0.2 mL) of was added to the reaction cocktail in Step 1, and agitated for 2 h at ambient. After the 2 hour NaOH treatment, a solution of 2N HCl (0.2 mL) was added to neutralize the solution. The solvent was then removed in vacuo and the product was purified via semi-preparative HPLC according to the protocol indicated below.

By working analogously and in parallel, the following compounds were prepared:

| Name | M + H | RT | METHOD |
|---|---|---|---|
| [3-(5-chloro-2,4-dihydroxyphenyl)-6,7-dihydroisoxazolo[4,3-c]pyridin-5(4H)-yl][3-(1H-imidazol-1-yl)phenyl]methanone | 437.09 | 0.914 | 1 |
| [3-(5-chloro-2,4-dihydroxyphenyl)-6,7-dihydroisoxazolo[4,3-c]pyridin-5(4H)-yl](1H-pyrrol-3-yl)methanone | 360.07 | 0.99 | 1 |
| [3-(5-chloro-2,4-dihydroxyphenyl)-6,7-dihydroisoxazolo[4,3-c]pyridin-5(4H)-yl](1H-pyrazol-4-yl)methanone | 361.06 | 0.903 | 1 |
| [3-(5-chloro-2,4-dihydroxyphenyl)-6,7-dihydroisoxazolo[4,3-c]pyridin-5(4H)-yl](4-hydroxyphenyl)methanone | 361.06 | 1.297 | 1 |
| [3-(5-chloro-2,4-dihydroxyphenyl)-6,7-dihydroisoxazolo[4,3-c]pyridin-5(4H)-yl][(2S)-2,5-dihydro-1H-pyrrol-2-yl]methanone | 362.08 | 0.861 | 1 |
| [3-(5-chloro-2,4-dihydroxyphenyl)-6,7-dihydroisoxazolo[4,3-c]pyridin-5(4H)-yl][(2S)-pyrrolidin-2-yl]methanone | 364.1 | 1.218 | 1 |
| [3-(5-chloro-2,4-dihydroxyphenyl)-6,7-dihydroisoxazolo[4,3-c]pyridin-5(4H)-yl][(2R)-pyrrolidin-2-yl]methanone | 364.1 | 1.218 | 1 |
| [3-(5-chloro-2,4-dihydroxyphenyl)-6,7-dihydroisoxazolo[4,3-c]pyridin-5(4H)-yl](pyridin-4-yl)methanone | 372.07 | 0.814 | 1 |
| [3-(5-chloro-2,4-dihydroxyphenyl)-6,7-dihydroisoxazolo[4,3-c]pyridin-5(4H)-yl](pyridin-3-yl)methanone | 372.07 | 0.831 | 1 |
| [3-(5-chloro-2,4-dihydroxyphenyl)-6,7-dihydroisoxazolo[4,3-c]pyridin-5(4H)-yl](3-thienyl)methanone | 377.03 | 1.122 | 1 |
| (3-amino-1H-1,2,4-triazol-5-yl)[3-(5-chloro-2,4-dihydroxyphenyl)-6,7-dihydroisoxazolo[4,3-c]pyridin-5(4H)-yl]methanone | 377.07 | 0.581 | 1 |
| [3-(5-chloro-2,4-dihydroxyphenyl)-6,7-dihydroisoxazolo[4,3-c]pyridin-5(4H)-yl](1,3-thiazol-4-yl)methanone | 378.02 | 0.991 | 1 |
| [3-(5-chloro-2,4-dihydroxyphenyl)-6,7-dihydroisoxazolo[4,3-c]pyridin-5(4H)-yl](piperidin-4-yl)methanone | 378.11 | 1.333 | 1 |

-continued

| Name | M + H | RT | METHOD |
|---|---|---|---|
| [3-(5-chloro-2,4-dihydroxyphenyl)-6,7-dihydroisoxazolo[4,3-c]pyridin-5(4H)-yl](piperidin-3-yl)methanone | 378.11 | 1.357 | 1 |
| [3-(5-chloro-2,4-dihydroxyphenyl)-6,7-dihydroisoxazolo[4,3-c]pyridin-5(4H)-yl][(2S,4R)-4-hydroxypyrrolidin-2-yl]methanone | 380.09 | 0.817 | 1 |
| [3-(5-chloro-2,4-dihydroxyphenyl)-6,7-dihydroisoxazolo[4,3-c]pyridin-5(4H)-yl][(2S,4S)-4-hydroxypyrrolidin-2-yl]methanone | 380.09 | 0.456 | 1 |
| [3-(5-chloro-2,4-dihydroxyphenyl)-6,7-dihydroisoxazolo[4,3-c]pyridin-5(4H)-yl][(2S,3S)-3-hydroxypyrrolidin-2-yl]methanone | 380.09 | 1.079 | 1 |
| (3-aminophenyl)[3-(5-chloro-2,4-dihydroxyphenyl)-6,7-dihydroisoxazolo[4,3-c]pyridin-5(4H)-yl]methanone | 386.08 | 0.896 | 1 |
| (4-aminophenyl)[3-(5-chloro-2,4-dihydroxyphenyl)-6,7-dihydroisoxazolo[4,3-c]pyridin-5(4H)-yl]methanone | 386.08 | 1.373 | 1 |
| [3-(5-chloro-2,4-dihydroxyphenyl)-6,7-dihydroisoxazolo[4,3-c]pyridin-5(4H)-yl](3-hydroxyphenyl)methanone | 387.07 | 1.068 | 1 |
| [3-(5-chloro-2,4-dihydroxyphenyl)-6,7-dihydroisoxazolo[4,3-c]pyridin-5(4H)-yl](4-hydroxyphenyl)methanone | 387.07 | 1.455 | 1 |
| (6-aminopyridin-3-yl)[3-(5-chloro-2,4-dihydroxyphenyl)-6,7-dihydroisoxazolo[4,3-c]pyridin-5(4H)-yl]methanone | 387.08 | 0.799 | 1 |
| [3-(5-chloro-2,4-dihydroxyphenyl)-6,7-dihydroisoxazolo[4,3-c]pyridin-5(4H)-yl](6-hydroxypyridin-3-yl)methanone | 388.06 | 0.841 | 1 |
| (4-amino-1-methyl-1H-pyrrol-2-yl)[3-(5-chloro-2,4-dihydroxyphenyl)-6,7-dihydroisoxazolo[4,3-c]pyridin-5(4H)-yl]methanone | 389.09 | 1.307 | 1 |
| (4-amino-1-methyl-1H-imidazol-2-yl)[3-(5-chloro-2,4-dihydroxyphenyl)-6,7-dihydroisoxazolo[4,3-c]pyridin-5(4H)-yl]methanone | 390.09 | 0.834 | 1 |
| [3-(5-chloro-2,4-dihydroxyphenyl)-6,7-dihydroisoxazolo[4,3-c]pyridin-5(4H)-yl](5-methyl-2-thienyl)methanone | 391.04 | 1.255 | 1 |
| [3-(5-chloro-2,4-dihydroxyphenyl)-6,7-dihydroisoxazolo[4,3-c]pyridin-5(4H)-yl](1-methylpiperidin-4-yl)methanone | 392.13 | 0.806 | 1 |
| [3-(5-chloro-2,4-dihydroxyphenyl)-6,7-dihydroisoxazolo[4,3-c]pyridin-5(4H)-yl](4-hydroxycyclohexyl)methanone | 393.11 | 1.9 | 2 |
| [3-(5-chloro-2,4-dihydroxyphenyl)-6,7-dihydroisoxazolo[4,3-c]pyridin-5(4H)-yl](4-chloro-1H-pyrrol-2-yl)methanone | 394.03 | 1.214 | 1 |
| 4-{[3-(5-chloro-2,4-dihydroxyphenyl)-6,7-dihydroisoxazolo[4,3-c]pyridin-5(4H)-yl]carbonyl}benzonitrile | 396.07 | 1.145 | 1 |
| 3-{[3-(5-chloro-2,4-dihydroxyphenyl)-6,7-dihydroisoxazolo[4,3-c]pyridin-5(4H)-yl]carbonyl}benzonitrile | 396.07 | 1.137 | 1 |
| (3-amino-4-methylphenyl)[3-(5-chloro-2,4-dihydroxyphenyl)-6,7-dihydroisoxazolo[4,3-c]pyridin-5(4H)-yl]methanone | 400.1 | 0.934 | 1 |
| (4-amino-3-methylphenyl)[3-(5-chloro-2,4-dihydroxyphenyl)-6,7-dihydroisoxazolo[4,3-c]pyridin-5(4H)-yl]methanone | 400.1 | 0.979 | 1 |
| [3-(5-chloro-2,4-dihydroxyphenyl)-6,7-dihydroisoxazolo[4,3-c]pyridin-5(4H)-yl][4-(methylamino)phenyl]methanone | 400.1 | 0.974 | 1 |
| [4-(aminomethyl)phenyl][3-(5-chloro-2,4-dihydroxyphenyl)-6,7-dihydroisoxazolo[4,3-c]pyridin-5(4H)-yl]methanone | 400.1 | 1.328 | 1 |
| [3-(5-chloro-2,4-dihydroxyphenyl)-6,7-dihydroisoxazolo[4,3-c]pyridin-5(4H)-yl][4-(hydroxymethyl)phenyl]methanone | 401.08 | 1.019 | 1 |
| [3-(5-chloro-2,4-dihydroxyphenyl)-6,7-dihydroisoxazolo[4,3-c]pyridin-5(4H)-yl](3-methoxyphenyl)methanone | 401.08 | 1.2 | 1 |
| [3-(5-chloro-2,4-dihydroxyphenyl)-6,7-dihydroisoxazolo[4,3-c]pyridin-5(4H)-yl](4-methoxyphenyl)methanone | 401.08 | 1.182 | 1 |
| [3-(5-chloro-2,4-dihydroxyphenyl)-6,7-dihydroisoxazolo[4,3-c]pyridin-5(4H)-yl](3,4-diaminophenyl)methanone | 401.09 | 0.819 | 1 |
| (3-amino-4-hydroxyphenyl)[3-(5-chloro-2,4-dihydroxyphenyl)-6,7-dihydroisoxazolo[4,3-c]pyridin-5(4H)-yl]methanone | 402.08 | 0.808 | 1 |
| (4-amino-3-hydroxyphenyl)[3-(5-chloro-2,4-dihydroxyphenyl)-6,7-dihydroisoxazolo[4,3-c]pyridin-5(4H)-yl]methanone | 402.08 | 0.821 | 1 |
| [3-(5-chloro-2,4-dihydroxyphenyl)-6,7-dihydroisoxazolo[4,3-c]pyridin-5(4H)-yl](3,4-dihydroxyphenyl)methanone | 403.06 | 0.938 | 1 |
| 1-[3-(5-chloro-2,4-dihydroxyphenyl)-6,7-dihydroisoxazolo[4,3-c]pyridin-5(4H)-yl]-2-(3-fluorophenyl)ethanone | 403.08 | 1.231 | 1 |
| [3-(5-chloro-2,4-dihydroxyphenyl)-6,7-dihydroisoxazolo[4,3-c]pyridin-5(4H)-yl](4-fluoro-3-hydroxyphenyl)methanone | 405.06 | 1.065 | 1 |
| [3-(5-chloro-2,4-dihydroxyphenyl)-6,7-dihydroisoxazolo[4,3-c]pyridin-5(4H)-yl][(1S,3R)-3-methoxycyclohexyl]methanone | 407.13 | 1.124 | 1 |
| [3-(5-chloro-2,4-dihydroxyphenyl)-6,7-dihydroisoxazolo[4,3-c]pyridin-5(4H)-yl](3-methoxycyclohexyl)methanone | 407.13 | 1.174 | 1 |
| [3-(5-chloro-2,4-dihydroxyphenyl)-6,7-dihydroisoxazolo[4,3-c]pyridin-5(4H)-yl](trans-4-methoxycyclohexyl)methanone | 407.13 | 1.105 | 1 |
| [3-(5-chloro-2,4-dihydroxyphenyl)-6,7-dihydroisoxazolo[4,3-c]pyridin-5(4H)-yl](cis-4-methoxycyclohexyl)methanone | 407.13 | 1.147 | 1 |
| [3-(5-chloro-2,4-dihydroxyphenyl)-6,7-dihydroisoxazolo[4,3-c]pyridin-5(4H)-yl](1H-indol-5-yl)methanone | 410.08 | 1.158 | 1 |
| [3-(5-chloro-2,4-dihydroxyphenyl)-6,7-dihydroisoxazolo[4,3-c]pyridin-5(4H)-yl](1H-indol-6-yl)methanone | 410.08 | 1.174 | 1 |
| [3-(5-chloro-2,4-dihydroxyphenyl)-6,7-dihydroisoxazolo[4,3-c]pyridin-5(4H)-yl](1H-indol-3-yl)methanone | 410.08 | 1.597 | 1 |

-continued

| Name | M + H | RT | METHOD |
|---|---|---|---|
| 1H-benzimidazol-5-yl[3-(5-chloro-2,4-dihydroxyphenyl)-6,7-dihydroisoxazolo[4,3-c]pyridin-5(4H)-yl]methanone | 411.08 | 0.822 | 1 |
| [3-(5-chloro-2,4-dihydroxyphenyl)-6,7-dihydroisoxazolo[4,3-c]pyridin-5(4H)-yl](1H-indazol-3-yl)methanone | 411.08 | 1.137 | 1 |
| [3-(5-chloro-2,4-dihydroxyphenyl)-6,7-dihydroisoxazolo[4,3-c]pyridin-5(4H)-yl](1H-indazol-5-yl)methanone | 411.08 | 0.99 | 1 |
| [3-(5-chloro-2,4-dihydroxyphenyl)-6,7-dihydroisoxazolo[4,3-c]pyridin-5(4H)-yl][3-(dimethylamino)phenyl]methanone | 414.11 | 0.961 | 1 |
| 1-[3-(5-chloro-2,4-dihydroxyphenyl)-6,7-dihydroisoxazolo[4,3-c]pyridin-5(4H)-yl]-2-(3-methoxyphenyl)ethanone | 415.1 | 1.19 | 1 |
| 1-[3-(5-chloro-2,4-dihydroxyphenyl)-6,7-dihydroisoxazolo[4,3-c]pyridin-5(4H)-yl]-2-[4-(hydroxymethyl)phenyl]ethanone | 415.1 | 0.973 | 1 |
| [3-(5-chloro-2,4-dihydroxyphenyl)-6,7-dihydroisoxazolo[4,3-c]pyridin-5(4H)-yl](4-nitrophenyl)methanone | 416.06 | 1.211 | 1 |
| (4-amino-3-methoxyphenyl)[3-(5-chloro-2,4-dihydroxyphenyl)-6,7-dihydroisoxazolo[4,3-c]pyridin-5(4H)-yl]methanone | 416.09 | 0.93 | 1 |
| [3-(5-chloro-2,4-dihydroxyphenyl)-6,7-dihydroisoxazolo[4,3-c]pyridin-5(4H)-yl][4-(methylthio)phenyl]methanone | 417.06 | 1.292 | 1 |
| [3-(5-chloro-2,4-dihydroxyphenyl)-6,7-dihydroisoxazolo[4,3-c]pyridin-5(4H)-yl](4-hydroxy-3-methoxyphenyl)methanone | 417.08 | 1.03 | 1 |
| 1-[3-(5-chloro-2,4-dihydroxyphenyl)-6,7-dihydroisoxazolo[4,3-c]pyridin-5(4H)-yl]-2-(3-chlorophenyl)ethanone | 419.05 | 1.311 | 1 |
| 1-(4-{[3-(5-chloro-2,4-dihydroxyphenyl)-6,7-dihydroisoxazolo[4,3-c]pyridin-5(4H)-yl]carbonyl}piperidin-1-yl)ethanone | 420.12 | 0.937 | 1 |
| [3-(5-chloro-2,4-dihydroxyphenyl)-6,7-dihydroisoxazolo[4,3-c]pyridin-5(4H)-yl](5-hydroxy-1H-indol-2-yl)methanone | 426.08 | 1.042 | 1 |
| 1,3-benzothiazol-6-yl[3-(5-chloro-2,4-dihydroxyphenyl)-6,7-dihydroisoxazolo[4,3-c]pyridin-5(4H)-yl]methanone | 428.04 | 1.088 | 1 |
| [3-(5-chloro-2,4-dihydroxyphenyl)-6,7-dihydroisoxazolo[4,3-c]pyridin-5(4H)-yl](5-fluoro-1H-indol-2-yl)methanone | 428.07 | 1.325 | 1 |
| N-(4-{[3-(5-chloro-2,4-dihydroxyphenyl)-6,7-dihydroisoxazolo[4,3-c]pyridin-5(4H)-yl]carbonyl}phenyl)acetamide | 428.09 | 0.981 | 1 |
| 1-(4-{[3-(5-chloro-2,4-dihydroxyphenyl)-6,7-dihydroisoxazolo[4,3-c]pyridin-5(4H)-yl]carbonyl}phenyl)guanidine | 428.1 | 1.387 | 1 |
| 1-[3-(5-chloro-2,4-dihydroxyphenyl)-6,7-dihydroisoxazolo[4,3-c]pyridin-5(4H)-yl]-2-(4-nitrophenyl)ethanone | 430.07 | 1.191 | 1 |
| (2R)-2-amino-1-[3-(5-chloro-2,4-dihydroxyphenyl)-6,7-dihydroisoxazolo[4,3-c]pyridin-5(4H)-yl]-3-(4-hydroxyphenyl)propan-1-one | 430.11 | 1.851 | 1 |
| (2S)-2-amino-1-[3-(5-chloro-2,4-dihydroxyphenyl)-6,7-dihydroisoxazolo[4,3-c]pyridin-5(4H)-yl]-3-(4-hydroxyphenyl)propan-1-one | 430.11 | 1.621 | 1 |
| 1-[3-(5-chloro-2,4-dihydroxyphenyl)-6,7-dihydroisoxazolo[4,3-c]pyridin-5(4H)-yl]-2-[3-(methylthio)phenyl]ethanone | 431.08 | 1.281 | 1 |
| [3-(5-chloro-2,4-dihydroxyphenyl)-6,7-dihydroisoxazolo[4,3-c]pyridin-5(4H)-yl][4-(1H-pyrrol-1-yl)phenyl]methanone | 436.1 | 1.361 | 1 |
| [3-(5-chloro-2,4-dihydroxyphenyl)-6,7-dihydroisoxazolo[4,3-c]pyridin-5(4H)-yl][3-(1H-pyrrol-1-yl)phenyl]methanone | 436.1 | 1.35 | 1 |
| [3-(5-chloro-2,4-dihydroxyphenyl)-6,7-dihydroisoxazolo[4,3-c]pyridin-5(4H)-yl][4-(1,3-oxazol-5-yl)phenyl]methanone | 438.08 | 1.121 | 1 |
| [3-(5-chloro-2,4-dihydroxyphenyl)-6,7-dihydroisoxazolo[4,3-c]pyridin-5(4H)-yl][3-(trifluoromethyl)phenyl]methanone | 439.06 | 1.362 | 1 |
| [3-(5-chloro-2,4-dihydroxyphenyl)-6,7-dihydroisoxazolo[4,3-c]pyridin-5(4H)-yl][4-(trifluoromethyl)phenyl]methanone | 439.06 | 1.381 | 1 |
| [3-(5-chloro-2,4-dihydroxyphenyl)-6,7-dihydroisoxazolo[4,3-c]pyridin-5(4H)-yl](5-methoxy-1H-indol-2-yl)methanone | 440.09 | 1.26 | 1 |
| [3-(5-chloro-2,4-dihydroxyphenyl)-6,7-dihydroisoxazolo[4,3-c]pyridin-5(4H)-yl](5-chloro-1H-indol-2-yl)methanone | 444.04 | 1.431 | 1 |
| 4-{[3-(5-chloro-2,4-dihydroxyphenyl)-6,7-dihydroisoxazolo[4,3-c]pyridin-5(4H)-yl]carbonyl}benzenesulfonamide | 450.04 | 0.97 | 1 |
| 1-[3-(5-chloro-2,4-dihydroxyphenyl)-6,7-dihydroisoxazolo[4,3-c]pyridin-5(4H)-yl]-2-(3,4-dichlorophenyl)ethanone | 453.01 | 1.412 | 1 |
| 1-[3-(5-chloro-2,4-dihydroxyphenyl)-6,7-dihydroisoxazolo[4,3-c]pyridin-5(4H)-yl]-2-[3-(trifluoromethyl)phenyl]ethanone | 453.08 | 1.381 | 1 |
| [3-(5-chloro-2,4-dihydroxyphenyl)-6,7-dihydroisoxazolo[4,3-c]pyridin-5(4H)-yl][4-(trifluoromethoxy)phenyl]methanone | 455.05 | 1.411 | 1 |
| [3-(5-chloro-2,4-dihydroxyphenyl)-6,7-dihydroisoxazolo[4,3-c]pyridin-5(4H)-yl][3-(trifluoromethoxy)phenyl]methanone | 455.05 | 1.403 | 1 |
| [3-(5-chloro-2,4-dihydroxyphenyl)-6,7-dihydroisoxazolo[4,3-c]pyridin-5(4H)-yl][2-(pyridin-3-yl)-1,3-thiazol-4-yl]methanone | 455.05 | 0.941 | 1 |
| [3-(5-chloro-2,4-dihydroxyphenyl)-6,7-dihydroisoxazolo[4,3-c]pyridin-5(4H)-yl][4-(morpholin-4-yl)phenyl]methanone | 456.12 | 1.122 | 1 |
| 2-(3-bromophenyl)-1-[3-(5-chloro-2,4-dihydroxyphenyl)-6,7-dihydroisoxazolo[4,3-c]pyridin-5(4H)-yl]ethanone | 463 | 1.341 | 1 |
| [3-(5-chloro-2,4-dihydroxyphenyl)-6,7-dihydroisoxazolo[4,3-c]pyridin-5(4H)-yl](4-phenoxyphenyl)methanone | 463.1 | 1.481 | 1 |
| [3-(5-chloro-2,4-dihydroxyphenyl)-6,7-dihydroisoxazolo[4,3-c]pyridin-5(4H)-yl](3-phenoxyphenyl)methanone | 463.1 | 1.47 | 1 |

-continued

| Name | M + H | RT | METHOD |
|---|---|---|---|
| [3-(5-chloro-2,4-dihydroxyphenyl)-6,7-dihydroisoxazolo[4,3-c]pyridin-5(4H)-yl][3-(4-methylpiperazin-1-yl)phenyl]methanone | 469.16 | 0.87 | 1 |
| [3-(5-chloro-2,4-dihydroxyphenyl)-6,7-dihydroisoxazolo[4,3-c]pyridin-5(4H)-yl][3-(4-methylpiperazin-1-yl)phenyl]methanone | 469.16 | 0.911 | 1 |
| [3-(5-chloro-2,4-dihydroxyphenyl)-6,7-dihydroisoxazolo[4,3-c]pyridin-5(4H)-yl][6-(2,2,2-trifluoroethoxy)pyridin-3-yl]methanone | 470.07 | 1.353 | 1 |
| [4-amino-3-(trifluoromethoxy)phenyl][3-(5-chloro-2,4-dihydroxyphenyl)-6,7-dihydroisoxazolo[4,3-c]pyridin-5(4H)-yl]methanone | 470.07 | 1.231 | 1 |
| (3-benzoylphenyl)[3-(5-chloro-2,4-dihydroxyphenyl)-6,7-dihydroisoxazolo[4,3-c]pyridin-5(4H)-yl]methanone | 475.1 | 1.352 | 1 |
| [4-(benzyloxy)phenyl][3-(5-chloro-2,4-dihydroxyphenyl)-6,7-dihydroisoxazolo[4,3-c]pyridin-5(4H)-yl]methanone | 477.11 | 1.491 | 1 |
| 2-chloro-5-{[3-(5-chloro-2,4-dihydroxyphenyl)-6,7-dihydroisoxazolo[4,3-c]pyridin-5(4H)-yl]carbonyl}benzenesulfonamide | 484.01 | 1.041 | 1 |
| [3-(5-chloro-2,4-dihydroxyphenyl)-6,7-dihydroisoxazolo[4,3-c]pyridin-5(4H)-yl][4-(1,1-dioxidothiomorpholin-4-yl)phenyl]methanone | 504.09 | 1.05 | 1 |
| 4-{[3-(5-chloro-2,4-dihydroxyphenyl)-6,7-dihydroisoxazolo[4,3-c]pyridin-5(4H)-yl]carbonyl}-N,N-diethylbenzenesulfonamide | 506.11 | 1.311 | 1 |
| 1-[3-(5-chloro-2,4-dihydroxyphenyl)-6,7-dihydroisoxazolo[4,3-c]pyridin-5(4H)-yl]-2-(2-iodophenyl)ethanone | 510.98 | 1.352 | 1 |
| [3-(5-chloro-2,4-dihydroxyphenyl)-6,7-dihydroisoxazolo[4,3-c]pyridin-5(4H)-yl]{4-[(1,1-dioxidothiomorpholin-4-yl)methyl]phenyl}methanone | 518.11 | 0.921 | 1 |
| 1-(4-{[3-(5-chloro-2,4-dihydroxyphenyl)-6,7-dihydroisoxazolo[4,3-c]pyridin-5(4H)-yl]carbonyl}phenyl)-3-(2-methylphenyl)urea | 519.14 | 1.303 | 1 |
| 1-(3-{[3-(5-chloro-2,4-dihydroxyphenyl)-6,7-dihydroisoxazolo[4,3-c]pyridin-5(4H)-yl]carbonyl}phenyl)-3-(2-chloro-6-methylphenyl)urea | 553.1 | 1.421 | 1 |

| Name | ION | HRMS (ESI): EMASS CALC | HRMS (ESI): EMASS FOUND |
|---|---|---|---|
| 4-chloro-6-[5-(phenylcarbonyl)-4,5,6,7-tetrahydroisoxazolo[4,3-c]pyridin-3-yl]benzene-1,3-diol | M + H | 371.0793 | 371.0787 |
| 4-chloro-6-(5-{[4-(dimethylamino)phenyl]carbonyl}-4,5,6,7-tetrahydroisoxazolo[4,3-c]pyridin-3-yl)benzene-1,3-diol | M + H | 414.1215 | 414.1201 |
| 4-chloro-6-(5-{[4-(methylsulfonyl)phenyl]acetyl}-4,5,6,7-tetrahydroisoxazolo[4,3-c]pyridin-3-yl)benzene-1,3-diol | M + H | 463.0725 | 463.0712 |
| 4-chloro-6-[5-({4-[(dimethylamino)methyl]phenyl}carbonyl)-4,5,6,7-tetrahydroisoxazolo[4,3-c]pyridin-3-yl]benzene-1,3-diol | M + H | 428.1372 | 428.1386 |
| 4-chloro-6-[5-({4-[(4-methylpiperazin-1-yl)methyl]phenyl}carbonyl)-4,5,6,7-tetrahydroisoxazolo[4,3-c]pyridin-3-yl]benzene-1,3-diol | M + H | 483.1794 | 483.1801 |
| 4-chloro-6-(5-{[4-(morpholin-4-ylmethyl)phenyl]carbonyl}-4,5,6,7-tetrahydroisoxazolo[4,3-c]pyridin-3-yl)benzene-1,3-diol | M + H | 470.1477 | 470.1482 |
| 4-(5-{[4-(benzyloxy)phenyl]acetyl}-4,5,6,7-tetrahydroisoxazolo[4,3-c]pyridin-3-yl)-6-chlorobenzene-1,3-diol | M + H | 491.1369 | 491.1364 |
| 4-chloro-6-(5-{[4-(hydroxymethyl)cyclohexyl]carbonyl}-4,5,6,7-tetrahydroisoxazolo[4,3-c]pyridin-3-yl)benzene-1,3-diol | M + H | 407.1369 | 407.1385 |
| 4-(5-{[4-(aminomethyl)cyclohexyl]carbonyl}-4,5,6,7-tetrahydroisoxazolo[4,3-c]pyridin-3-yl)-6-chlorobenzene-1,3-diol hydrochloride | M + H | 406.1528 | 406.1545 |
| 4-(5-{[4-(benzylsulfonyl)phenyl]acetyl}-4,5,6,7-tetrahydroisoxazolo[4,3-c]pyridin-3-yl)-6-chlorobenzene-1,3-diol | M + H | 539.1038 | 539.104 |
| N-(3-{2-[3-(5-chloro-2,4-dihydroxyphenyl)-6,7-dihydroisoxazolo[4,3-c]pyridin-5(4H)-yl]-2-oxoethyl}phenyl)methanesulfonamide | M + H | 478.0834 | 478.0838 |
| 4-chloro-6-[5-({4-[(4-methylpiperazin-1-yl)methyl]phenyl}acetyl)-4,5,6,7-tetrahydroisoxazolo[4,3-c]pyridin-3-yl]benzene-1,3-diol | M + H | 497.195 | 497.1962 |
| 4-chloro-6-(5-{[4-(piperidin-1-ylmethyl)phenyl]acetyl}-4,5,6,7-tetrahydroisoxazolo[4,3-c]pyridin-3-yl)benzene-1,3-diol | M + H | 482.1841 | 482.1846 |

-continued

| Name | ION | HRMS (ESI): EMASS CALC | HRMS (ESI): EMASS FOUND |
|---|---|---|---|
| 4-chloro-6-[5-(3-morpholin-4-ylpropanoyl)-4,5,6,7-tetrahydroisoxazolo[4,3-c]pyridin-3-yl]benzene-1,3-diol | M + H | 408.1321 | 408.1317 |
| 4-chloro-6-(5-{[4-(morpholin-4-ylmethyl)phenyl]acetyl}-4,5,6,7-tetrahydroisoxazolo[4,3-c]pyridin-3-yl)benzene-1,3-diol | M + H | 484.1634 | 484.1638 |

Example 13

Preparation of 4-Chloro-6-(5-(piperidin-4-yl)-4,5,6,7-tetrahydro-isoxazolo[4,3-c]pyridin-3-yl]benzene-1,3-diol [(1), A=Cl, X=O, R=$C_5H_{10}N$, m=1 n=1]

Step k5

4-[3-(5-chloro-2,4-dihydroxyphenyl)-6,7-dihydro-4H-isoxazolo[4,3-c]pyridin-5(4H)-yl]piperidine-1-carboxylic acid tert-butyl ester [(1), A=Cl, X=O, R=$C_{10}H_{18}NO_2$, m=1 n=1]

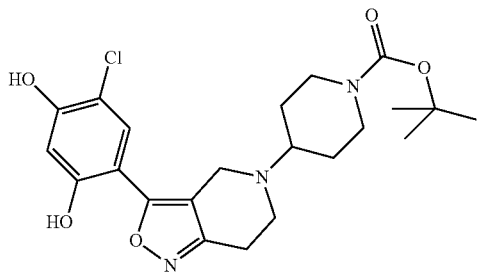

To a suspension of Boc-4-piperidone (0.020 g, 0.1 mmol) in N,N'-dimethylacetamide (DMA) (0.5 mL), tetramethylammonium triacetoxyborohydride (0.0052 g, 0.2 mmol) and 4-chloro-6-(4,5,6,7-tetrahydroisoxazolo[4,3-c]pyridin-3-yl)benzene-1,3-diol (0.027 g, 0.1 mmol), dissolved in DMA (0.5 mL) was added and the reaction was stirred for 16 h at room temperature. HPLC analysis after 16 h indicated the conversion of the starting material to product. The solvent was removed in vacuo.

Step c2

4-Chloro-6-(5-(piperidin-4-yl)-4,5,6,7-tetrahydro-isoxazolo[4,3-c]pyridin-3-yl]benzene-1,3-diol [(1), A=Cl, X=O, R=$C_{10}H_{18}NO_2$, m=1 n=1]

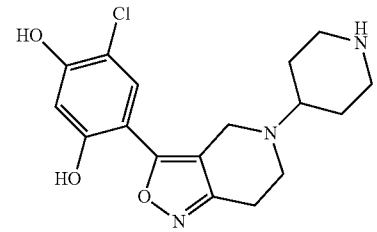

To 4-[3-(5-chloro-2,4-dihydroxyphenyl)-6,7-dihydro-4H-isoxazolo[4,3-c]pyridin-5(4H)-yl]piperidine-1-carboxylic acid tert-butyl ester prepared in Step k5, a solution of TFA/DCM (1:1) (0.5 mL) of was charged to the vial and stirred for 1 h at ambient temperature. The solvent was then removed in vacuo and the product was purified via semi-preparative HPLC according to the protocol indicated below.

In the case where the protection for the amine was an Fmoc group, a solution of 10% piperidine in DMF (0.5 mL) was added to the vial, which was then stirred for 1 h. The solvent was then removed in vacuo and the product was purified via semi-preparative HPLC according to the protocol indicated below.

In the case where a tert-butyldimethylsilyl (TBDMS) protecting group existed, a 2N NaOH solution (0.2 mL) was added to the reaction cocktail in Step 1, and stirred for 2 h at ambient. After the 2 h of the NaOH treatment, a 2N HCl solution (0.2 mL) was added to neutralize the solution. The solvent was then removed in vacuo and the product was purified via semi-preparative HPLC according to the protocol indicated below.

By working analogously and in parallel, the following compounds were prepared:

| Name | M + H | RT | METHOD |
|---|---|---|---|
| 4-chloro-6-[5-(2-hydroxyethyl)-4,5,6,7-tetrahydroisoxazolo[4,3-c]pyridin-3-yl]benzene-1,3-diol | 311.07 | 1.261 | 1 |
| 4-chloro-6-[5-(pyrrolidin-3-yl)-4,5,6,7-tetrahydroisoxazolo[4,3-c]pyridin-3-yl]benzene-1,3-diol | 336.1 | 0.681 | 1 |
| 4-[3-(5-chloro-2,4-dihydroxyphenyl)-6,7-dihydroisoxazolo[4,3-c]pyridin-5(4H)-yl]butan-2-one | 337.09 | 0.781 | 1 |
| 4-chloro-6-[5-(2-furylmethyl)-4,5,6,7-tetrahydroisoxazolo[4,3-c]pyridin-3-yl]benzene-1,3-diol | 347.07 | 0.861 | 1 |
| 4-chloro-6-[5-(1H-imidazol-2-ylmethyl)-4,5,6,7-tetrahydroisoxazolo[4,3-c]pyridin-3-yl]benzene-1,3-diol | 347.08 | 0.699 | 1 |
| 4-chloro-6-[5-(piperidin-3-yl)-4,5,6,7-tetrahydroisoxazolo[4,3-c]pyridin-3-yl]benzene-1,3-diol | 350.12 | 0.726 | 1 |
| 4-chloro-6-[5-(piperidin-4-yl)-4,5,6,7-tetrahydroisoxazolo[4,3-c]pyridin-3-yl]benzene-1,3-diol | 350.12 | 0.993 | 1 |

-continued

| Name | M + H | RT | METHOD |
|---|---|---|---|
| 4-chloro-6-{5-[1-(dimethylamino)propan-2-yl]-4,5,6,7-tetrahydroisoxazolo[4,3-c]pyridin-3-yl}benzene-1,3-diol | 352.13 | 0.812 | 1 |
| 4-chloro-6-[5-(5-hydroxypentyl)-4,5,6,7-tetrahydroisoxazolo[4,3-c]pyridin-3-yl]benzene-1,3-diol | 353.12 | 0.783 | 1 |
| 4-chloro-6-[5-(pyridin-2-ylmethyl)-4,5,6,7-tetrahydroisoxazolo[4,3-c]pyridin-3-yl]benzene-1,3-diol | 358.09 | 0.775 | 1 |
| 4-chloro-6-[5-(pyridin-4-ylmethyl)-4,5,6,7-tetrahydroisoxazolo[4,3-c]pyridin-3-yl]benzene-1,3-diol | 358.09 | 0.668 | 1 |
| 4-chloro-6-{5-[(1-methyl-1H-pyrrol-2-yl)methyl]-4,5,6,7-tetrahydroisoxazolo[4,3-c]pyridin-3-yl}benzene-1,3-diol | 360.1 | 0.902 | 1 |
| 4-chloro-6-{5-[(1-methyl-1H-imidazol-2-yl)methyl]-4,5,6,7-tetrahydroisoxazolo[4,3-c]pyridin-3-yl}benzene-1,3-diol | 361.1 | 0.772 | 1 |
| 4-chloro-6-[5-(2-thienylmethyl)-4,5,6,7-tetrahydroisoxazolo[4,3-c]pyridin-3-yl]benzene-1,3-diol | 363.05 | 0.901 | 1 |
| 4-chloro-6-[5-(3-thienylmethyl)-4,5,6,7-tetrahydroisoxazolo[4,3-c]pyridin-3-yl]benzene-1,3-diol | 363.05 | 0.85 | 1 |
| 4-chloro-6-[5-(cyclohexylmethyl)-4,5,6,7-tetrahydroisoxazolo[4,3-c]pyridin-3-yl]benzene-1,3-diol | 363.14 | 0.991 | 1 |
| 4-chloro-6-[5-(1-methylpiperidin-4-yl)-4,5,6,7-tetrahydroisoxazolo[4,3-c]pyridin-3-yl]benzene-1,3-diol | 364.13 | 0.618 | 1 |
| 4-chloro-6-[5-(4-hydroxycyclohexyl)-4,5,6,7-tetrahydro-1H-pyrazolo[4,3-c]pyridin-3-yl]benzene-1,3-diol | 364.13 | 0.625 | 1 |
| 4-chloro-6-[5-(4-hydroxycyclohexyl)-4,5,6,7-tetrahydroisoxazolo[4,3-c]pyridin-3-yl]benzene-1,3-diol | 365.12 | 0.781 | 1 |
| 4-chloro-6-[5-(tetrahydro-2H-thiopyran-4-yl)-4,5,6,7-tetrahydroisoxazolo[4,3-c]pyridin-3-yl]benzene-1,3-diol | 367.08 | 0.799 | 1 |
| 4-chloro-6-[5-(2-phenylethyl)-4,5,6,7-tetrahydroisoxazolo[4,3-c]pyridin-3-yl]benzene-1,3-diol | 371.11 | 0.96 | 1 |
| 4-chloro-6-{5-[(6-methylpyridin-2-yl)methyl]-4,5,6,7-tetrahydroisoxazolo[4,3-c]pyridin-3-yl}benzene-1,3-diol | 372.1 | 0.838 | 1 |
| 4-chloro-6-[5-(4-hydroxybenzyl)-4,5,6,7-tetrahydroisoxazolo[4,3-c]pyridin-3-yl]benzene-1,3-diol | 373.09 | 0.853 | 1 |
| 4-chloro-6-[5-(3-hydroxybenzyl)-4,5,6,7-tetrahydroisoxazolo[4,3-c]pyridin-3-yl]benzene-1,3-diol | 373.09 | 0.809 | 1 |
| 4-chloro-6-[5-(4-fluorobenzyl)-4,5,6,7-tetrahydroisoxazolo[4,3-c]pyridin-3-yl]benzene-1,3-diol | 375.08 | 0.951 | 1 |
| 4-chloro-6-[5-(3-fluorobenzyl)-4,5,6,7-tetrahydroisoxazolo[4,3-c]pyridin-3-yl]benzene-1,3-diol | 375.08 | 0.897 | 1 |
| 4-[5-(1-azabicyclo[2.2.2]oct-3-yl)-4,5,6,7-tetrahydroisoxazolo[4,3-c]pyridin-3-yl]-6-chlorobenzene-1,3-diol | 376.13 | 0.658 | 1 |
| 4-chloro-6-{5-[(5-methyl-2-thienyl)methyl]-4,5,6,7-tetrahydroisoxazolo[4,3-c]pyridin-3-yl}benzene-1,3-diol | 377.06 | 0.927 | 1 |
| 4-chloro-6-(5-{[5-(hydroxymethyl)-2-furyl]methyl}-4,5,6,7-tetrahydroisoxazolo[4,3-c]pyridin-3-yl)benzene-1,3-diol | 377.08 | 0.739 | 1 |
| 3-{[3-(5-chloro-2,4-dihydroxyphenyl)-6,7-dihydroisoxazolo[4,3-c]pyridin-5(4H)-yl]methyl}benzonitrile | 382.09 | 0.913 | 1 |
| 4-{[3-(5-chloro-2,4-dihydroxyphenyl)-6,7-dihydroisoxazolo[4,3-c]pyridin-5(4H)-yl]methyl}benzonitrile | 382.09 | 0.846 | 1 |
| 4-chloro-6-[5-(3-phenylpropyl)-4,5,6,7-tetrahydroisoxazolo[4,3-c]pyridin-3-yl]benzene-1,3-diol | 385.12 | 0.929 | 1 |
| 4-chloro-6-[5-(3,4-dimethylbenzyl)-4,5,6,7-tetrahydroisoxazolo[4,3-c]pyridin-3-yl]benzene-1,3-diol | 385.12 | 1.038 | 1 |
| 4-chloro-6-[5-(4-methoxybenzyl)-4,5,6,7-tetrahydroisoxazolo[4,3-c]pyridin-3-yl]benzene-1,3-diol | 387.1 | 0.961 | 1 |
| 4-chloro-6-[5-(2-hydroxy-2-phenylethyl)-4,5,6,7-tetrahydroisoxazolo[4,3-c]pyridin-3-yl]benzene-1,3-diol | 387.1 | 1.023 | 1 |
| 4-chloro-6-[5-(3-methoxybenzyl)-4,5,6,7-tetrahydroisoxazolo[4,3-c]pyridin-3-yl]benzene-1,3-diol | 387.1 | 0.919 | 1 |
| 4-{[3-(5-chloro-2,4-dihydroxyphenyl)-6,7-dihydroisoxazolo[4,3-c]pyridin-5(4H)-yl]methyl}benzene-1,2-diol | 389.08 | 0.823 | 1 |
| 4-chloro-6-[5-(3,5-dihydroxybenzyl)-4,5,6,7-tetrahydroisoxazolo[4,3-c]pyridin-3-yl]benzene-1,3-diol | 389.08 | 0.812 | 1 |
| 5-{[3-(5-chloro-2,4-dihydroxyphenyl)-6,7-dihydroisoxazolo[4,3-c]pyridin-5(4H)-yl]methyl}pyrimidine-2,4(1H,3H)-dione | 391.07 | 0.702 | 1 |
| 4-chloro-6-[5-(1-propylpiperidin-4-yl)-4,5,6,7-tetrahydroisoxazolo[4,3-c]pyridin-3-yl]benzene-1,3-diol | 392.13 | 0.697 | 1 |
| 4-chloro-6-[5-(1-propylpiperidin-4-yl)-4,5,6,7-tetrahydroisoxazolo[4,3-c]pyridin-3-yl]benzene-1,3-diol | 392.17 | 0.648 | 1 |
| 4-chloro-6-[5-(1-isopropylpiperidin-4-yl)-4,5,6,7-tetrahydroisoxazolo[4,3-c]pyridin-3-yl]benzene-1,3-diol | 392.17 | 0.649 | 1 |
| 4-chloro-6-[5-(3,4-difluorobenzyl)-4,5,6,7-tetrahydroisoxazolo[4,3-c]pyridin-3-yl]benzene-1,3-diol | 393.07 | 0.935 | 1 |

-continued

| Name | M + H | RT | METHOD |
|---|---|---|---|
| 4-chloro-6-[5-(3,5-difluorobenzyl)-4,5,6,7-tetrahydroisoxazolo[4,3-c]pyridin-3-yl]benzene-1,3-diol | 393.07 | 0.924 | 1 |
| 4-chloro-6-{5-[(5-chloro-2-thienyl)methyl]-4,5,6,7-tetrahydroisoxazolo[4,3-c]pyridin-3-yl}benzene-1,3-diol | 397.01 | 0.969 | 1 |
| 4-[5-(1,3-benzodioxol-5-ylmethyl)-4,5,6,7-tetrahydro-1H-pyrazolo[4,3-c]pyridin-3-yl]-6-chlorobenzene-1,3-diol | 400.1 | 0.863 | 1 |
| 4-chloro-6-[5-(4-ethoxybenzyl)-4,5,6,7-tetrahydro-1H-pyrazolo[4,3-c]pyridin-3-yl]benzene-1,3-diol | 400.13 | 0.973 | 1 |
| 4-{[3-(5-chloro-2,4-dihydroxyphenyl)-6,7-dihydroisoxazolo[4,3-c]pyridin-5(4H)-yl]methyl}benzoic acid | 401.08 | 0.842 | 1 |
| 4-[5-(1,3-benzodioxol-5-ylmethyl)-4,5,6,7-tetrahydroisoxazolo[4,3-c]pyridin-3-yl]-6-chlorobenzene-1,3-diol | 401.08 | 0.889 | 1 |
| 5-[3-(5-chloro-2,4-dihydroxyphenyl)-6,7-dihydroisoxazolo[4,3-c]pyridin-5(4H)-yl]-5-deoxy-D-xylitol | 401.1 | 0.721 | 1 |
| 1-[3-(5-chloro-2,4-dihydroxyphenyl)-6,7-dihydroisoxazolo[4,3-c]pyridin-5(4H)-yl]-1-deoxy-D-xylitol | 401.1 | 0.673 | 1 |
| 4-chloro-6-[5-(4-ethoxybenzyl)-4,5,6,7-tetrahydroisoxazolo[4,3-c]pyridin-3-yl]benzene-1,3-diol | 401.12 | 0.998 | 1 |
| 4-chloro-6-[5-(4-nitrobenzyl)-4,5,6,7-tetrahydroisoxazolo[4,3-c]pyridin-3-yl]benzene-1,3-diol | 402.08 | 0.911 | 1 |
| 4-chloro-6-[5-(3-nitrobenzyl)-4,5,6,7-tetrahydroisoxazolo[4,3-c]pyridin-3-yl]benzene-1,3-diol | 402.08 | 0.887 | 1 |
| 4-chloro-6-[5-(3-hydroxy-4-methoxybenzyl)-4,5,6,7-tetrahydro-1H-pyrazolo[4,3-c]pyridin-3-yl]benzene-1,3-diol | 402.11 | 0.759 | 1 |
| 4-chloro-6-[5-(4-hydroxy-3-methoxybenzyl)-4,5,6,7-tetrahydroisoxazolo[4,3-c]pyridin-3-yl]benzene-1,3-diol | 403.1 | 0.814 | 1 |
| 4-chloro-6-[5-(3-hydroxy-4-methoxybenzyl)-4,5,6,7-tetrahydroisoxazolo[4,3-c]pyridin-3-yl]benzene-1,3-diol | 403.1 | 0.828 | 1 |
| 4-[5-(1-butylpiperidin-4-yl)-4,5,6,7-tetrahydroisoxazolo[4,3-c]pyridin-3-yl]-6-chlorobenzene-1,3-diol | 406.18 | 0.689 | 1 |
| 4-chloro-6-[5-(1,4-dioxaspiro[4.5]dec-8-yl)-4,5,6,7-tetrahydroisoxazolo[4,3-c]pyridin-3-yl]benzene-1,3-diol | 407.13 | 0.799 | 1 |
| 4-chloro-6-{5-[(5-nitro-2-thienyl)methyl]-4,5,6,7-tetrahydroisoxazolo[4,3-c]pyridin-3-yl}benzene-1,3-diol | 408.03 | 0.938 | 1 |
| 4-chloro-6-[5-(3-chloro-4-fluorobenzyl)-4,5,6,7-tetrahydroisoxazolo[4,3-c]pyridin-3-yl]benzene-1,3-diol | 409.04 | 0.994 | 1 |
| 4-[5-(4-tert-butylbenzyl)-4,5,6,7-tetrahydroisoxazolo[4,3-c]pyridin-3-yl]-6-chlorobenzene-1,3-diol | 413.16 | 1.193 | 1 |
| 4-chloro-6-{5-[(5-fluoro-1H-indol-3-yl)methyl]-4,5,6,7-tetrahydroisoxazolo[4,3-c]pyridin-3-yl}benzene-1,3-diol | 414.09 | 0.968 | 1 |
| N-(4-{[3-(5-chloro-2,4-dihydroxyphenyl)-6,7-dihydroisoxazolo[4,3-c]pyridin-5(4H)-yl]methyl}phenyl)acetamide | 414.11 | 0.789 | 1 |
| 4-chloro-6-[5-(2,3-dihydro-1,4-benzodioxin-6-ylmethyl)-4,5,6,7-tetrahydro-1H-pyrazolo[4,3-c]pyridin-3-yl]benzene-1,3-diol | 414.11 | 0.882 | 1 |
| 4-chloro-6-[5-(4-propoxybenzyl)-4,5,6,7-tetrahydro-1H-pyrazolo[4,3-c]pyridin-3-yl]benzene-1,3-diol | 414.15 | 1.091 | 1 |
| methyl 3-{[3-(5-chloro-2,4-dihydroxyphenyl)-6,7-dihydroisoxazolo[4,3-c]pyridin-5(4H)-yl]methyl}benzoate | 415.1 | 0.963 | 1 |
| 4-chloro-6-[5-(2,3-dihydro-1,4-benzodioxin-6-ylmethyl)-4,5,6,7-tetrahydroisoxazolo[4,3-c]pyridin-3-yl]benzene-1,3-diol | 415.1 | 0.98 | 1 |
| 4-chloro-6-[5-(4-isopropoxybenzyl)-4,5,6,7-tetrahydroisoxazolo[4,3-c]pyridin-3-yl]benzene-1,3-diol | 415.13 | 1.069 | 1 |
| 4-chloro-6-[5-(4-methoxy-2,3-dimethylbenzyl)-4,5,6,7-tetrahydroisoxazolo[4,3-c]pyridin-3-yl]benzene-1,3-diol | 415.13 | 1.047 | 1 |
| 4-chloro-6-[5-(4-propoxybenzyl)-4,5,6,7-tetrahydroisoxazolo[4,3-c]pyridin-3-yl]benzene-1,3-diol | 415.13 | 1.15 | 1 |
| 4-chloro-6-[5-(3,4-dimethoxybenzyl)-4,5,6,7-tetrahydro-1H-pyrazolo[4,3-c]pyridin-3-yl]benzene-1,3-diol | 416.13 | 0.836 | 1 |
| 4-chloro-6-{5-[4-(trifluoromethyl)cyclohexyl]-4,5,6,7-tetrahydroisoxazolo[4,3-c]pyridin-3-yl}benzene-1,3-diol | 417.11 | 1.008 | 1 |
| 4-chloro-6-[5-(3,4-dimethoxybenzyl)-4,5,6,7-tetrahydroisoxazolo[4,3-c]pyridin-3-yl]benzene-1,3-diol | 417.11 | 0.879 | 1 |
| 4-chloro-6-[5-(3,5-dimethoxybenzyl)-4,5,6,7-tetrahydroisoxazolo[4,3-c]pyridin-3-yl]benzene-1,3-diol | 417.11 | 0.956 | 1 |
| 4-chloro-6-[5-(2-hydroxy-5-nitrobenzyl)-4,5,6,7-tetrahydroisoxazolo[4,3-c]pyridin-3-yl]benzene-1,3-diol | 418.07 | 0.898 | 1 |
| 4-chloro-6-{5-[4-(1H-pyrrol-1-yl)benzyl]-4,5,6,7-tetrahydro-1H-pyrazolo[4,3-c]pyridin-3-yl}benzene-1,3-diol | 421.14 | 1.067 | 1 |

-continued

| Name | M + H | RT | METHOD |
|---|---|---|---|
| 4-chloro-6-{5-[3-(1H-pyrrol-1-yl)benzyl]-4,5,6,7-tetrahydro-1H-pyrazolo[4,3-c]pyridin-3-yl}benzene-1,3-diol | 421.14 | 1.057 | 1 |
| 4-chloro-6-{5-[4-(1H-pyrrol-1-yl)benzyl]-4,5,6,7-tetrahydroisoxazolo[4,3-c]pyridin-3-yl}benzene-1,3-diol | 422.12 | 1.134 | 1 |
| 4-chloro-6-{5-[3-(1H-pyrrol-1-yl)benzyl]-4,5,6,7-tetrahydroisoxazolo[4,3-c]pyridin-3-yl}benzene-1,3-diol | 422.12 | 1.132 | 1 |
| 4-chloro-6-{5-[3-(1H-pyrazol-1-yl)benzyl]-4,5,6,7-tetrahydro-1H-pyrazolo[4,3-c]pyridin-3-yl}benzene-1,3-diol | 422.13 | 0.894 | 1 |
| 4-chloro-6-{5-[4-(1H-imidazol-1-yl)benzyl]-4,5,6,7-tetrahydro-1H-pyrazolo[4,3-c]pyridin-3-yl}benzene-1,3-diol | 422.13 | 0.56 | 1 |
| 4-chloro-6-{5-[4-(1H-pyrazol-1-yl)benzyl]-4,5,6,7-tetrahydro-1H-pyrazolo[4,3-c]pyridin-3-yl}benzene-1,3-diol | 422.13 | 0.876 | 1 |
| 4-chloro-6-{5-[3-(1H-imidazol-1-yl)benzyl]-4,5,6,7-tetrahydro-1H-pyrazolo[4,3-c]pyridin-3-yl}benzene-1,3-diol | 422.13 | 0.564 | 1 |
| ethyl 4-[3-(5-chloro-2,4-dihydroxyphenyl)-6,7-dihydroisoxazolo[4,3-c]pyridin-5(4H)-yl]piperidine-1-carboxylate | 422.14 | 0.856 | 1 |
| 4-chloro-6-{5-[3-(1H-imidazol-1-yl)benzyl]-4,5,6,7-tetrahydroisoxazolo[4,3-c]pyridin-3-yl}benzene-1,3-diol | 423.11 | 0.712 | 1 |
| 4-chloro-6-{5-[3-(1H-pyrazol-1-yl)benzyl]-4,5,6,7-tetrahydroisoxazolo[4,3-c]pyridin-3-yl}benzene-1,3-diol | 423.11 | 0.994 | 1 |
| 4-chloro-6-{5-[4-(1H-imidazol-1-yl)benzyl]-4,5,6,7-tetrahydroisoxazolo[4,3-c]pyridin-3-yl}benzene-1,3-diol | 423.11 | 0.72 | 1 |
| 4-chloro-6-{5-[4-(1H-pyrazol-1-yl)benzyl]-4,5,6,7-tetrahydroisoxazolo[4,3-c]pyridin-3-yl}benzene-1,3-diol | 423.11 | 0.986 | 1 |
| 4-chloro-6-{5-[3-(1H-1,2,4-triazol-1-yl)benzyl]-4,5,6,7-tetrahydro-1H-pyrazolo[4,3-c]pyridin-3-yl}benzene-1,3-diol | 423.13 | 0.731 | 1 |
| 4-chloro-6-{5-[4-(1H-1,2,4-triazol-1-yl)benzyl]-4,5,6,7-tetrahydro-1H-pyrazolo[4,3-c]pyridin-3-yl}benzene-1,3-diol | 423.13 | 0.725 | 1 |
| 4-chloro-6-{5-[4-(2H-1,2,3-triazol-2-yl)benzyl]-4,5,6,7-tetrahydro-1H-pyrazolo[4,3-c]pyridin-3-yl}benzene-1,3-diol | 423.13 | 0.895 | 1 |
| 4-chloro-6-{5-[4-(1H-1,2,3-triazol-1-yl)benzyl]-4,5,6,7-tetrahydro-1H-pyrazolo[4,3-c]pyridin-3-yl}benzene-1,3-diol | 423.13 | 0.752 | 1 |
| 4-chloro-6-{5-[3-(1H-1,2,4-triazol-1-yl)benzyl]-4,5,6,7-tetrahydroisoxazolo[4,3-c]pyridin-3-yl}benzene-1,3-diol | 424.11 | 0.862 | 1 |
| 4-chloro-6-{5-[4-(1H-1,2,4-triazol-1-yl)benzyl]-4,5,6,7-tetrahydroisoxazolo[4,3-c]pyridin-3-yl}benzene-1,3-diol | 424.11 | 0.861 | 1 |
| 4-chloro-6-{5-[4-(2H-1,2,3-triazol-2-yl)benzyl]-4,5,6,7-tetrahydroisoxazolo[4,3-c]pyridin-3-yl}benzene-1,3-diol | 424.11 | 0.997 | 1 |
| 4-chloro-6-{5-[4-(1H-1,2,3-triazol-1-yl)benzyl]-4,5,6,7-tetrahydroisoxazolo[4,3-c]pyridin-3-yl}benzene-1,3-diol | 424.11 | 0.886 | 1 |
| 4-{5-[(5-bromo-2-furyl)methyl]-4,5,6,7-tetrahydroisoxazolo[4,3-c]pyridin-3-yl}-6-chlorobenzene-1,3-diol | 424.98 | 0.917 | 1 |
| 4-chloro-6-{5-[3-(trifluoromethyl)benzyl]-4,5,6,7-tetrahydroisoxazolo[4,3-c]pyridin-3-yl}benzene-1,3-diol | 425.08 | 1.033 | 1 |
| 4-chloro-6-[5-(4-phenylcyclohexyl)-4,5,6,7-tetrahydroisoxazolo[4,3-c]pyridin-3-yl]benzene-1,3-diol | 425.16 | 1.144 | 1 |
| 4-chloro-6-{5-[3-(pyrrolidin-1-yl)benzyl]-4,5,6,7-tetrahydro-1H-pyrazolo[4,3-c]pyridin-3-yl}benzene-1,3-diol | 425.17 | 1.043 | 1 |
| 4-[5-(1-benzylpyrrolidin-3-yl)-4,5,6,7-tetrahydroisoxazolo[4,3-c]pyridin-3-yl]-6-chlorobenzene-1,3-diol | 426.15 | 0.792 | 1 |
| 4-chloro-6-{5-[3-(pyrrolidin-1-yl)benzyl]-4,5,6,7-tetrahydroisoxazolo[4,3-c]pyridin-3-yl}benzene-1,3-diol | 426.15 | 1.12 | 1 |
| 4-chloro-6-{5-[4-(diethylamino)benzyl]-4,5,6,7-tetrahydroisoxazolo[4,3-c]pyridin-3-yl}benzene-1,3-diol | 428.17 | 0.736 | 1 |
| 4-[5-(4-butoxybenzyl)-4,5,6,7-tetrahydroisoxazolo[4,3-c]pyridin-3-yl]-6-chlorobenzene-1,3-diol | 429.15 | 1.207 | 1 |
| 4-chloro-6-(5-{4-[(2-hydroxyethyl)(methyl)amino]benzyl}-4,5,6,7-tetrahydro-1H-pyrazolo[4,3-c]pyridin-3-yl)benzene-1,3-diol | 429.16 | 0.71 | 1 |
| 4-chloro-6-[5-(3-ethoxy-4-methoxybenzyl)-4,5,6,7-tetrahydroisoxazolo[4,3-c]pyridin-3-yl]benzene-1,3-diol | 430.15 | 0.908 | 1 |
| 4-chloro-6-[5-(3-ethoxy-4-methoxybenzyl)-4,5,6,7-tetrahydro-1H-pyrazolo[4,3-c]pyridin-3-yl]benzene-1,3-diol | 430.15 | 0.908 | 1 |

-continued

| Name | M + H | RT | METHOD |
|---|---|---|---|
| 4-chloro-6-(5-{4-[(2-hydroxyethyl)(methyl)amino]benzyl}-4,5,6,7-tetrahydroisoxazolo[4,3-c]pyridin-3-yl)benzene-1,3-diol | 430.15 | 0.86 | 1 |
| 4-chloro-6-[5-(3-ethoxy-4-methoxybenzyl)-4,5,6,7-tetrahydroisoxazolo[4,3-c]pyridin-3-yl]benzene-1,3-diol | 431.13 | 1.007 | 1 |
| 4-[5-(biphenyl-4-ylmethyl)-4,5,6,7-tetrahydroisoxazolo[4,3-c]pyridin-3-yl]-6-chlorobenzene-1,3-diol | 433.12 | 1.156 | 1 |
| 4-chloro-6-{5-[4-(methylsulfonyl)benzyl]-4,5,6,7-tetrahydroisoxazolo[4,3-c]pyridin-3-yl}benzene-1,3-diol | 435.07 | 0.792 | 1 |
| 4-{5-[(6-bromopyridin-2-yl)methyl]-4,5,6,7-tetrahydroisoxazolo[4,3-c]pyridin-3-yl}-6-chlorobenzene-1,3-diol | 436 | 0.906 | 1 |
| 4-chloro-6-[5-(2-chloro-5-nitrobenzyl)-4,5,6,7-tetrahydroisoxazolo[4,3-c]pyridin-3-yl]benzene-1,3-diol | 436.04 | 0.966 | 1 |
| 4-chloro-6-{5-[(4-phenyl-2-thienyl)methyl]-4,5,6,7-tetrahydroisoxazolo[4,3-c]pyridin-3-yl}benzene-1,3-diol | 439.08 | 1.127 | 1 |
| 1-(4-{[3-(5-chloro-2,4-dihydroxyphenyl)-1,4,6,7-tetrahydro-5H-pyrazolo[4,3-c]pyridin-5-yl]methyl}phenyl)pyrrolidin-2-one | 439.15 | 0.819 | 1 |
| 4-chloro-6-{5-[3-(piperidin-1-yl)benzyl]-4,5,6,7-tetrahydro-1H-pyrazolo[4,3-c]pyridin-3-yl}benzene-1,3-diol | 439.18 | 0.69 | 1 |
| 4-chloro-6-{5-[4-(piperidin-1-yl)benzyl]-4,5,6,7-tetrahydro-1H-pyrazolo[4,3-c]pyridin-3-yl}benzene-1,3-diol | 439.18 | 0.6 | 1 |
| 1-(4-{[3-(5-chloro-2,4-dihydroxyphenyl)-6,7-dihydroisoxazolo[4,3-c]pyridin-5(4H)-yl]methyl}phenyl)pyrrolidin-2-one | 440.13 | 0.932 | 1 |
| 4-chloro-6-{5-[4-(piperidin-1-yl)benzyl]-4,5,6,7-tetrahydroisoxazolo[4,3-c]pyridin-3-yl}benzene-1,3-diol | 440.17 | 0.803 | 1 |
| 4-[5-(1-benzylpiperidin-4-yl)-4,5,6,7-tetrahydroisoxazolo[4,3-c]pyridin-3-yl]-6-chlorobenzene-1,3-diol | 440.17 | 0.734 | 1 |
| 4-chloro-6-{5-[3-(piperidin-1-yl)benzyl]-4,5,6,7-tetrahydroisoxazolo[4,3-c]pyridin-3-yl}benzene-1,3-diol | 440.17 | 0.797 | 1 |
| 4-chloro-6-{5-[4-(piperazin-1-yl)benzyl]-4,5,6,7-tetrahydro-1H-pyrazolo[4,3-c]pyridin-3-yl}benzene-1,3-diol | 440.18 | 1.177 | 1 |
| 4-chloro-6-{5-[4-(trifluoromethoxy)benzyl]-4,5,6,7-tetrahydroisoxazolo[4,3-c]pyridin-3-yl}benzene-1,3-diol | 441.08 | 1.096 | 1 |
| 4-chloro-6-{5-[4-(morpholin-4-yl)benzyl]-4,5,6,7-tetrahydro-1H-pyrazolo[4,3-c]pyridin-3-yl}benzene-1,3-diol | 441.16 | 0.89 | 1 |
| 4-chloro-6-{5-[3-(morpholin-4-yl)benzyl]-4,5,6,7-tetrahydro-1H-pyrazolo[4,3-c]pyridin-3-yl}benzene-1,3-diol | 441.16 | 0.892 | 1 |
| 4-chloro-6-{5-[4-(piperazin-1-yl)benzyl]-4,5,6,7-tetrahydroisoxazolo[4,3-c]pyridin-3-yl}benzene-1,3-diol | 441.16 | 1.28 | 1 |
| 4-chloro-6-{5-[4-(morpholin-4-yl)benzyl]-4,5,6,7-tetrahydroisoxazolo[4,3-c]pyridin-3-yl}benzene-1,3-diol | 442.15 | 0.99 | 1 |
| 4-chloro-6-{5-[3-(morpholin-4-yl)benzyl]-4,5,6,7-tetrahydroisoxazolo[4,3-c]pyridin-3-yl}benzene-1,3-diol | 442.15 | 0.99 | 1 |
| 4-chloro-6-(5-{[2-(morpholin-4-yl)pyridin-4-yl]methyl}-4,5,6,7-tetrahydro-1H-pyrazolo[4,3-c]pyridin-3-yl)benzene-1,3-diol | 442.16 | 0.574 | 1 |
| 4-chloro-6-(5-{[6-(morpholin-4-yl)pyridin-2-yl]methyl}-4,5,6,7-tetrahydro-1H-pyrazolo[4,3-c]pyridin-3-yl)benzene-1,3-diol | 442.16 | 0.865 | 1 |
| 4-chloro-6-(5-{[2-(morpholin-4-yl)pyridin-4-yl]methyl}-4,5,6,7-tetrahydroisoxazolo[4,3-c]pyridin-3-yl)benzene-1,3-diol | 443.14 | 0.753 | 1 |
| 4-chloro-6-(5-{[6-(morpholin-4-yl)pyridin-2-yl]methyl}-4,5,6,7-tetrahydroisoxazolo[4,3-c]pyridin-3-yl)benzene-1,3-diol | 443.14 | 0.989 | 1 |
| 4-chloro-6-(5-{4-[2-(dimethylamino)ethoxy]benzyl}-4,5,6,7-tetrahydroisoxazolo[4,3-c]pyridin-3-yl)benzene-1,3-diol | 444.16 | 0.691 | 1 |
| 4-chloro-6-[5-(3,4,5-trimethoxybenzyl)-4,5,6,7-tetrahydroisoxazolo[4,3-c]pyridin-3-yl]benzene-1,3-diol | 447.12 | 0.917 | 1 |
| 4-chloro-6-(5-{[2-(morpholin-4-yl)-1,3-thiazol-5-yl]methyl}-4,5,6,7-tetrahydroisoxazolo[4,3-c]pyridin-3-yl)benzene-1,3-diol | 449.1 | 0.791 | 1 |
| 4-chloro-6-[5-(3-phenoxybenzyl)-4,5,6,7-tetrahydroisoxazolo[4,3-c]pyridin-3-yl]benzene-1,3-diol | 449.12 | 1.164 | 1 |
| 4-chloro-6-{5-[4-(4-methylpiperazin-1-yl)benzyl]-4,5,6,7-tetrahydro-1H-pyrazolo[4,3-c]pyridin-3-yl}benzene-1,3-diol | 454.19 | 0.65 | 1 |

| Name | M + H | RT | METHOD |
|---|---|---|---|
| 4-chloro-6-{5-[4-(4-methylpiperazin-1-yl)benzyl]-4,5,6,7-tetrahydroisoxazolo[4,3-c]pyridin-3-yl}benzene-1,3-diol | 455.18 | 0.79 | 1 |
| 4-(5-{4-[bis(2-hydroxyethyl)amino]benzyl}-4,5,6,7-tetrahydro-1H-pyrazolo[4,3-c]pyridin-3-yl)-6-chlorobenzene-1,3-diol | 459.17 | 0.7 | 1 |
| 4-(5-{4-[bis(2-hydroxyethyl)amino]benzyl}-4,5,6,7-tetrahydroisoxazolo[4,3-c]pyridin-3-yl)-6-chlorobenzene-1,3-diol | 460.16 | 0.85 | 1 |
| 4-chloro-6-{5-[4-(4-methyl-1,4-diazepan-1-yl)benzyl]-4,5,6,7-tetrahydro-1H-pyrazolo[4,3-c]pyridin-3-yl}benzene-1,3-diol | 468.21 | 0.7 | 1 |
| 4-chloro-6-{5-[4-(4-methyl-1,4-diazepan-1-yl)benzyl]-4,5,6,7-tetrahydroisoxazolo[4,3-c]pyridin-3-yl}benzene-1,3-diol | 469.19 | 0.793 | 1 |
| 4-chloro-6-{5-[4-(1,1-dioxidothiomorpholin-4-yl)benzyl]-4,5,6,7-tetrahydro-1H-pyrazolo[4,3-c]pyridin-3-yl}benzene-1,3-diol | 489.13 | 0.805 | 1 |
| 4-chloro-6-{5-[1-(phenylsulfonyl)piperidin-4-yl]-4,5,6,7-tetrahydroisoxazolo[4,3-c]pyridin-3-yl}benzene-1,3-diol | 490.11 | 1.075 | 1 |
| 4-chloro-6-{5-[4-(1,1-dioxidothiomorpholin-4-yl)benzyl]-4,5,6,7-tetrahydroisoxazolo[4,3-c]pyridin-3-yl}benzene-1,3-diol | 490.11 | 0.927 | 1 |

| Name | ION | HRMS (ESI): Exact Mass Calc | HRMS (ESI): Exact Mass Found |
|---|---|---|---|
| 4-chloro-6-{5-[4-(dimethylamino)benzyl]-4,5,6,7-tetrahydroisoxazolo[4,3-c]pyridin-3-yl}benzene-1,3-diol | M + H | 400.1423 | 400.1408 |
| 4-(5-benzyl-4,5,6,7-tetrahydroisoxazolo[4,3-c]pyridin-3-yl)-6-chlorobenzene-1,3-diol hydrochloride | M + H | 357.1001 | 357.0991 |
| 4-chloro-6-[5-(pyridin-3-ylmethyl)-4,5,6,7-tetrahydroisoxazolo[4,3-c]pyridin-3-yl]benzene-1,3-diol | M + H | 358.0953 | 358.095 |
| 4-chloro-6-(5-cyclohexyl-4,5,6,7-tetrahydroisoxazolo[4,3-c]pyridin-3-yl)benzene-1,3-diol | M + H | 349.1314 | 349.1297 |
| 4-chloro-6-{5-[(6-morpholin-4-ylpyridin-3-yl)methyl]-4,5,6,7-tetrahydroisoxazolo[4,3-c]pyridin-3-yl}benzene-1,3-diol | M + H | 443.1481 | 443.1466 |
| 4-chloro-6-[5-(1-methylpiperidin-4-yl)-4,5,6,7-tetrahydroisoxazolo[4,3-c]pyridin-3-yl]benzene-1,3-diol | M + H | 364.1423 | 364.143 |
| 4-(5-benzyl-4,5,6,7-tetrahydroisoxazolo[4,3-c]pyridin-3-yl)-6-chlorobenzene-1,3-diol | M + H | 357.1001 | 357.0992 |
| 4-chloro-6-[5-(1-methylpiperidin-4-yl)-4,5,6,7-tetrahydroisoxazolo[4,3-c]pyridin-3-yl]benzene-1,3-diol dihydrochloride | M + H | 364.1423 | 364.1423 |
| 4-chloro-6-[5-(3-morpholin-4-ylpropyl)-4,5,6,7-tetrahydroisoxazolo[4,3-c]pyridin-3-yl]benzene-1,3-diol | M + H | 394.1528 | 394.1533 |
| 3-[3-(5-chloro-2,4-dihydroxyphenyl)-6,7-dihydroisoxazolo[4,3-c]pyridin-5(4H)-yl]propanoic acid | M + H | 339.0743 | 339.0759 |
| 4-chloro-6-[5-(3-morpholin-4-yl-3-oxopropyl)-4,5,6,7-tetrahydroisoxazolo[4,3-c]pyridin-3-yl]benzene-1,3-diol | M + H | 408.1321 | 408.133 |
| 4-(5-benzyl-4,5,6,7-tetrahydro-1H-pyrazolo[4,3-c]pyridin-3-yl)-6-chlorobenzene-1,3-diol | M + H | 356.116 | 356.1161 |
| 4-chloro-6-(5-{4-[2-(dimethylamino)ethoxy]benzyl}-4,5,6,7-tetrahydro-1H-pyrazolo[4,3-c]pyridin-3-yl)benzene-1,3-diol | M + H | 443.1845 | 443.1848 |
| N-(4-{[3-(5-chloro-2,4-dihydroxyphenyl)-1,4,6,7-tetrahydro-5H-pyrazolo[4,3-c]pyridin-5-yl]methyl}phenyl)acetamide trifluoroacetate | M + H | 413.1375 | 413.1381 |
| 4-chloro-6-{5-[4-(dimethylamino)benzyl]-4,5,6,7-tetrahydro-1H-pyrazolo[4,3-c]pyridin-3-yl}benzene-1,3-diol trifluoroacetate | M + H | 399.1583 | 399.1596 |
| 4-chloro-6-[5-(4-hydroxybenzyl)-4,5,6,7-tetrahydro-1H-pyrazolo[4,3-c]pyridin-3-yl]benzene-1,3-diol | M + H | 372.111 | 372.1114 |

| Name | ION | HRMS (ESI): Exact Mass Calc | HRMS (ESI): Exact Mass Found |
|---|---|---|---|
| 4-chloro-6-{5-[(6-morpholin-4-ylpyridin-3-yl)methyl]-4,5,6,7-tetrahydro-1H-pyrazolo[4,3-c]pyridin-3-yl}benzene-1,3-diol | M + H | 442.1641 | 442.1635 |
| 4-chloro-6-[5-(cyclohexylmethyl)-4,5,6,7-tetrahydro-1H-pyrazolo[4,3-c]pyridin-3-yl]benzene-1,3-diol | M + H | 362.163 | 362.1627 |
| 4-chloro-6-{5-[4-(dimethylamino)benzyl]-1,4,5,6-tetrahydropyrrolo[3,4-c]pyrazol-3-yl}benzene-1,3-diol | M + H | 385.1426 | 385.1444 |

Example 14

Conversion 5

Preparation of [3-(5-Chloro-2,4-dihydroxy-phenyl)-2,4,6,7-tetrahydro-pyrazolo[4,3-c]pyridin-5-yl]-(1,4-dioxa-spiro[4.5]dec-8-yl)-methanone [(1), A=Cl, X=N, R=C$_9$H$_{13}$O$_3$, m=1 n=1]

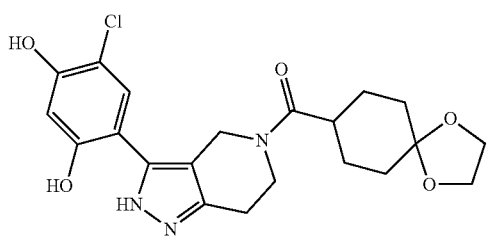

To a suspension of 4-{[3-(5-chloro-2,4-dihydroxyphenyl)-1,4,6,7-tetrahydro-5H-pyrazolo[4,3-c]pyridin-5-yl]carbonyl}cyclohexanone (0.094 g, 0.24 mmol) in toluene (2 mL), p-toluenesulphonic acid (0.004 mg, 0.0002 mol) and ethylene glycol (0.5 mL) were added. The mixture was stirred under reflux for 4 h. The solvent was removed in vacuo and suspended in water. The solid was filtered and purified by flash chromatography on silica gel eluting with DCM/MeOH 95/5 to afford the title compound 0.063 g in 60% yield.

$^1$H NMR (400 MHz, DMSO-d$_6$) δ ppm 1.65 (m, 8H) 2.79 (m, 1H) 2.72 (m, 2H) 3.75 (m, 2H) 3.79 (dd, 2H) 4.55 (dd, 2H) 6.18 (s, 1H) 6.40 (s, 1H) 10.42 (bs, 1H) 12.45 (bs, 1H)

HRMS (ESI): m/z calcd for C$_{21}$H$_{25}$ClN$_3$O$_5$$^+$ 434.1477 [M+H]$^+$. found 434.1472.

Example 15

Conversion 5

Preparation of [3-(5-Chloro-2,4-dihydroxy-phenyl)-2,4,6,7-tetrahydro-pyrazolo[4,3-c]-pyridin-5-yl]-(1,5-dioxa-spiro[5.5]undec-9-yl)-methanone [(1), A=Cl, X=N, R=C$_{11}$H$_{20}$O$_3$, m=1 n=1]

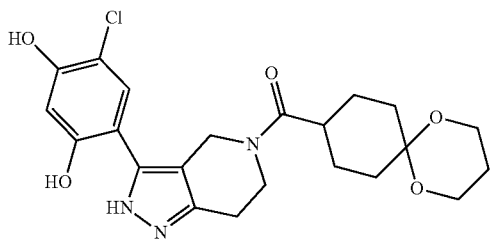

Operating as in Example 14, but employing 1,3-propandiol instead of 1,2-ethandiol, the title compound was obtained in 74% yield.

HRMS (ESI): m/z calcd for C$_{22}$H$_{27}$ClN$_3$O$_5$$^+$ 448.1634 [M+H]$^+$, found 448.1637.

Example 16

Step k8

Preparation of 4-[3-(5-Chloro-2,4-dihydroxy-phenyl)-1,4,6,7-tetrahydro-pyrazolo[4,3-c]pyridin-5-yl]butan-2-one [(1), A=Cl, X=N, R=C$_4$H$_7$O, m=1 n=1]

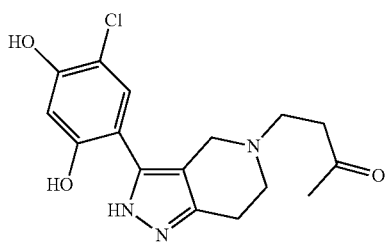

To a suspension of 4-chloro-6-(4,5,6,7-tetrahydro-1H-pyrazolo[4,3-c]pyridin-3-yl)-benzene-1,3-diol hydrochloride (0.1 g, 0.33 mmol) in DCM (5 mL) and DIPEA (0.114 mL, 0.66 mmol), methylvinyl ketone (0.030 mL, 0.36 mmol) was added. The mixture was stirred at room temperature for 30 min., then diluted with DCM and washed with brine. The organic phase was separated, dried over $Na_2SO_4$ and evaporated to dryness. The residue was purified by flash chromatography on silica gel eluting with DCM/MeOH 95/5 to afford 0.057 g of the title compound in 52% yield.

$^1$H NMR (400 MHz, DMSO-$d_6$) δ ppm 2.13 (s, 3H) 2.53-2.77 (m, 8H) 3.60 (bs, 2H) 6.18 (s, 1H) 6.54 (s, 1H) 7.15 (s, 1H) 10.23 (s, 1H) 11.42 (s, 1H) 12.81 (bs, 1H)

HRMS (ESI): m/z calcd for $C_{16}H_{16}ClN_3O_3^+$ 333.111 [M+H]$^+$, found 333.1095.

Example 17

Step k7

Preparation of 4-Chloro-6-[5-(3-morpholin-4-ylpropyl)-4,5,6,7-tetrahydro-1H-pyrazolo[4,3-c]pyridin-3-yl]-benzene-1,3-diol [(1), A=Cl, X=N, R=$C_7H_{1n}$NO, m=1 n=1]

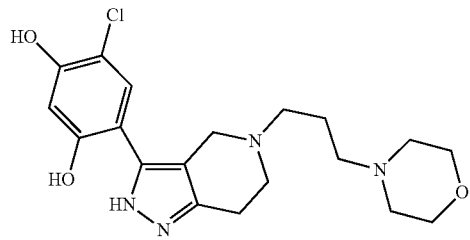

4-(3-Chloro-propyl)-morpholine hydrochloride (0.065 g, 0.4 mmol)) was added to a solution of 4-chloro-6-(4,5,6,7-tetrahydro-1H-pyrazolo[4,3-c]pyridin-3-yl)benzene-1,3-diol hydrochloride (0.100 g, 0.33 mmol) in DMF (2 mL) and DIPEA (0.172 mL, 0.99 mmol). The mixture was agitated at 80° C. for 8 h. The mixture was evaporated to dryness and purified by flash chromatography on silica gel (eluant: DCM/MeOH 95/5) to afford 64 mg of the title compound in 50% yield.

HRMS (ESI): m/z calcd for $C_{19}H_{26}ClN_4O_3^+$ 393.1687 [M+H]$^+$, found 393.1704.

Example 18

Step k7

Preparation of 4-Chloro-6-[5-(2-morpholin-4-yl-ethyl)-4,5,6,7-tetrahydro-1H-pyrazolo[4,3-c]pyridin-3-yl]-benzene-1,3-diol [(1) A=Cl, X=N, R=$C_6H_{12}NO_2$, m=1 n=1]

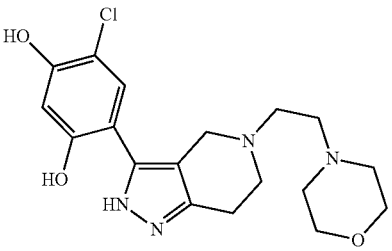

Operating as in Example 17, but employing 4-(2-chloroethyl)-morpholine hydrochloride, the title compound was obtained in 47% yield.

HRMS (ESI): m/z calcd for $C_{18}H_{24}ClN_4O_3^+$ 379.1532 [M+H]$^+$, found 379.1526.

Example 19

Conversion 4

Preparation of 4-Chloro-6-{5-[(trans-4-methoxycyclohexyl)methyl]-4,5,6,7-tetrahydro-1H-pyrazolo[4,3-c]pyridin-3-yl}-benzene-1,3-diol trifluoroacetate (q) [(1), A=Cl, X=N, R=$C_8H_{13}O_2$, m=1 n=1]

4-Chloro-6-{5-[(cis-4-methoxycyclohexyl)methyl]-4,5,6,7-tetrahydro-1H-pyrazolo[4,3-c]pyridin-3-yl}-benzene-1,3-diol trifluoroacetate (r) [(1), A=Cl, X=N, R=$C_8H_{13}O_2$, m=1 n=1]

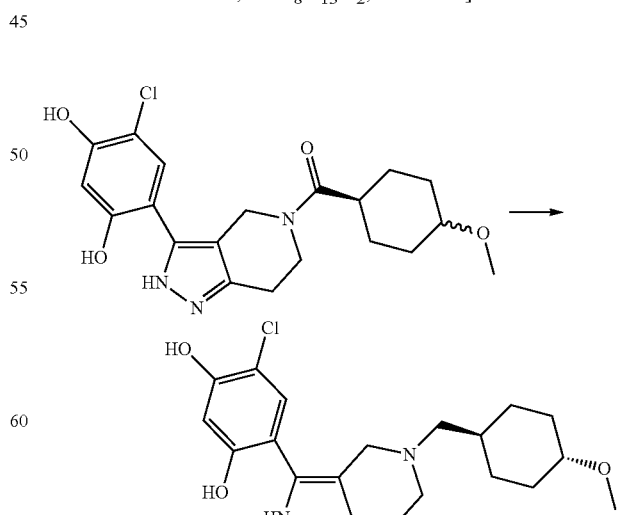

q

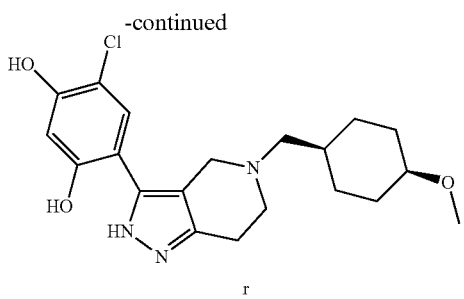

r

To stirred suspension of 4-chloro-6-{5-[((trans, cis) 4-methoxycyclohexyl)carbonyl]-4,5,6,7-tetrahydro-1H-pyrazolo[4,3-c]pyridin-3-yl}benzene-1,3-diol (0.198 g, 0.49 mmol) in THF (5 mL) was added 1N borane-THF complex in THF (2 mL). The mixture was stirred under reflux for 6 hours. Water (1 mL) was carefully added followed by the addition of 1N NaOH solution (2 mL). The mixture was thoroughly extracted with ethyl acetate, dried over $Na_2SO_4$ and evaporated to dryness. The residue was purified by preparative HPLC to afford 12 mg of 4-chloro-6-{5-[(trans-4-methoxycyclohexyl)methyl]-4,5,6,7-tetrahydro-1H-pyrazolo[4,3-c]pyridin-3-yl}-benzene-1,3-diol trifluoroacetate (q) in 6% yield.

HRMS (ESI): m/z calcd for $C_{20}H_{27}ClN_3O_3^+$ 392.1736 [M+H]$^+$, found 392.1748 and 11 mg of 4-chloro-6-{5-[(cis-4-methoxycyclohexyl)methyl]-4,5,6,7-tetrahydro-1H-pyrazolo[4,3-c]pyridin-3-yl}benzene-1,3-diol trifluoroacetate in 6% yield.

HRMS (ESI): m/z calcd for $C_{20}H_{27}ClN_3O_3^+$ 392.1736 [M+H]$^+$, found 392.1736.

Example 20

Step k7

Preparation of 4-Chloro-6-[5-(2-chloropyrimidin-4-yl)-4,5,6,7-tetrahydro-isoxazolo[4,3-c]pyridin-3-yl] benzene-1,3-diol [(1), A=Cl, X=O, R=$C_4H_2ClN_2$, m=1 n=1]

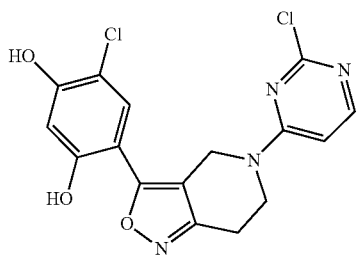

To a solution of 4-chloro-6-(4,5,6,7-tetrahydro-isoxazolo[4,3-c]pyridin-3-yl)benzene-1,3-diol hydrochloride (0.030 g, 0.1 mmol) in DMF (0.5 mL) and DIPEA (0.070 mL, 0.4 mmol), 2,4-dichloropyrimidine (0.016 g, 0.11 mmol) was added. The mixture was stirred overnight at room temperature. Then, after dilution with water, the precipitate was collected, washed with ethanol to provide 30 mg (79% yield) of the title compound.

$^1$H NMR (400 MHz, DMSO-$d_6$) δ ppm 2.88 (m, 2H) 4.00 (m, 2H) 4.83 (dd, 2H) 6.71 (s, 1H) 7.08 (s, 1H) 7.42 (s, 1H) 8.36 (s, 1H) 10.61 (bs, 1H) 10.67 (bs, 1H)

HRMS (ESI): m/z calcd for $C_{16}H_{13}Cl_2N_4O_3^+$ 379.0359 [M+H]$^+$, found 379.0365.

The invention claimed is:

1. A compound of formula (I)

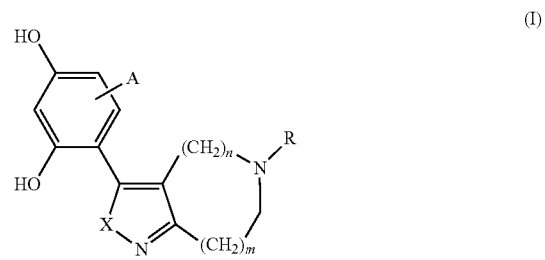

wherein:
A is halogen or an optionally substituted linear or branched ($C_1$-$C_6$) alkyl, ($C_2$-$C_6$) alkenyl or ($C_2$-$C_6$) alkynyl;
X is oxygen or nitrogen;
R is hydrogen, $(CH_2)_p$—COR1, $(CH_2)_p$—COOR1, ZNHR1', $(CH_2)_p$—RP, CH(R1')$_2$ or SO$_2$R2,
wherein
R1 is hydrogen or R1';
R1' is a group optionally substituted selected from linear or branched ($C_1$-$C_6$) alkyl, ($C_2$-$C_6$) alkenyl, ($C_2$-$C_6$) alkynyl, ($C_3$-$C_8$) cycloalkyl, heterocyclyl, aryl and heteroaryl;
Z is a C=O or C=S group;
R2 is a group optionally substituted selected from linear or branched ($C_1$-$C_6$) alkyl, ($C_3$-$C_8$) cycloalkyl, heterocyclyl, aryl and heteroaryl;
m, n and p are independently an integer from 0 to 2, and pharmaceutically acceptable salts thereof.

2. A compound of formula (I) according to claim 1 wherein:
m is 0 and n is 2, namely 4,5,6,7-tetrahydro-1H-pyrazolo[3,4-c]pyridine derivatives and 4,5,6,7-tetrahydroisoxazolo[3,4-c]pyridine derivatives.

3. A compound of formula (I) according to claim 1 wherein:
wherein m is 1 and n is 1, namely 4,5,6,7-tetrahydro-2H-pyrazolo[4,3-c]pyridine derivatives and 4,5,6,7-tetrahydro-isoxazolo[4,3-c]pyridine.

4. A compound of formula (I) according to claim 1 wherein:
m is 2 and n is 0, namely 4,5,6,7-tetrahydro-2H-pyrazolo[4,3-b]pyridine derivatives and 4,5,6,7-tetrahydro-isoxazolo[4,3-b]pyridine derivatives.

5. A compound of formula (I) according to claim 1 wherein:
m is 0 and n is 1, namely 2,4,5,6-tetrahydropyrrolo[3,4-c]pyrazole and 5,6-dihydro-4H-pyrrole[3,4-c]isoxazole derivatives.

6. A compound of formula (I) according to claim 1 wherein:
m is 1 and n is 0, namely 1,4,5,6-tetrahydropyrrolo[3,2-c]pyrazole and 5,6-dihydro-4H-pyrrolo[3,2-c]isoxazole derivatives.

7. A compound of formula (I) according to claim 1, wherein A is halogen.

8. A compound of formula (I) according to claim 1, wherein R is $(CH_2)_p$—COR1 or $(CH_2)_p$—R1',
wherein R1, R1' and p are as defined in claim 1.

9. A compound or a pharmaceutically acceptable salt which is:

[3-(5-chloro-2,4-dihydroxyphenyl)-1,4,6,7-tetrahydro-5H-pyrazolo[4,3-c]pyridin-5-yl][4-(dimethylamino)phenyl]methanone,

[3-(5-chloro-2,4-dihydroxyphenyl)-1,4,6,7-tetrahydro-5H-pyrazolo[4,3-c]pyridin-5-yl](phenyl)methanone,

[3-(5-chloro-2,4-dihydroxyphenyl)-1,4,6,7-tetrahydro-5H-pyrazolo[4,3-c]pyridin-5-yl](4-nitrophenyl)methanone, 1-[3-(5-chloro-2,4-dihydroxyphenyl)-1,4,6,7-tetrahydro-5H-pyrazolo[4,3-c]pyridin-5-yl]-2-[4-(methylsulfonyl)phenyl]ethanone,

[3-(5-chloro-2,4-dihydroxyphenyl)-1,4,6,7-tetrahydro-5H-pyrazolo[4,3-c]pyridin-5-yl][4-(hydroxymethyl)phenyl]methanone,

[3-(5-chloro-2,4-dihydroxyphenyl)-1,4,6,7-tetrahydro-5H-pyrazolo[4,3-c]pyridin-5-yl](thiophen-3-yl)methanone, 4-{[3-(5-chloro-2,4-dihydroxyphenyl)-1,4,6,7-tetrahydro-5H-pyrazolo[4,3-c]pyridin-5-yl]carbonyl}benzonitrile,

[3-(5-chloro-2,4-dihydroxyphenyl)-1,4,6,7-tetrahydro-5H-pyrazolo[4,3-c]pyridin-5-yl](3-methoxyphenyl)methanone,

[3-(5-chloro-2,4-dihydroxyphenyl)-1,4,6,7-tetrahydro-5H-pyrazolo[4,3-c]pyridin-5-yl](4-methoxyphenyl)methanone,

[3-(5-chloro-2,4-dihydroxyphenyl)-1,4,6,7-tetrahydro-5H-pyrazolo[4,3-c]pyridin-5-yl][4-(methylsulfanyl)phenyl]methanone,

[3-(5-chloro-2,4-dihydroxyphenyl)-1,4,6,7-tetrahydro-5H-pyrazolo[4,3-c]pyridin-5-yl][4-(1H-pyrrol-1-yl)phenyl]methanone,

[3-(5-chloro-2,4-dihydroxyphenyl)-1,4,6,7-tetrahydro-5H-pyrazolo[4,3-c]pyridin-5-yl][4-(1,3-oxazol-5-yl)phenyl]methanone, 4-{[3-(5-chloro-2,4-dihydroxyphenyl)-1,4,6,7-tetrahydro-5H-pyrazolo[4,3-c]pyridin-5-yl]carbonyl}benzenesulfonamide,

[3-(5-chloro-2,4-dihydroxyphenyl)-1,4,6,7-tetrahydro-5H-pyrazolo[4,3-c]pyridin-5-yl](1,4-dioxaspiro[4.5]dec-8-yl)methanone,

[3-(5-chloro-2,4-dihydroxyphenyl)-1,4,6,7-tetrahydro-5H-pyrazolo[4,3-c]pyridin-5-yl](tetrahydro-2H-pyran-4-yl)methanone,

[3-(5-chloro-2,4-dihydroxyphenyl)-1,4,6,7-tetrahydro-5H-pyrazolo[4,3-c]pyridin-5-yl][4-(1H-imidazol-1-yl)phenyl]methanone,

[3-(5-chloro-2,4-dihydroxyphenyl)-1,4,6,7-tetrahydro-5H-pyrazolo[4,3-c]pyridin-5-yl](trans-4-methoxycyclohexyl)methanone, 4-chloro-6-{5-[3-(1H-imidazol-1-yl)benzyl]-4,5,6,7-tetrahydro-1H-pyrazolo[4,3-c]pyridin-3-yl}benzene-1,3-diol,

[3-(5-chloro-2,4-dihydroxyphenyl)-1,4,6,7-tetrahydro-5H-pyrazolo[4,3-c]pyridin-5-yl](1,5-dioxaspiro[5.5]undec-9-yl)methanone,

[3-(5-chloro-2,4-dihydroxyphenyl)-6,7-dihydroisoxazolo[4,3-c]pyridin-5(4H)-yl][4-(dimethylamino)phenyl]methanone, 1-[3-(5-chloro-2,4-dihydroxyphenyl)-6,7-dihydroisoxazolo[4,3-c]pyridin-5(4H)-yl]-2-[4-(methylsulfonyl)phenyl]ethanone,

[3-(5-chloro-2,4-dihydroxyphenyl)-6,7-dihydroisoxazolo[4,3-c]pyridin-5(4H)-yl][4-(hydroxymethyl)phenyl]methanone,

[3-(5-chloro-2,4-dihydroxyphenyl)-6,7-dihydroisoxazolo[4,3-c]pyridin-5(4H)-yl](6-hydroxypyridin-3-yl)methanone, 4-{[3-(5-chloro-2,4-dihydroxyphenyl)-6,7-dihydroisoxazolo[4,3-c]pyridin-5(4H)-yl]carbonyl}benzonitrile, 4-{[3-(5-chloro-2,4-dihydroxyphenyl)-6,7-dihydroisoxazolo[4,3-c]pyridin-5(4H)-yl]carbonyl}benzenesulfonamide,

[3-(5-chloro-2,4-dihydroxyphenyl)-6,7-dihydroisoxazolo[4,3-c]pyridin-5(4H)-yl][2-(pyridin-3-yl)-1,3-thiazol-4-yl]methanone,

[3-(5-chloro-2,4-dihydroxyphenyl)-6,7-dihydroisoxazolo[4,3-c]pyridin-5(4H)-yl](4-nitrophenyl)methanone,

[3-(5-chloro-2,4-dihydroxyphenyl)-6,7-dihydroisoxazolo[4,3-c]pyridin-5(4H)-yl][4-(morpholin-4-yl)phenyl]methanone, 1-[3-(5-chloro-2,4-dihydroxyphenyl)-6,7-dihydroisoxazolo[4,3-c]pyridin-5(4H)-yl]-2-[4-(hydroxymethyl)phenyl]ethanone,

[4-(aminomethyl)cyclohexyl][3-(5-chloro-2,4-dihydroxyphenyl)-6,7-dihydroisoxazolo[4,3-c]pyridin-5(4H)-yl]methanone,

[3-(5-chloro-2,4-dihydroxyphenyl)-6,7-dihydroisoxazolo[4,3-c]pyridin-5(4H)-yl](trans-4-methoxycyclohexyl)methanone, 1-[3-(5-chloro-2,4-dihydroxyphenyl)-6,7-dihydroisoxazolo[4,3-c]pyridin-5(4H)-yl]-3-(morpholin-4-yl)propan-1-one,

[3-(5-chloro-2,4-dihydroxyphenyl)-6,7-dihydroisoxazolo[4,3-c]pyridin-5(4H)-yl][3-(1H-imidazol-1-yl)phenyl]methanone,

[3-(5-chloro-2,4-dihydroxyphenyl)-6,7-dihydroisoxazolo[4,3-c]pyridin-5(4H)-yl][4-(1H-imidazol-1-yl)phenyl]methanone,

[3-(5-chloro-2,4-dihydroxyphenyl)-6,7-dihydroisoxazolo[4,3-c]pyridin-5(4H)-yl][4-(1H-imidazol-1-ylmethyl)phenyl]methanone, 4-chloro-6-{5-[4-(dimethylamino)benzyl]-4,5,6,7-tetrahydro-1H-pyrazolo[4,3-c]pyridin-3-yl}benzene-1,3-diol, 4-chloro-6-(5-{[6-(morpholin-4-yl)pyridin-3-yl]methyl}-4,5,6,7-tetrahydro-1H-pyrazolo[4,3-c]pyridin-3-yl)benzene-1,3-diol, 3-[3-(5-chloro-2,4-dihydroxyphenyl)-1,4,6,7-tetrahydro-5H-pyrazolo[4,3-c]pyridin-5-yl]-1-(morpholin-4-yl)propan-1-one, 4-chloro-6-[5-(4-ethoxybenzyl)-4,5,6,7-tetrahydro-1H-pyrazolo[4,3-c]pyridin-3-yl]benzene-1,3-diol, 4-chloro-6-[5-(3,4-dimethoxybenzyl)-4,5,6,7-tetrahydro-1H-pyrazolo[4,3-c]pyridin-3-yl]benzene-1,3-diol, 4-chloro-6-{5-[3-(1H-1,2,4-triazol-1-yl)benzyl]-4,5,6,7-tetrahydro-1H-pyrazolo[4,3-c]pyridin-3-yl}benzene-1,3-diol, 4-chloro-6-{5-[4-(1H-1,2,4-triazol-1-yl)benzyl]-4,5,6,7-tetrahydro-1H-pyrazolo[4,3-c]pyridin-3-yl}benzene-1,3-diol, 4-chloro-6-(5-{4-[(2-hydroxyethyl)(methyl)amino]benzyl}-4,5,6,7-tetrahydro-1H-pyrazolo[4,3-c]pyridin-3-yl)benzene-1,3-diol, 4-chloro-6-[5-(3-ethoxy-4-methoxybenzyl)-4,5,6,7-tetrahydro-1H-pyrazolo[4,3-c]pyridin-3-yl]benzene-1,3-diol, 1-(4-{[3-(5-chloro-2,4-dihydroxyphenyl)-1,4,6,7-tetrahydro-5H-pyrazolo[4,3-c]pyridin-5-yl]methyl}phenyl)pyrrolidin-2-one, 4-chloro-6-{5-[4-(morpholin-4-yl)benzyl]-4,5,6,7-tetrahydro-1H-pyrazolo[4,3-c]pyridin-3-yl}benzene-1,3-diol, 4-chloro-6-(5-{[2-(morpholin-4-yl)pyridin-4-yl]methyl}-4,5,6,7-tetrahydro-1H-pyrazolo[4,3-c]pyridin-3-yl)benzene-1,3-diol, 4-chloro-6-[5-(3-hydroxy-4-methoxybenzyl)-4,5,6,7-tetrahydro-1H-pyrazolo[4,3-c]pyridin-3-yl]benzene-1,3-diol, 4-chloro-6-{5-[4-(1H-1,2,3-triazol-1-yl)benzyl]-4,5,6,7-tetrahydro-1H-pyrazolo[4,3-c]pyridin-3-yl}benzene-1,3-diol, 4-chloro-6-{5-[4-(1H-imidazol-1-yl)benzyl]-4,5,6,7-tetrahydro-1H-pyrazolo[4,3-c]pyridin-3-yl}benzene-1,3-diol, 4-chloro-6-{5-[3-(1H-imidazol-1-yl)benzyl]-4,5,6,7-tetrahydro-1H-pyrazolo[4,3-c]pyridin-3-yl}benzene-1,3-diol, 4-chloro-6-{5-[4-(dimethylamino)benzyl]-4,5,6,7-tetrahydroisoxazolo[4,3-c]pyridin-3-yl}benzene-1,3-diol, 4-chloro-6-(5-{[6-(morpholin-4-yl)pyridin-3-yl]methyl}-4,5,6,7-tetrahydroisoxazolo[4,3-c]pyridin-3-yl)benzene-1,3-diol, 4-chloro-6-{5-[3-(1H-imidazol-1-yl)benzyl]-4,5,6,7-tetrahydroisoxazolo[4,3-c]pyridin-3-yl}benzene-1,3-diol, 4-[3-(5-chloro-2,4-dihydroxyphenyl)-6,7-dihydroisoxazolo[4,3-c]pyridin-5(4H)-yl]butan-2-one, 4-chloro-6-[5-(pyridin-4-ylmethyl)-4,5,6,7-tetrahydroisoxazolo[4,3-c]pyridin-3-yl]benzene-1,3-diol, 4-chloro-6-(5-{[5-(hydroxymethyl)furan-2-yl]methyl}-4,5,6,7-tetrahydroisoxazolo[4,3-c]pyridin-3-yl)benzene-1,3-diol, 4-{[3-(5-chloro-2,4-dihydroxyphenyl)-6,7-dihydroisoxazolo[4,3-c]pyridin-5(4H)-yl]methyl}benzonitrile, 4-chloro-6-[5-(4-ethoxybenzyl)-4,5,6,7-tetrahydroisoxazolo[4,3-c]pyridin-3-yl]benzene-1,3-diol, 4-chloro-6-[5-(3-hydroxy-4-methoxybenzyl)-4,5,6,7-tetrahydroisoxazolo[4,3-c]pyridin-3-yl]benzene-1,3-diol, 4-chloro-6-[5-(3,4-dimethoxybenzyl)-4,5,6,7-tetrahydroisoxazolo[4,3-c]pyridin-3-yl]benzene-1,3-diol, 4-chloro-6-(5-{[2-(morpholin-4-yl)-1,3-thiazol-5-yl]methyl}-4,5,6,7-tetrahydroisoxazolo[4,3-c]pyridin-3-yl)benzene-1,3-diol, 4-chloro-6-{5-[3-(morpholin-4-yl)propyl]-4,5,6,7-tetrahydroisoxazolo[4,3-c]pyridin-3-yl}benzene-1,3-diol, 4-chloro-6-{5-[3-(1H-1,2,4-triazol-1-yl)benzyl]-4,5,6,7-tetrahydroisoxazolo[4,3-c]pyridin-3-yl}benzene-1,3-diol, 1-(4-{[3-(5-chloro-2,4-dihydroxyphenyl)-6,7-dihydroisoxazolo[4,3-c]pyridin-5(4H)-yl]methyl}phenyl)pyrrolidin-2-one, 4-chloro-6-{5-[4-(morpholin-4-yl)benzyl]-4,5,6,7-tetrahydroisoxazolo[4,3-c]pyridin-3-yl}benzene-1,3-diol, 4-chloro-6-{5-[4-(1H-imidazol-1-yl)benzyl]-4,5,6,7-tetrahydroisoxazolo[4,3-c]pyridin-3-yl}benzene-1,3-diol, 3-[3-(5-chloro-2,4-dihydroxyphenyl)-6,7-dihydroisoxazolo[4,3-c]pyridin-5(4H)-yl]-1-(morpholin-4-yl)propan-1-one and 4-chloro-6-(5-{[2-(morpholin-4-yl)pyridin-4-yl]methyl}-4,5,6,7-tetrahydroisoxazolo[4,3-c]pyridin-3-yl)benzene-1,3-diol.

10. A process for preparing a compound of formula (I) as defined in claim 1, characterized in that the process comprises:

k) condensing a compound of formula (I):

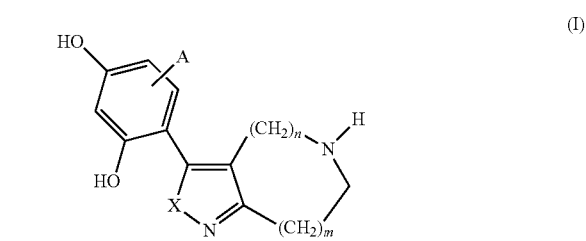

(I)

wherein A, X, m and n are as defined in claim 1, according to any one of the alternative steps:

k1) with a compound of formula (10):

R1COW        (10)

wherein W is OH or an activated group such as chlorine, 1-imidazolyl, 1-succinimidyloxy, 1-hydroxybenzotriazolyl or O-isoureyl, and R1 is as defined in claim 1, to give a compound of formula (I):

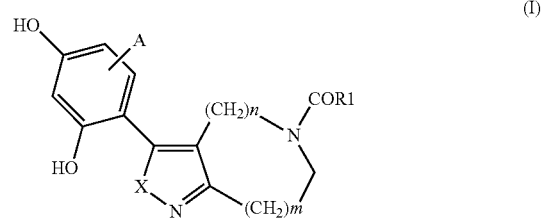

(I)

wherein A, X, m, n, and R1 are as defined above;

k2) with a compound of formula (11):

R1'OCOHal        (11)

wherein Hal is halogen and R1' is as defined in claim 1, to give a compound of formula (I):

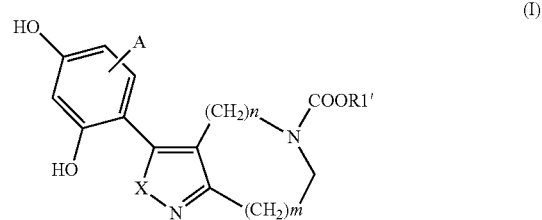

(I)

wherein A, X, m, n, and R1' are as defined above;

k3) with a compound of formula (12):

R1'N=Z        (12)

wherein Z is as defined in claim 1 and R1' is as defined above, to give a compound of formula (I):

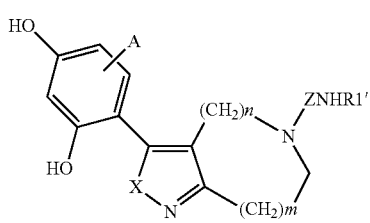 (I)

wherein A, X, m, n, and R1' are as defined above;
k4) with a compound of formula (13):

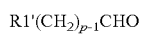 (13)

wherein p is as defined in claim 1 and R1' is as defined above, to give a compound of formula (I):

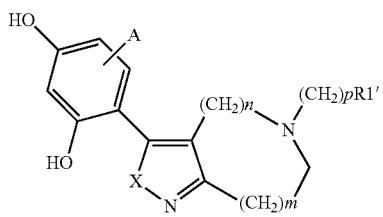 (I)

wherein A, X, m, n, p and R1' are as defined above;
k5) with a compound of formula (14):

R1'COR1' (14)

wherein R1' the same or different are as defined above or taken together may form an optionally substituted cycloalkyl or heterocyclyl containing one or more heteroatom selected from S, O or N to give a compound of formula (I):

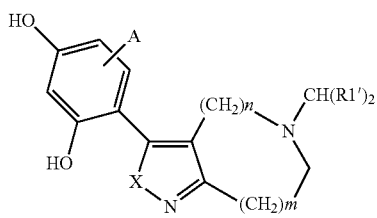 (I)

wherein A, X, m, n, and R1' are as defined above;
k6) with a compound of formula (15):

 (15)

wherein R2 is as defined in claim 1 and Hal is as defined above, to give a compound of formula (I):

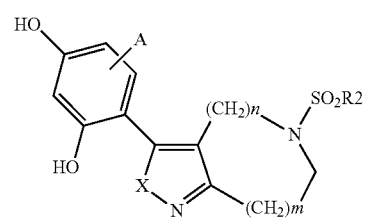 (I)

wherein A, X, m, n, and R2 are as defined above;
or
k7) with a compound of formula (16):

R1"Hal (16)

wherein R1" is optionally substituted $(C_1-C_6)$ alkyl or aryl, such as phenyl with an electron withdrawing group such as nitro, cyano or methylsulfonyl in ortho or para position to the halogen, or heteroaryl such as pyridine, pyrimidine, pyrazine, pyridazine, quinoline or isoquinoline with the halogen in ortho or para position to one of the nitrogen, and Hal is as defined above, to give a compound of formula (I):

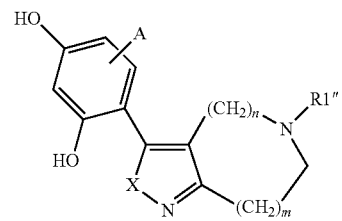 (I)

wherein A, X, m, n, and R1" are as defined above;
or
k8) with a compound of formula (17):

$CH_2=CHCOR1'$ (17)

wherein R1' is defined as above, to give a compound of formula (I):

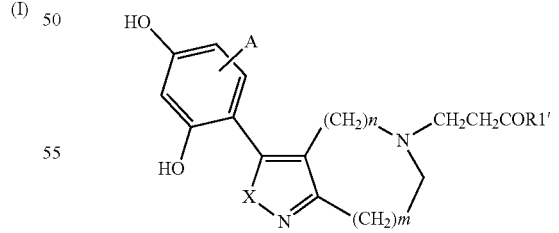 (I)

wherein A, X, m, n, and R1' are as defined above;
optionally separating the resultant compound of formula (I) into the single isomers, and/or converting it into another derivative of formula (I) and or into a pharmaceutically acceptable salt.

11. A process according to claim 10, characterized in that the compound of formula $(I)_A$ wherein R is hydrogen, X is nitrogen, A is halogen or an optionally substituted linear or branched ($C_1$-$C_6$) alkyl, ($C_2$-$C_6$) alkenyl or ($C_2$-$C_6$) alkynyl, and m and n are independently an integer from 0 to 2, is prepared according to the following steps:

a) condensing a compound of formula (2):

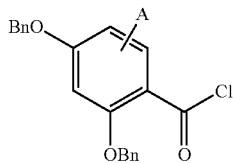

(2)

wherein Bn is benzyl and A is as defined above, with a compound of formula (3):

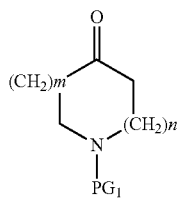

(3)

wherein $PG_1$ is an N protecting group such as benzyl or tert-butyloxycarbonyl and m and n are as defined above;

b) condensing the resultant compound of formula (4):

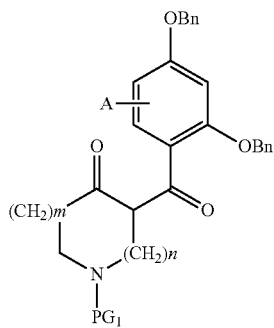

(4)

wherein Bn, A, $PG_1$, m and n are as defined above, with hydrazine hydrate or an hydrazine salt;

c1) either reducing the resultant compound of formula (5):

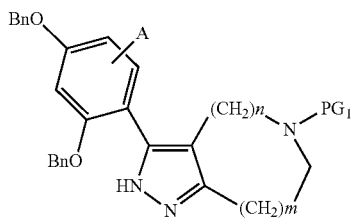

(5)

wherein Bn, A, m and n are as defined above and $PG_1$ is benzyl, with $H_2$ and a suitable catalyst, to give a compound of formula $(I)_A$:

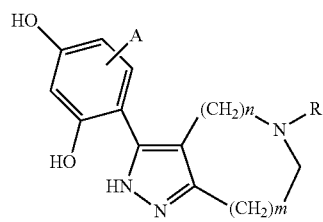

$(I)_A$ wherein A, m and n are defined above and R is hydrogen;

or c2) removing the $PG_1$, wherein $PG_1$ is tert-butyloxycarbonyl, from the compound of formula (5) as defined above, with hydrochloric, trifluoroacetic, methanesulfonic or formic acid;

d) reducing the resultant compound of formula (6):

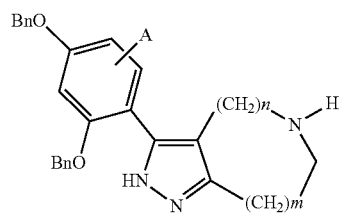

(6)

wherein Bn, A, m and n are as defined above, with $H_2$ and a suitable catalyst, to give a compound of formula $(I)_A$ as defined above, wherein R is hydrogen;

or c3) reducing the compound of formula (5) as defined above, wherein $PG_1$ is tert-butyloxycarbonyl, with $H_2$ and a suitable catalyst, to give a compound of formula $(I)_A$:

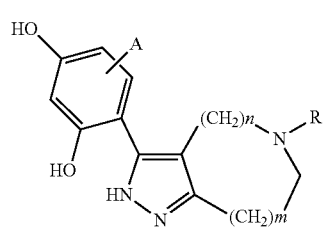

$(I)_A$ wherein A, m and n are as defined above and R is tert-butyloxycarbonyl;

e) optionally removing the tert-butyloxycarbonyl from the resultant compound of formula $(I)_A$ wherein R is tert-butyloxycarbonyl, with hydrochloric, trifluoroacetic, methanesulfonic or formic acid, to give a compound of formula (I) wherein R is hydrogen, if necessary or wanted after any of the above steps a) to e), separating the optionally obtained mixture of the regioisomers into the single isomers.

12. A process according to claim 10, characterized in that the compound of formula $(I)_B$ wherein R is hydrogen, X is oxygen, A is halogen or an optionally substituted linear or branched ($C_1$-$C_6$) alkyl, ($C_2$-$C_6$) alkenyl or ($C_2$-$C_6$) alkynyl, and m and n are independently an integer from 0 to 2, is prepared according to the following steps:

f1) either reducing a compound of formula (4):

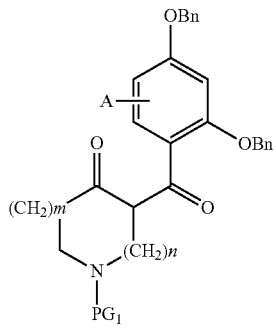
(4)

wherein $B_n$ is benzyl, A is halogen or an optionally substituted linear or branched ($C_1$-$C_6$) alkyl, ($C_2$-$C_6$) alkenyl or ($C_2$-$C_6$) alkynyl, $PG_1$ is tert-butyloxycorbonyl, and m and n are independently an integer from 0 to 2, with $H_2$ and a suitable catalyst, to give a compound of formula (7):

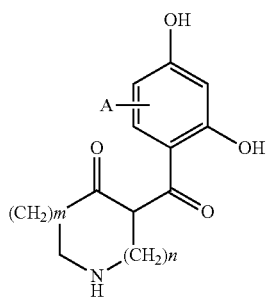
(7)

wherein A, m and n are as defined above;

or f2) removing the $PG_1$ from a compound of formula (4) wherein $PG_1$ is tert-butyloxycarbonyl, with hydrochloric, trifluoroacetic, methanesulfonic or formic acid;

g) reducing the resultant compound of formula (8):

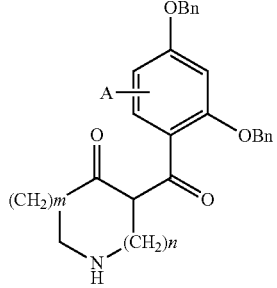
(8)

wherein A, m and n are as defined above and Bn is as defined above, with $H_2$ and a suitable catalyst;

h) condensing the resultant compound of formula (7):

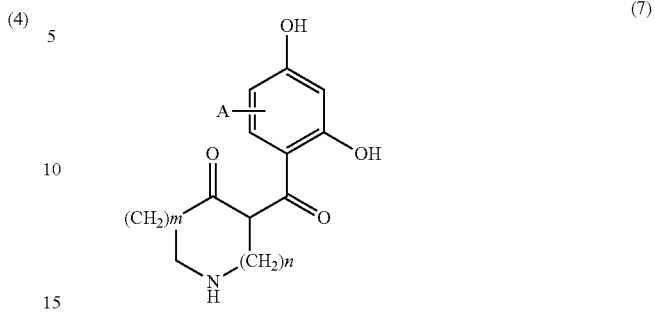
(7)

wherein A, m and n are as defined above, with $NH_2OH \cdot HCl$ or $NH_2OH \cdot H_2SO_4$ in presence of an organic base, to give a compound of formula $(I)_B$:

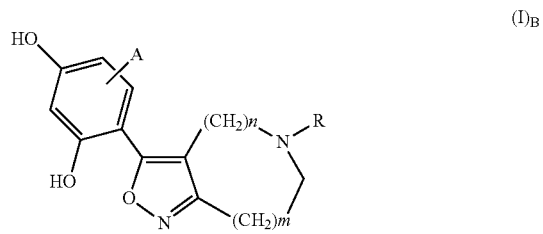
$(I)_B$ wherein A, m and n are as defined above and R is hydrogen;

or f3) reducing a compound of formula (4) wherein $PG_1$ is tert-butyloxycarbonyl with $H_2$ and a suitable catalyst;

i) condensing the resultant compound of formula (9):

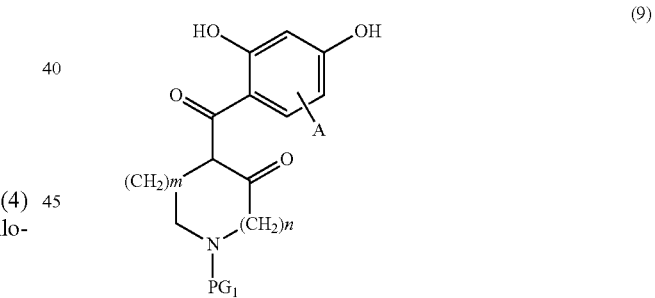
(9)

wherein $PG_1$ is tert-butoxycarbonyl and A, m and n are as defined above, with $NH_2OH \cdot HCl$ or $NH_2OH \cdot H_2SO_4$ in presence of an organic base, to give a compound of formula $(I)_B$:

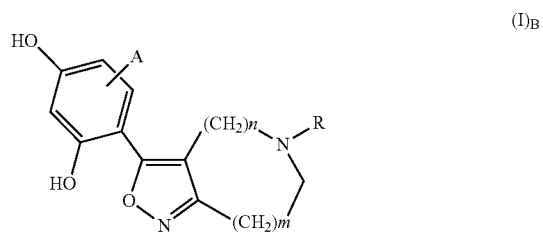
$(I)_B$ wherein R is tert-butyloxycarbonyl and a, m and n are as defined above;

j) optionally removing the tert-butyloxycarbonyl from the resultant compound of formula $(I)_B$ wherein R is tert-butyloxycarbonyl, with hydrochloric, trifluoroacetic, methanesulfonic or formic acid, to give a compound of formula $(I)_B$ wherein R is hydrogen, if necessary or wanted after any of the above steps f1) to j), separating the optionally obtained mixture of the regioisomers into the single isomers.

13. A method for treating a disease selected from the group consisting of ovarian cancer, breast cancer and melanoma, which comprises administering to a mammal in need thereof an effective amount of a compound of formula (I) as defined in claim 1.

14. The method according to claim 13 wherein the mammal in need thereof is a human.

15. An in-vitro method for inhibiting HSP90 protein activity which comprises contacting said protein with an effective amount of a compound of formula (I) as defined in claim 1.

16. A pharmaceutical composition comprising a therapeutically effective amount of a compound of formula (I) as defined in claim 1 and, at least, one pharmaceutically acceptable excipient, carrier and/or diluent.

17. A product or kit comprising a compound of formula (I) as defined in claim 1 or a pharmaceutical composition thereof comprising a therapeutically effective amount of said compound of formula (1) and at least one pharmaceutically acceptable excipient, carrier and/or diluent, and one or more chemotherapeutic agents, as a combined preparation for simultaneous, separate or sequential administration in ovarian cancer, breast cancer and melanoma therapy.

18. A pharmaceutical composition comprising a therapeutically effective amount of a compound of formula (I) or a pharmaceutically acceptable salt thereof, as defined in claim 1.

19. A biochemical tool, comprising the compound of formula (1) as defined in claim 1 or a salt thereof.

20. The biochemical tool of claim 19, wherein said tool is a molecular probe.

* * * * *